US009656981B2

(12) United States Patent
Spigelman et al.

(10) Patent No.: US 9,656,981 B2
(45) Date of Patent: May 23, 2017

(54) PERIPHERALLY-ACTING CANNABINOID RECEPTOR AGONISTS FOR CHRONIC PAIN

(71) Applicant: The Regents of the University of California, Oakland, CA (US)

(72) Inventors: Igor Spigelman, Los Angeles, CA (US); Herbert H. Seltzman, Raleigh, NC (US); Craig Shiner, Durham, NC (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 14/416,026

(22) PCT Filed: Jul. 19, 2013

(86) PCT No.: PCT/US2013/051369
§ 371 (c)(1),
(2) Date: Jan. 20, 2015

(87) PCT Pub. No.: WO2014/015298
PCT Pub. Date: Jan. 23, 2014

(65) Prior Publication Data
US 2015/0239859 A1    Aug. 27, 2015

Related U.S. Application Data

(60) Provisional application No. 61/673,904, filed on Jul. 20, 2012, provisional application No. 61/792,337, filed on Mar. 15, 2013.

(51) Int. Cl.
| | |
|---|---|
| *A61K 31/5375* | (2006.01) |
| *C07D 307/52* | (2006.01) |
| *C07D 209/08* | (2006.01) |
| *C07D 209/12* | (2006.01) |
| *C07D 215/12* | (2006.01) |
| *C07D 215/14* | (2006.01) |
| *C07D 217/02* | (2006.01) |
| *C07D 295/03* | (2006.01) |
| *C07D 295/073* | (2006.01) |
| *C07D 295/037* | (2006.01) |
| *C07D 295/096* | (2006.01) |
| *C07C 13/465* | (2006.01) |
| *C07C 39/04* | (2006.01) |
| *C07C 43/215* | (2006.01) |
| *C07C 49/788* | (2006.01) |

(52) U.S. Cl.
CPC .......... *C07D 307/52* (2013.01); *C07C 13/465* (2013.01); *C07C 39/04* (2013.01); *C07C 43/215* (2013.01); *C07C 49/788* (2013.01); *C07D 209/08* (2013.01); *C07D 209/12* (2013.01); *C07D 215/12* (2013.01); *C07D 215/14* (2013.01); *C07D 217/02* (2013.01); *C07D 295/03* (2013.01); *C07D 295/037* (2013.01); *C07D 295/073* (2013.01); *C07D 295/096* (2013.01)

(58) Field of Classification Search
CPC .. C07D 307/52; C07D 209/08; C07D 209/12; C07D 215/12; C07D 215/14; C07D 217/02; C07D 295/03; C07D 295/037; C07D 295/073; C07D 295/096; A61K 31/5375
See application file for complete search history.

(56) References Cited

U.S. PATENT DOCUMENTS

| | | |
|---|---|---|
| 5,013,837 A | 5/1991 | Ward et al. |
| 5,292,736 A | 3/1994 | Kumar et al. |
| 6,013,648 A | 1/2000 | Rinaldi et al. |

OTHER PUBLICATIONS

Kumar et al., Bioorganic & Medicinal Chemistry Letters, vol. 5, No. 4, pp. 381-386, 1995.*
Huffman et al., "3-Indolyl-1-naphthylmethanes: New Cannabimimetic Indoles Provide Evidence for Aromatic Stacking Interactions with the $CB_1$ Cannabinoid Receptor", Bioorganic & Medicinal Chemistry, vol. 11, pp. 539-549. (2003).
Kovalishin et al., "A New Algorithm for Spatial Learning of Artificial Neural Networks Based on Lattice Models of Chemical Structures for QSAR Analysis", Pharmaceutical Chemistry Journal, vol. 35, No. 2, pp. 78-84. (2001).
Shim et al., "Three-Dimensional Quantitative Structure-Activity Relationship Study of the Cannabimimetic (Aminoalkyl)indoles Using Comparative Molecular Field Analysis", Journal of Medical Chemistry, vol. 41, pp. 4521-4532. (1998).
Reggio et al., "The Bioactive Conformation of Aminoalkylindoles at the Cannabinoid $CB_1$ and $CB_2$ Receptors: Insights Gained from (E)- and (Z)-Naphthylidene Indenes", Journal of Medicinal Chemistry, Vo. 41, pp. 5177-5187. (1998).
International Search Report dated Nov. 25, 2013, issued in International Application No. PCT/US2013/051369.
Amaya et al., Induction of CB1 cannabinoid receptor by inflammation in primary afferent neurons facilitates antihyperalgesic effect of peripheral CB1 agonist. Pain 124, 175-183 (2006).
Bailey et al., Transient loss of terminals from non-peptidergic nociceptive fibers in the substantia gelatinosa of spinal cord following chronic constriction injury of the sciatic nerve. Neuroscience 138, 675-690 (2006).
Ballantyne et al., Opioid dependence and addiction during opioid treatment of chronic pain. Pain. 129, 235-255 (2007).
Ballantyne, Opioid analgesia: perspectives on right use and utility. Pain Physician 10, 479-491 (2007).
Bennett et al., A peripheral mononeuropathy in rat that produces disorders of pain sensation like those seen in man. Pain 33, 87-107 (1988).
Buggy et al., Lack of analgesic efficacy of oral delta-9-tetrahydrocannabinol in postoperative pain. Pain. 106, 169-172 (2003).
Burgos et al., Cannabinoid agonist WIN 55,212-2 prevents the development of paclitaxel-induced peripheral neuropathy in rats. Possible involvement of spinal glial cells. Eur. J. Pharmacol. 682, 62-72 (2012).

(Continued)

*Primary Examiner* — Rebecca Anderson
(74) *Attorney, Agent, or Firm* — Venable LLP; Keith G. Haddaway; Annette K. Kwok

(57) ABSTRACT

Peripherally acting cannabinoid agonist compounds, pharmaceutical compositions, and methods of using them are presented.

18 Claims, 10 Drawing Sheets

(56) References Cited

OTHER PUBLICATIONS

Calignano et al., Control of pain initiation by endogenous cannabinoids. *Nature* 394, 277-281 (1998).
Clark et al., Computational methods for the prediction of 'drug-likeness'. Drug Discov. Today 5, 49-58 (2000).
Clark, D.E. Rapid calculation of polar molecular surface area and its application to the prediction of transport phenomena. 2. Prediction of blood-brain barrier penetration. J. Pharm. Sci. 88, 815-821 (1999).
D'Ambra et al., A. C-Attached aminoalkylindoles: potent cannabinoid mimetics. Bioorg. Med. Chem. Lett. 6, 17-22 (1996).
Dewey, W.L. Cannabinoid pharmacology. Pharmacol. Rev. 38, 151-178 (1986).
Di Marzo et al., Plant, synthetic, and endogenous cannabinoids in medicine. Annu. Rev. Med. 57, 553-574 (2006).
Di Marzo et al., Anandamide: some like it hot. Trends Pharmacol. Sci. 22, 346-349 (2001).
Dziadulewicz et al., Naphthalen-1-yl-(4-pentyloxynaphthalen-1-yl)methanone: a potent, orally bioavailable human CB1/CB2 dual agonist with antihyperalgesic properties and restricted central nervous system penetration. J. Med. Chem. 50, 3851-3856 (2007).
Eissenstat et al., Aminoalkylindoles: structure-activity relationships of novel cannabinoid mimetics. J. Med. Chem. 38, 3094-3105 (1995).
Finnerup et al., The evidence for pharmacological treatment of neuropathic pain. Pain 150, 573-581 (2010).
Freiman et al., Cannabinoids depress excitatory neurotransmission between the subthalamic nucleus and the globus pallidus. Neuroscience 133, 305-313 (2005).
Fox et al., The role of central and peripheral Cannabinoid$_1$ receptors in the antihyperalgesic activity of cannabinoids in a model of neuropathic pain. *Pain* 92, 91-100 (2001).
Fride et al., Pharmacological activity of the cannabinoid receptor agonist, anandamide, a brain constituent. Eur. J. Pharmacol. 231, 313-314 (1993).
Fulp et al., Towards rational design of cannabinoid receptor 1 (CB1) antagonists for peripheral selectivity. Bioorg. Med. Chem. Lett. 21, 5711-5714 (2011).
Griffin et al., Evidence for the presence of CB2-like cannabinoid receptors on peripheral nerve terminals. Eur. J. Pharmacol. 339, 53-61 (1997).
Guindon et al., Cannabinoid CB2 receptors: a therapeutic target for the treatment of inflammatory and neuropathic pain. Br. J. Pharmacol. 153, 319-334 (2008).
Gutierrez et al., Activation of peripheral cannabinoid CB1 and CB2 receptors suppresses the maintenance of inflammatory nociception: a comparative analysis. Br. J. Pharmacol. 150, 153-163 (2007).
Hargreaves et al., A new and sensitive method for measuring thermal nociception in cutaneous hyperalgesia. Pain 32, 77-88 (1988).
Hampson et al., Cannabinoids, hippocampal function and memory. Life Sci. 65, 715-723 (1999).
Herzberg et al., The analgesic effects of R(+)-WIN 55,212-2 mesylate, a high affinity cannabinoid agonist, in a rat model of neuropathic pain. Neurosci. Lett. 221, 157-160 (1997).
Huffman et al., 1-Methoxy-, 1-deoxy-11-hydroxy- and 11-hydroxy-1-methoxy-Delta(8)-tetrahydrocannabinols: new selective ligands for the CB2 receptor. Bioorg. Med. Chem. 10, 4119-4129 (2002).
Hunter et al., Aromatic interactions. J. Chem. Soc. Perkin Trans. 2, 651-669 (2001).
Izzo et al., The gastrointestinal pharmacology of cannabinoids. Curr. Opin. Pharmacol. 1, 597-603 (2001).
Johanek et al., Activation of peripheral cannabinoid receptors attenuates cutaneous hyperalgesia produced by a heat injury. Pain 109, 432-442 (2004).
Karst et al., Analgesic effect of the synthetic cannabinoid CT-3 on chronic neuropathic pain: a randomized controlled trial. JAMA 290, 1757-1762 (2003).
Kumar et al., Morpholinoalkylindenes as antinociceptive agents: Novel cannabinoid receptor agonists. Bioorganic & Medicinal Chemistry Letters 5, 381-386 (1995).
Laviolette et al., Role of prostaglandins in marihuana-induced bronchodilation. Respiration. 49, 10-15 (1986).
Lichtman et al., The selective cannabinoid antagonist SR 141716A blocks cannabinoid-induced antinociception in rats. Pharmacol Biochem. Behav. 57, 7-12 (1997).
Lichtman et al., Spinal and supraspinal components of cannabinoid-induced antinociception. J. Pharmacol. Exp. Ther. 258, 517-523 (1991).
Lynn et al., Localization of cannabinoid receptors and nonsaturable high-density cannabinoid binding sites in peripheral tissues of the rat: implications for receptor-mediated immune modulation by cannabinoids. J. Pharmacol. Exp. Ther. 268, 1612-1623 (1994).
Maccarrone et al., Effects of cannabinoids on hypothalamic and reproductive function. Handb. Exp. Pharmacol.555-571 (2005).
Machado Rocha et al., Therapeutic use of Cannabis sativa on chemotherapy-induced nausea and vomiting among cancer patients: systematic review and meta-analysis. Eur. J. Cancer Care (Engl.) 17, 431-443 (2008).
Mackie, K. Distribution of cannabinoid receptors in the central and peripheral nervous system. Handb. Exp. Pharmacol.299-325 (2005).
Malan et al., CB2 cannabinoid receptor-mediated peripheral antinociception. Pain 93, 239-245 (2001).
Mao et al., Experimental mononeuropathy reduces the antinociceptive effects of morphine: implications for common intracellular mechanisms involved in morphine tolerance and neuropathic pain. Pain 61, 353-364 (1995).
Martin et al., Behavioral, biochemical, and molecular modeling evaluations of cannabinoid analogs. Pharmacol. Biochem. Behav. 40, 471-478 (1991).
Martin, Prediction of blood-brain barrier penetration: are we missing the point? *Drug Discov. Today* 9, 161-162 (2004).
Martin et al., Suppression of noxious stimulus-evoked activity in the ventral posterolateral nucleus of the thalamus by a cannabinoid agonist: correlation between electrophysiological and antinociceptive effects. *J. Neurosci.* 16, 6601-6611 (1996).
Martin et al., Spinal cannabinoids are anti-allodynic in rats with persistent inflammation. *Pain* 82, 199-205 (1999).
Mathew et al., Efficacy and Safety of COX-2 Inhibitors in the Clinical Management of Arthritis: Mini Review. ISRN. Pharmacol. 2011, Article ID 480291 (2011), 4 pages.
McAllister et al., An aromatic microdomain at the cannabinoid CB1 receptor constitutes an agonist/inverse agonist binding region. J. Med. Chem. 46, 5139-5152 (2003).
McCormack, Celecoxib: a review of its use for symptomatic relief in the treatment of osteoarthritis, rheumatoid arthritis and ankylosing spondylitis. Drugs. 71, 2457-2489 (2011).
Mechoulam et al., Endocannabinoids and neuroprotection. Sci. STKE. 2002, RE5 (2002).
Mosconi et al., Fixed-diameter polyethylene cuffs applied to the rat sciatic nerve induce a painful neuropathy: Ultrastructural morphometric analysis of axonal alterations. Pain 64, 37-57 (1996).
Nurmikko et al., Sativex successfully treats neuropathic pain characterised by allodynia: a randomised, double-blind, placebo-controlled clinical trial. Pain. 133, 210-220 (2007).
Onaivi et al., Discovery of the presence and functional expression of cannabinoid CB2 receptors in brain. Ann. N. Y. Acad. Sci. 1074, 514-536 (2006).
Ossipov et al., The loss of antinociceptive efficacy of spinal morphine in rats with nerve ligation injury is prevented by reducing spinal afferent drive. Neurosci. Lett. 199, 87-90 (1995).
Pascual et al., A cannabinoid agonist, WIN 55,212-2, reduces neuropathic nociception induced by paclitaxel in rats. Pain 118, 23-34 (2005).
Pertwee, R.G. The central neuropharmacology of psychotropic cannabinoids. *Pharmacol. Ther.* 36, 189-261 (1988).
Pertwee et al., Evidence that (−)-7-hydroxy-4'-dimethylheptyl-cannabidiol activates a non-CB(1), non-CB(2), non-TRPV1 target in the mouse vas deferens. Neuropharmacology. 48, 1139-1146 (2005).

(56) References Cited

OTHER PUBLICATIONS

Pitcher et al., Nerve constriction in the rat: model of neuropathic, surgical and central pain. Pain 83, 37-46 (1999).

Porcella et al., The synthetic cannabinoid WIN55212-2 decreases the intraocular pressure in human glaucoma resistant to conventional therapies. Eur. J. Neurosci. 13, 409-412 (2001).

Pryor et al., Interactions between D9-tetrahydrocannabinol and phencyclidine hydrochloride in rats. Pharmacol Biochem. Behav. 6, 123-136 (1977).

Ramasubbu et al., Pharmacological treatment of opioid-induced hyperalgesia: a review of the evidence. J. Pain Palliat. Care Pharmacother. 25, 219-230 (2011).

Rashid et al., Loss of peripheral morphine analgesia contributes to the reduced effectiveness of systemic morphine in neuropathic pain. J. Pharmacol. Exp. Ther. 309, 380-387 (2004).

Rawls et al., GABAA receptors modulate cannabinoid-evoked hypothermia. Pharmacol. Biochem. Behav. 78, 83-91 (2004).

Richardson et al., Antihyperalgesic effects of spinal cannabinoids. Eur. J Pharmacol 345, 145-153 (1998).

Rodriguez et al., Role of the endogenous cannabinoid system in the regulation of motor activity. Neurobiol. Dis. 5, 483-501 (1998).

Ruangsri et al., Relationship of axonal voltage-gated sodium channel 1.8 (NaV1.8) mRNA accumulation to sciatic nerve injury-induced painful neuropathy in rats. J. Biol. Chem. 286, 39836-39847 (2011).

Saarto et al., Antidepressants for neuropathic pain. Cochrane Database Syst. Rev.CD005454 (2007).

Sanudo-Pena et al., Activational role of cannabinoids on movement. Eur. J. Pharmacol. 391, 269-274 (2000).

Siler et al., Systematic review of the comparative effectiveness of antiepileptic drugs for fibromyalgia. J. Pain. 12, 407-415 (2011).

Smith et al., Pharmacological treatment of diabetic neuropathic pain. Drugs 71, 557-589 (2011).

Smith et al., The pharmacological activity of anandamide, a putative endogenous cannabinoid, in mice. J. Pharmacol. Exp. Ther. 270, 219-227 (1994).

Sofia et al., Anti-edema and analgesic properties of delta9-tetrahydrocannabinol (THC). J Pharmacol Exp Ther 186, 646-655 (1973).

Spigelman, I Therapeutic targeting of peripheral cannabinoid receptors in inflammatory and neuropathic pain states in Translational Pain Research: from Mouse to Man (eds. Kruger,L. & Light,A.R.) 99-137 (Taylor & Francis Group, LLC, Boca Raton, 2010).

Strangman et al., Evidence for a role of endogenous cannabinoids in the modulation of acute and tonic pain sensitivity. Brain Res. 813, 323-328 (1998).

Szolcsanyi, J. Anandamide and the question of its functional role for activation of capsaicin receptors. Trends Pharmacol. Sci. 21, 203-204 (2000).

Van Sickle et al., Cannabinoids inhibit emesis through CB1 receptors in the brainstem of the ferret. Gastroenterology 121, 767-774 (2001).

Vo et al., Non-steroidal anti-inflammatory drugs for neuropathic pain: how do we explain continued widespread use? Pain 143, 169-171 (2009).

Walker et al., Pain modulation by release of the endogenous cannabinoid anandamide. Proc. Natl. Acad. Sci. U. S. A. 96, 12198-12203 (1999).

Wang et al., Evaluation of the MDR-MDCK cell line as a permeability screen for the blood-brain barrier. Int. J. Pharm. 288, 349-359 (2005).

Waszkielewicz et al., Evaluation of anticonvulsants for possible use in neuropathic pain. Curr. Med. Chem. 18, 4344-4358 (2011).

Wickerts et al., Coxibs: is there a benefit when compared to traditional non-selective NSAIDs in postoperative pain management? Minerva Anestesiol. 77, 1084-1098 (2011).

Wotherspoon et al., Peripheral nerve injury induces cannabinoid receptor 2 protein expression in rat sensory neurons. Neuroscience 135, 235-245 (2005).

Yu et al., A peripherally restricted cannabinoid receptor agonist produces robust anti-nociceptive effects in rodent models of inflammatory and neuropathic pain. Pain 151, 337-344 (2010).

Zhang et al., Induction of CB2 receptor expression in the rat spinal cord of neuropathic but not inflammatory chronic pain models. Eur. J. Neurosci. 17, 2750-2754 (2003).

Beltramo et al., "CB2 receptor-mediated antihyperalgesia: possible direct involvement of neural mechanisms," European Journal of Neuroscience, vol. 23, 1530-1538 (2006).

Clark et al., "Computational prediction of blood-brain barrier permeation," Annual Reports in Medical Chemistry, vol. 40, 403-415 (2005).

Dunham et al., "A Note on a Simple Apparatus for Detecting Neurological Deficit in Rats and Mice," Journal of the American Pharmaceutical Association, vol. 46, 208-209 (1957).

Gong et al., "Acute and subacute bronchial effects of oral cannabinoids," Clin. Pharmacol. Ther. vol. 35, 26-32 (1984).

Horvath et al., "The Endocannabinoid System and Plant-Derived Cannabinoids in Diabetes and Diabetic Complications," The American Journal of Pathology, vol. 180, 432-442 (2012).

Huffman, "The Search for Selective Ligands for the CB2 Receptor," Current Pharmaceutical Design, vol. 6, 1323-1337 (2000).

Idris, "Role of cannabinoid receptors in bone disorders: Alternatives for treatment," Drug News Perspect. vol. 21, 533-540 (2008).

Izzo et al., "Cannabinoids and the digestive tract," Handb. Exp. Pharmacol, 573-598 (2005).

Kandemirli et al., "Structure-Activity Relationships Investigation in a Mixed Series of Cannabinoids", Arzneim.-Forsch./Drug Res., vol. 52, No. 10, 731-739 (2002).

Pertwee, "Effects of Cannabinoids on Thermoregulation: A Brief Review," Marihuana '84 (ed. Harvey,D.J.), 263-277 (IRL Press, Oxford, 1985).

Reggio, "Pharmacophores for ligand recognition and activation/inactivation of the cannabinoid receptors," Current Pharmaceutical Design, vol. 9, 1607-1633 (2003).

Straiker et al., Localization of cannabinoid CB1 receptors in the human anterior eye and retina. Invest Ophthalmol. Vis. Sci. 40, 2442-2448 (1999).

Abrams et al., Cannabis in painful HIV-associated sensory neuropathy: a randomized placebo-controlled trial. Neurology. 68, 515-521 (2007).

Adam et al., Low brain penetrant CB1 receptor agonists for the treatment of neuropathic pain. Bioorg. Med. Chem. Lett. 22, 2932-2937 (2012).

Agarwal et al., Cannabinoids mediate analgesia largely via peripheral type 1 cannabinoid receptors in nociceptors. Nat. Neurosci. 10, 870-879 (2007).

Basavarajappa et al., Role of the endocannabinoid system in the development of tolerance to alcohol. Alcohol Alcohol. 40, 15-24 (2005).

Beaulieu, P. Effects of nabilone, a synthetic cannabinoid, on postoperative pain. Can. J. Anaesth. 53, 769-775 (2006).

Benito et al., Cannabinoid CB2 receptors in human brain inflammation. Br. J. Pharmacol. 153, 277-285 (2008).

Ben-Shabat et al., New cannabidiol derivatives: synthesis, binding to cannabinoid receptor, and evaluation of their antiinflammatory activity. J. Med. Chem. 49, 1113-1117 (2006).

Berman et al., Efficacy of two cannabis based medicinal extracts for relief of central neuropathic pain from brachial plexus avulsion: results of a randomised controlled trial. Pain 112, 299-306 (2004).

Bisogno et al., The endocannabinoid signalling system: biochemical aspects. Pharmacol. Biochem. Behav. 81, 224-238 (2005).

Brents et al., Monohydroxylated metabolites of the K2 synthetic cannabinoid JWH-073 retain intermediate to high cannabinoid 1 receptor (CB1R) affinity and exhibit neutral antagonist to partial agonist activity. Biochem. Pharmacol. 83, 952-961 (2012).

Brents et al., Phase I hydroxylated metabolites of the K2 synthetic cannabinoid JWH-018 retain in vitro and in vivo cannabinoid 1 receptor affinity and activity. PLoS. ONE. 6, e21917 (2011).

Bridges et al., The synthetic cannabinoid WIN55,212-2 attenuates hyperalgesia and allodynia in a rat model of neuropathic pain. Br. J. Pharmacol. 133, 586-594 (2001).

(56) References Cited

OTHER PUBLICATIONS

Brusberg et al., $CB_1$ receptors mediate the analgesic effects of cannabinoids on colorectal distension-induced visceral pain in rodents. J. Neurosci. 29, 1554-1564 (2009).

Carroll et al., Designer drugs: a medicinal chemistry perspective. Ann. N. Y. Acad. Sci. 1248, 18-38 (2012).

Chevaleyre et al., Endocannabinoid-mediated synaptic plasticity in the CNS. Annu. Rev. Neurosci. 29:37-76., 37-76 (2006).

Compton et al., Cannabinoid structure-activity relationships: correlation of receptor binding and in vivo activities. J. Pharmacol. Exp. Ther. 265, 218-226 (1993).

Costa et al., Repeated treatment with the synthetic cannabinoid WIN 55,212-2 reduces both hyperalgesia and production of pronociceptive mediators in a rat model of neuropathic pain. Br. J. Pharmacol. 141, 4-8 (2004).

Dworkin et al., Pharmacologic management of neuropathic pain: evidence-based recommendations. Pain 132, 237-251 (2007).

Ellis et al., Smoked medicinal cannabis for neuropathic pain in HIV: a randomized, crossover clinical trial. Neuropsychopharmacology 34, 672-680 (2009).

Ertl et al., Fast calculation of molecular polar surface area as a sum of fragment-based contributions and its application to the prediction of drug transport properties. J. Med. Chem. 43, 3714-3717 (2000).

Esfandyari et al., Effects of a cannabinoid receptor agonist on colonic motor and sensory functions in humans: a randomized, placebo-controlled study. Am. J. Physiol Gastrointest. Liver Physiol. 293, G137-G145 (2007).

Fride et al., (+)-Cannabidiol analogues which bind cannabinoid receptors but exert peripheral activity only. Eur. J. Pharmacol. 506, 179-188 (2004).

Fulp et al., Design and synthesis of cannabinoid receptor 1 antagonists for peripheral selectivity. J. Med. Chem. 55, 2820-2834 (2012).

Galiegue et al., Expression of central and peripheral cannabinoid receptors in human immune tissues and leukocyte subpopulations. Eur. J. Biochem. 232, 54-61 (1995).

Garcia Rodriguez et al., NSAID use selectively increases the risk of non-fatal myocardial infarction: a systematic review of randomised trials and observational studies. PLoS. ONE. 6, e16780 (2011).

Guerrero et al., Peripheral cannabinoids attenuate carcinoma-induced nociception in mice. Neurosci. Lett. 433, 77-81 (2008).

Hanus et al., HU-308: a specific agonist for CB(2), a peripheral cannabinoid receptor. Proc. Natl. Acad. Sci. U. S. A. 96, 14228-14233 (1999).

Herkenham et al., Cannabinoid receptor localization in brain. Proc. Natl. Acad. Sci. U. S. A. 87, 1932-1936 (1990).

Ibrahim et al., Activation of CB2 cannabinoid receptors by AM1241 inhibits experimental neuropathic pain: pain inhibition by receptors not present in the CNS. Proc. Natl. Acad. Sci. U. S. A. 100, 10529-10533 (2003).

Johnston et al., Triptans for the management of migraine. Drugs 70, 1505-1518 (2010).

Ligresti et al., Antitumor activity of plant cannabinoids with emphasis on the effect of cannabidiol on human breast carcinoma. J. Pharmacol. Exp. Ther. 318, 1375-1387 (2006).

Mitrirattanakul et al., Site-specific increases in peripheral cannabinoid receptors and their endogenous ligands in a model of neuropathic pain. Pain 126, 102-114 (2006).

Morlion, B. Pharmacotherapy of low back pain: targeting nociceptive and neuropathic pain components. Curr. Med. Res. Opin. 27, 11-33 (2011).

Notcutt et al., Initial experiences with medicinal extracts of cannabis for chronic pain: results from 34 'N of 1' studies. Anaesthesia 59, 440-452 (2004).

Oltmanns et al., Topical WIN55212-2 alleviates intraocular hypertension in rats through a CB1 receptor mediated mechanism of action. J. Ocul. Pharmacol. Ther. 24, 104-115 (2008).

Pacher et al., Modulation of the endocannabinoid system in cardiovascular disease: therapeutic potential and limitations. Hypertension. 52, 601-607 (2008).

Pertwee, R.G. Pharmacological actions of cannabinoids. Handb. Exp. Pharmacol.1-51 (2005).

Pertwee, R.G. The diverse CB1 and CB2 receptor pharmacology of three plant cannabinoids: delta9-tetrahydrocannabinol, cannabidiol and delta9-tetrahydrocannabivarin. Br. J. Pharmacol. 153, 199-215 (2008).

Pertwee, R.G. The ring test: a quantitative method for assessing the 'cataleptic' effect of cannabis in mice. Br. J. Pharmacol. 46, 753-763 (1972).

Porcella et al., The human eye expresses high levels of CB1 cannabinoid receptor mRNA and protein. Eur. J. Neurosci. 12, 1123-1127 (2000).

Potenzieri et al., Cannabinoid modulation of cutaneous Adelta nociceptors during inflammation. J. Neurophysiol. 100, 2794-2806 (2008).

Rahn et al., Activation of cannabinoid CB1 and CB2 receptors suppresses neuropathic nociception evoked by the chemotherapeutic agent vincristine in rats. Br. J. Pharmacol.(2007).

Rahn et al., Selective activation of cannabinoid CB2 receptors suppresses neuropathic nociception induced by treatment with the chemotherapeutic agent paclitaxel in rats. J. Pharmacol. Exp. Ther. 327, 584-591 (2008).

Richardson et al., SR 141716A, a cannabinoid receptor antagonist, produces hyperalgesia in untreated mice. Eur. J. Pharmacol. 319, R3-R4 (1997).

Rinaldi-Carmona et al., SR141716A, a potent and selective antagonist of the brain cannabinoid receptor. FEBS Lett. 350, 240-244 (1994).

Robson, P. Therapeutic aspects of cannabis and cannabinoids. Br. J. Psychiatry 178, 107-115 (2001).

Thakor et al., Increased peripheral nerve excitability and local NaV1.8 mRNA up-regulation in painful neuropathy. Mol. Pain 5:14., 14 (2009).

Welch et al., Differential blockade of the antinociceptive effects of centrally administered cannabinoids by SR141716A. J. Pharmacol. Exp. Ther. 286, 1301-1308 (1998).

Wilsey et al., A randomized, placebo-controlled, crossover trial of cannabis cigarettes in neuropathic pain. J. Pain. 9, 506-521 (2008).

Xu et al., Pharmacological characterization of a novel cannabinoid ligand, MDA19, for treatment of neuropathic pain. Anesth. Analg. 111, 99-109 (2010).

Grosser, et al., "Chapter 34: Anti-inflammatory, Antipyretic, and Analgesic Agents; Pharmacotherapy of Gout," Goodman & Gilman: The Pharmacological Basis of Therpeutics, 12th Edition, Jan. 10, 2011, 52 pages.

O'Donnell et al., "Chapter 15: Drug Therapy of Depression and Anxiety Disorders," Goodman & Gilman's: The Pharmacological Basis of Therapeutics, 12th Edition, Jan. 10, 2011, 13 pages.

\* cited by examiner

PERIPHERALLY-ACTING CANNABINOID RECEPTOR AGONISTS FOR CHRONIC PAIN

CLAIM OF PRIORITY

This application is a National Stage of International Application No. PCT/US2013/051369, filed Jul. 19, 2013, which claims priority to U.S. Provisional Application No. 61/673,904, filed Jul. 20, 2012, and to U.S. Provisional Application No. 61/792,337, filed Mar. 15, 2013, each of which is incorporated by reference in its entirety.

STATEMENT OF GOVERNMENT SUPPORT

This invention was made with Government support under Grant No. DA023163 awarded by the National Institutes of Health. The Government has certain rights in this invention.

FIELD OF THE INVENTION

Indene-based or Indole-based peripherally-acting cannabinoid receptor agonists and uses thereof.

BACKGROUND OF THE INVENTION

Synthetic and naturally occurring cannabinoids are a focus of strong social, legal and medical controversy concerning their therapeutic utility, yet studies show that cannabinoids reduce the symptoms of hyperalgesia and allodynia associated with persistent pain of inflammatory and neuropathic origin in humans and animals. Furthermore, cannabinoids are effective in alleviating chronic pain symptoms after prolonged repeated treatment, unlike opioids, which have only limited effectiveness. A major impediment to the widespread use of cannabinoid analgesics has been their central nervous system (CNS)-mediated psychotropic side effects. In addition, there are various other conditions where selective activation (or blockade) of peripheral cannabinoid receptors could prove to be of clinical benefit.

Cannabinoid Receptors

The targets of the antinociceptive cannabinoids may be defined by the distribution of two cloned subtypes of cannabinoid receptors, CB1R and CB2R. These are members of the superfamily of G protein-coupled receptors (GPCRs); both CB1R and CB2R are coupled to $G_{i/o}$ proteins. Another recent addition to the cannabinoid receptor family is the G protein-coupled receptor, GPR55, which couples to $G_{\alpha 11-13}$. CB1R is actually the most abundant central nervous system (CNS) GPCR expressed at high levels in the hippocampus, cortex, cerebellum and basal ganglia[1,2]. CB1R activation leads to inhibition of adenylyl cyclase, blockade of voltage-gated $Ca^{2+}$-channels and activation of inwardly-rectifying $K^+$-channels. Central CB1Rs are also localized in regions involved in pain transmission and modulation, specifically in the spinal dorsal horn and periaqueductal gray. In the forebrain, ultrastructural studies have demonstrated a high degree of CB1R localization to presynaptic terminals of cholecystokinin-containing inhibitory interneurons, consistent with the ability of CB1R agonists to decrease evoked release of γ-aminobutyric acid (GABA). Presynaptic terminals of glutamatergic fibers in the hippocampus and cerebellum also express CB1Rs, albeit at much lower levels than in GABAergic neurons. These form the anatomical basis for the well-known ability of CB1R agonists to decrease excitatory glutamatergic neurotransmission in these brain regions. In the basal ganglia, CB1Rs are produced in and transported to the terminals of GABAergic medium-sized spiny neurons of the dorsal and ventral striatum, resulting in a dense CB1R-positive innervation of pallidal and nigral structures. CB1Rs were also localized to the glutamatergic terminals of corticostriatal neurons, and functional studies demonstrated that their activation leads to decreased glutamate release from corticostriatal inputs. In the brainstem, CB1Rs are expressed at relatively low levels within medullary respiratory control centers[1], but are highly expressed in axon terminals within medullary nuclei which control emesis, such as the area postrema[4]. This distribution is in agreement with the relative lack of respiratory effects and the potent antiemetic actions of cannabinoids[5]. Since the chemoreceptor trigger zone of the area postrema lies outside the blood-brain barrier, activation of CB1Rs in this area by cannabinoids that do not penetrate the CNS should produce antiemetic actions without CNS side effects.

In the peripheral nervous system, CB1Rs have been detected in dorsal root ganglion (DRG) neurons of heterogeneous size, with variable degrees of CB1Rs mRNA and protein localization to different sensory neuron subtypes. Thus, several groups reported predominant CB1R localization to large-diameter non-nociceptive neurons, while others localized CB1Rs primarily to small-diameter nociceptors. By contrast, CB1Rs were detected in the majority (89%) of DRG sensory neurons with similar degree of localization in nociceptor and non-nociceptor populations[6]. Axoplasmic flow of CB1Rs has been demonstrated in peripheral sensory axons, implying transport to terminals where cannabinoids are presumed to produce their antinociceptive effects. Immunohistochemical studies also revealed CB1R immunoreactivity in both small unmyelinated and large myelinated nerve fiber bundles in the human skin. These studies also demonstrated CB1Rs in human macrophages, mast cells, sebaceous cells and keratinocytes. The localization of CB1Rs on the central terminals of primary afferents remains controversial, in part because ultrastructural studies failed to detect CB1Rs on these terminals in rats and primates.

CB1Rs have also been localized to various neurons of the gastrointestinal (G-I) tract in different species, including humans[7,8]. Virtually all cholinergic sensory neurons, interneurons and motoneurons in myenteric ganglia express CB1R in close association with synaptic protein labeling. This differential distribution agrees with the inhibitory actions of cannabinoids on G-I motility and secretion[7,]. Pharmacological studies have also localized CB1Rs to presynaptic terminals of postganglionic sympathetic neurons, where they are thought to mediate depressant effects on sympathetic outflow by inhibiting noradrenaline release. The presence of CB1Rs was detected in endothelial cells of various vascular beds; these likely contribute to the vasodilatory actions of CB1R agonists. CB1Rs are expressed in the various structures of the human eye[9-10], with particularly high levels of expression in the ciliary body[10]. Selective activation of CB1Rs, but not CB2Rs decreases intraocular pressure[11]. However, the precise mechanisms by which cannabinoids decrease intraocular pressure have yet to be elucidated. CB1R transcripts are also detected in human spleen, tonsils and peripheral blood leukocytes, although at levels much lower than those found in the brain.

By contrast, CB2Rs were initially localized and are most highly expressed by immunocompetent cells of the spleen, thymus and various circulating immune cell populations[12,13]. While not without controversy, pharmacological studies have suggested, and molecular and immunocytochemical studies have later confirmed localization of CB2R in both peripheral and CNS neurons[14,15]. However, CB2R transcripts in the normal brain are present at much lower levels than CB1R transcripts. It is noteworthy that in contrast to the predominant presynaptic axon terminal location of CB1Rs, CB2Rs appear to localize to the cell bodies and dendrites of central and peripheral neurons. Although CB2Rs couple to $G_{i/o}$ proteins and inhibit adenylyl cyclase, they do not couple to inhibition of voltage-gated $Ca^{2+}$-channels or activation of $K^+$-channels; this may account for the lack of significant psychotropic effects upon administration of CB2R-selective agonists[16,17]. The physiological role of CB2Rs in central neurons is presently unclear; however administration of CB2R-selective ligands or direct intracerebroventricular administration of CB2R antisense oligonucleotides does modify behavior. CB2Rs were also localized with CB1Rs to the endothelial cells of human brain capillaries where they were proposed to play a role in regulation of cerebrovascular blood flow and blood-brain barrier permeability. In keeping with the immunomodulatory role of CB2Rs, brain and spinal cord microglia (the only hemopoietic lineage cell type in the CNS) are endowed with CB2Rs. In addition, GPR55, a novel cannabinoid receptor which is present both in brain and the periphery, may account for some of the actions of cannabinoids by activating signaling pathways quite distinct from those used by CB1/CB2Rs. The broad expression of the three cannabinoid receptors in the CNS and various visceral organs implies involvement in a variety of physiological processes which are subject of intensive investigations.

Endocannabinoids and their Metabolism

The endogenous lipid cannabinoids which bind to their receptors cannot be sequestered in vesicles and are therefore synthesized on demand and immediately released by neuronal tissues. For example, N-arachidonoylethanolamine (anandamide, AEA) is mainly produced by a two-step enzymatic pathway involving calcium-dependent transacylase and phospholipase D. Then, AEA either diffuses or is actively transported into cells and is rapidly degraded by the membrane-bound fatty acid amide hydrolase (FAAH) to arachidonic acid. Another endocannabinoid, 2-arachidonoyl glycerol (2-AG) is synthesized via the diacylglycerol lipase (DAGL)-mediated hydrolysis of diacylglycerol and metabolized primarily by monoacylglycerol lipase (MAGL). There is also evidence that FAAH and two recently characterized serine hydrolases (ABHD6 and ABHD12) may contribute to 2-AG metabolism. Interestingly, FAAH is mainly a postsynaptic enzyme whereas MAGL is localized to presynaptic axon terminals, suggesting possible differences in the functional roles for AEA and 2-AG. The brain levels of 2-AG are at least two orders of magnitude higher than AEA. Both AEA and 2-AG are cleared by a high-affinity, selective transporter, which has been characterized biochemically but not molecularly. The biochemistry and metabolism of AEA and 2-AG, as well as other less-well studied endocannabinoids has been reviewed[18].

Endocannabinoids and Synaptic Plasticity

The postsynaptic localization of the endocannabinoid production and transport machinery versus the presynaptic location of CB1Rs led to the current and widely accepted view that brain endocannabinoids are synthesized following excitatory activation in postsynaptic neurons yet act as retrograde messengers at presynaptic terminals to decrease the release of various neurotransmitters. The endocannabinoid-mediated plasticity involves at least four different types of transient- and long-lasting synaptic depression, which is found at both excitatory and inhibitory synapses in many different brain regions[19]. In addition, endocannabinoids can modify the induction of non-endocannabinoid-mediated forms of synaptic plasticity[19]. The widespread involvement of the endocannabinoid system in synaptic plasticity implies a major role in learning and memory and consequently, behavior.

Antinociceptive Actions of Cannabinoids

Endocannabinoids such as AEA, naturally occurring $\Delta^9$-tetrahydrocannabinol ($\Delta^9$-THC), and synthetic cannabinoids such as WIN 55,212-2 or CP 55,940 inhibit responses to noxious thermal and mechanical stimulation in a variety of tests[20-25]. Blockade of peripheral or central CB1Rs leads to hyperalgesia, suggesting tonic activation of CB1Rs by endocannabinoids[26-29]. Other studies determined that cannabinoids are also effective in reducing thermal and mechanical hyperalgesia and mechanical allodynia induced by peripheral inflammation[30-32] and peripheral nerve injury in rodents[33]. Similarly, chronic neuropathic pain symptoms in humans are alleviated by cannabinoids[34-39]. Cannabinoids are effective in alleviating neuropathic pain symptoms after prolonged repeated treatment[40,41], unlike opioids, which have only limited effectiveness[42-44]. The antinociceptive (analgesic) and antihyperalgesic effects of cannabinoids were initially thought to be mediated largely by CB1Rs since they are blocked by the selective CB1R antagonist SR 141716A[28, 31, 45, 46].

Cannabinoid Actions on Motor Control and Cognition

In addition to analgesic effects, acute consumption of *cannabis* reversibly impairs a variety of cognitive and performance tasks, including memory and learning[47]. Activation of central CB1Rs by cannabinoids such as $\Delta^9$-THC or AEA produces other complex effects on behavior unique to this class of compounds: at low doses a mixture of stimulatory and depressant effects is observed, while at higher doses central depression predominates[48,49]. Catalepsy, motor deficits and hypothermia are among the effects observed after administration of centrally-acting cannabinoids[48-50]. These properties, which appear in large part mediated by CB1Rs, have greatly limited the clinical use of cannabinoids for the treatment of chronic pain states. At the same time, the increased understanding of CB1R function in the CNS has prompted the evaluation of CB1R ligands for treatment in various other disorders, including: psychoses, obesity, multiple sclerosis, stroke, brain trauma, drug addiction and movement disorders[51-54].

The synthesis of CB2R-selective agonists such as HU308 and AM1241 was a major development because these compounds produced antinociceptive and antihyperalgesic effects in transient and persistent pain states by activating what was at the time was thought to be essentially a peripheral cannabinoid receptor[16,55]. Importantly, these compounds lack the type of side effects associated with activation of central CB1Rs, which effectively renewed interest in the development of peripherally-active cannabinoid-based analgesics.

Endocannabinoid System Alterations in Inflammatory and Neuropathic Pain States

It was demonstrated that the antihyperalgesic effectiveness of centrally-administered synthetic cannabinoid WIN55,212-2 is greater after induction of rodent hindpaw inflammation than its antinociceptive effects in non-inflamed hindpaws[30]. Another study showed that endocannabinoid (AEA) levels in the periaqueductal gray increase in response to peripheral inflammation[56]. Since then many studies have demonstrated that both CB1Rs and CB2Rs undergo increased expression during inflammation and after development of peripheral nerve injury-induced painful neuropathies, reviewed in[3]. Such transcription-driven increases in cannabinoid receptors were demonstrated both in the peripheral tissues and the CNS. Increases in the tissue levels of endocannabinoids have also been demonstrated in inflammatory and neuropathic pain states. For example, we demonstrated nerve injury-induced increases in the levels of endocannabinoids within sensory ganglia[6]. Presently it is unknown whether increased endocannabinoid levels are due to their increased 'on-demand' synthesis by hyperexcitable neurons or to decreases in the activity of enzymes which metabolize endocannabinoids.

The increases in cannabinoid receptor expression result in increased potency or efficacy of the exogenously applied cannabinoids, depending on whether the ligand is a full (e.g., WIN55,212-2) or a partial agonist (e.g., $\Delta^9$-THC)[57]. It is also likely that increased cannabinoid receptor expression contributes to the effectiveness of cannabinoids in providing relief from painful neuropathy symptoms after repeated administration. By contrast, several studies demonstrated that morphine has only limited effectiveness in alleviating peripheral neuropathy symptoms, possibly due to the decreased expression of peripheral opioid receptors[42-44]. In addition, chronic opioid treatment leads to considerable analgesic tolerance and development of hyperalgesic effects[58-59] which have led to the failure of opioid therapy to successfully treat chronic pain populations[60]. By contrast, recent clinical studies have reaffirmed that long-term treatment with cannabinoids for symptomatic relief of peripheral neuropathy symptoms does not result in any appreciable decrement in clinical effectiveness after long-term administration[38].

Homeostatic Role of the Endocannabinoid System

In addition to inflammatory and neuropathic pain states, it appears that any pathological condition that involves an inflammatory response, be it injury-, foreign organism- or autoimmune-generated, results in the up-regulation of the endocannabinoid system. Thus, alterations (usually increases) in cannabinoid receptors and/or their endogenous ligands have been observed in temporal lobe epilepsy, alcoholism, brain ischemia, endometritis, pancreatitis, and other types of injury[3]. Also, injury symptomatology is exacerbated in the presence of CB1R or CB2R antagonists or in mice with genetic deletions of CB1R and CB2R. While the specific alterations appear to depend on the type of injury/pathology, an overall emerging view is that the up-regulation of the endocannabinoid system is the organism's compensatory mechanism designed to alleviate the negative consequences of tissue injury and facilitate repair[11,52]. Nevertheless, there are several clinically relevant situations where increases in CB1R expression may have an adverse effect. In these conditions, selective blockade of peripheral CB1Rs could prove to be of clinical benefit. Also, mice with a genetic deletion of GPR55 were shown not to develop either inflammatory- or nerve injury-induced hyperalgesia, suggesting that selective GPR55 antagonists may also be of utility for treating inflammatory or neuropathic pain.

Actions at Non-Cannabinoid Receptors

In addition to the diverse physiological effects of cannabinoid receptor activation, certain cannabinoids have effects at other targets. For example, anandamide administration in CB1R−/− mice still produces cannabinomimetic effects in various behavioral tests. While some of these effects could be ascribed to actions at CB2Rs or GPR55Rs, others may be due to activation of non-cannabinoid receptors or to receptor-independent interactions with membrane ion channels and intracellular second messenger systems. In particular, several endogenous and synthetic cannabinoids have demonstrated effects at transient receptor potential (TRP) receptors. Certain TRP receptors (e.g. TRPV1) are highly expressed in nociceptors where they play an important role in detection of nociceptive signals and nociceptor sensitization in inflammatory and neuropathic pain states.

Several studies demonstrated that near physiological concentrations of AEA produce local vasodilation, vas deferens relaxation, and excitation of the central terminals of sensory afferents, all via TRPV1 receptor activation. Such studies led to the idea that endocannabinoids acting via TRPV1 may contribute to nociception and hyperalgesia, reviewed by[61, 62]. Indeed, AEA was implicated in the inflammatory response of certain tissues. Thus, toxin A-induced inflammation and edema of the ileum was shown to be dependent on activation of TRPV1 receptors by endogenous AEA. Similar findings were obtained in cyclophosphamide-induced bladder hyperreflexia and cystitis. It was also shown that inflammatory mediators can convert anandamide into a potent activator of TRPV1 receptors, possibly via receptor sensitization. On the other hand, many studies showed that cannabinoids require micromolar levels to activate TRP receptors, whereas activation of antinociceptive cannabinoid receptors occurs at nanomolar levels. Thus, with the possible exception of N-arachidonoyl dopamine (nm activation of TRPV1 receptors), both endogenous and exogenous cannabinoids which possess TRP activity act as partial agonists at TRP receptors. In addition, cannabinoid receptor-mediated activation of calcineurin results in TRPV1 receptor desensitization. Recent studies have also demonstrated that selective activation of CB2Rs on human sensory neurons blocks capsaicin-induced inward currents and cytoplasmic $Ca^{2+}$ elevation via inhibition of adenylyl cyclase. Collectively, these studies help explain why exogenous cannabinoids produce analgesic and antihyperalgesic effects rather than pronociceptive effects after local peripheral or systemic administration[3].

Dissociating Effects of Peripheral and Central Cannabinoid Receptor Activation

Early studies have assumed a central action of cannabinoids based on the high degree of CB1R expression in the brain, including various sites associated with pain signal transmission and modulation. Subsequently, multiple studies with genetically engineered mice with global deletion of CB1Rs have confirmed their role in cannabinoid-induced analgesia, but did not localize their actions to peripheral or central receptors. Evidence for important peripheral sites of cannabinoid analgesic effects came from studies where local administration of cannabinoids into inflamed tissue attenuated hyperalgesia and allodynia via peripheral CB1Rs, at doses which produced minimal centrally-mediated side effects[105, 173, 174]. Peripheral CB1R activation was also shown to reduce mechanical activation of A-δ nociceptors from inflamed but not from non-inflamed skin. Similarly, local activation of peripheral CB1Rs attenuates hyperalgesia produced by thermal injury, nerve injury, and cancer (reviewed in[3]).

The crucial role of peripheral cannabinoid receptors in the antihyperalgesic actions of systemically administered cannabinoids was demonstrated using conditional deletion of CB1Rs located on nociceptive primary afferent neurons[70]. In these conditional peripheral CB1R knockout mice, the antihyperalgesic effects of systemically-administered cannabinoids were nearly completely lost in models of carrageenan-induced inflammation and sciatic nerve injury-induced neuropathy. By contrast, the effects of central CB1R activation were retained in the conditional knockouts, but lost in the global CB1R-null mice[70].

Medications for Acute Inflammatory and Post-Operative Pain

Non-Steroidal Anti-Inflammatory Analgesics

Various non-steroidal anti-inflammatory analgesics (NSAIAs) which include both non-selective and selective cyclooxygenase-2 enzyme (COX-2) inhibitors have been developed. These include 1) salicylic acid derivatives (e.g., aspirin); 2) the aniline derivative, acetaminophen; 3) phenylpropionic acid derivatives (e.g., ibuprophen); 4) anthranilic acid derivatives (e.g., mefenamic acid); 5) selective COX-2 inhibitors (e.g., celecoxib). Together, NSAAs provide pain relief without appreciable psychotropic effects and have little, if any, abuse potential. Toxicity of non-selective COX-2 inhibitors is mainly due to interference with the production of certain prostaglandins, prostacyclins and thromboxanes which provide important homeostatic functions such as gastro-intestinal (G-I) mucosal protection, platelet aggregation and vasodilation[71]. Such side effects are generally milder with selective COX-2 inhibitors[72]. However, chronic use of selective COX-2 inhibitors significantly increases the risk of heart attack and stroke[72].

Opioid Analgesics

Numerous naturally occurring (e.g., codeine), semi-synthetic (e.g., hydrocodone) and synthetic (e.g., meperidine) opioid analgesics are in use. Opioid analgesics have little anti-inflammatory activity, but they act on the motivational-affective component of pain. They also provide potentially useful sedative and anxiolytic effects. Toxicity includes respiratory depression (which increases with analgesic potency), nausea and vomiting, constipation and miosis. In addition, tolerance and dependence are characteristic of all opioid analgesics; this contributes to their abuse potential.

Together, NSAIAs and opioid analgesics represent the mainstay treatment of acute inflammatory and post-operative pain.

Medications for Treating Chronic Pain

There are several different types of chronic pain that may be distinguished. Some, like rheumatoid arthritis and certain types of cancer, have a significant inflammatory component. By contrast, chronic pain of neuropathic origin (e.g., postherpetic neuralgia, diabetic neuropathy) usually does not involve chronic inflammation, pain symptoms mostly result from aberrant input or processing of nociceptive signals. Certain types of headache syndromes (e.g., migraine headaches) may be classified as chronic intermittent and have variable etiologies that may include an inflammatory component. Current treatments of different types of chronic pain are geared towards decreasing inflammation (if it exists) and maximizing pain relief while minimizing side effects associated with each particular drug type. Unfortunately, this has been a difficult goal to achieve and all of the current treatments for chronic pain, particularly pain of neuropathic origin, have significant side effects which limit their usefulness.

Non-Steroidal Anti-Inflammatory Analgesics

Chronic treatment of rheumatoid arthritis with non-selective COX-2 inhibitors erodes the G-I mucosa and leads to G-I ulcerations. These side effects are generally milder with selective COX-2 inhibitors[72]. However, chronic use of selective COX-2 inhibitors significantly increases the risk of heart attack and stroke[72-75]. NSAIAs in general have little effectiveness in alleviating pain of neuropathic origin[76-78].

Opioid Analgesics

Chronic treatment with opioid analgesics leads to the development of tolerance and dependence, as well as the development of opioid-induced pain[79-81]. Side effects of symptomatic treatment of migraine headaches with triptan medications (e.g., sumatriptan) include: nausea, vomiting, fatigue, dizziness, vertigo, paraesthesias, sleepiness and rebound headaches[82].

Tricyclic Antidepressants

Tricyclic antidepressants (e.g., imipramine) have a small but significant effect of decreasing chronic pain symptoms[83]. However, even at low therapeutic doses there are significant CNS side effects of lethargy and clumsiness, peripheral side effects of dry mouth, epigastric distress, postural hypotension, tachycardia and increased susceptibility to life-threatening cardiac arrhythmias[84].

Anticonvulsants

Various anticonvulsant drugs (e.g., carbamazepine, gabapentin, topiramate) are prescribed for treatment of various chronic pain conditions[85-88]. The CNS side effects of these drugs severely limit their therapeutic effectiveness.

Cannabinoids

Chronic neuropathic pain symptoms in humans are alleviated by cannabinoids[89-94]. Moreover, long-term treatment with cannabinoids for symptomatic relief of peripheral neuropathy symptoms does not result in any appreciable decrement in clinical effectiveness after long-term administration[92, 93, 95]. However, a major impediment to the widespread use of cannabinoid analgesics has been their CNS-mediated side effects which include cognitive impairment, motor incoordination and hypothermia.

Strategies for Peripheral Cannabinoid Receptor Targeting

Considerable experimental and clinical evidence points to the homeostatic role of the endocannabinoid system in ameliorating the negative consequences of tissue injury. Therapeutic targeting of the peripheral cannabinoid receptors could provide relief of injury symptoms and speed up tissue repair, while minimizing the side effects associated with activation of central cannabinoid receptors.

One approach already taken was the development of CB2R-selective ligands. Given the demonstrations of CB2Rs on human sensory nerve fibers and the increased expression of CB2Rs within human and rat sensory neurons after inflammation and peripheral nerve injury[96-97], CB2R-selective agonists promise to become an important treatment option for inflammatory and neuropathic pain states[98]. CB2R-selective agonists are also being considered for the treatment of myocardial ischemia and atherosclerosis[99].

Many CB2R-selective ligands have been developed[100-101], although brain-impermeant analogs are not being emphasized because of the limited localization of CB2Rs in the CNS under normal conditions as well as their increased central expression in neuropathic pain states[96, 103] and in autoimmune disorders[104]. A potential concern with administration of selective CB2R ligands for the treatment of chronic pain symptoms is excessive suppression of the immune system, which could make them unsuitable as therapeutics in patients with compromised immune systems.

An alternative strategy is to develop selective CB1R agonists which do not penetrate the blood-brain barrier, thereby providing pain relief without the side effects associated with central CB1R activation. Indeed, one compound with a dual CB1R/CB2R agonist profile (~170-fold preference for CB1R over CB2R) and restricted CNS permeability was reported to possess antihyperalgesic properties without appreciable central side effects[105]. Another study demonstrated this compounds' effectiveness against colorectal distention-induced visceral pain; this action was blocked by CB1R but not CB2R antagonists[106]. Several other CB1R ligands were reported to exhibit limited brain penetration and few psychotropic side effects[107]. However, some derivatives turned out to have little activity at CB1Rs or CB2Rs, their effects appear to be mediated through other yet to be defined mechanisms[108]. Other new derivatives may bind CB1Rs, but may exhibit antagonistic activity at these receptors[109]. More recently, two other studies reported the development of low brain penetrant CB1R agonists for the treatment of neuropathic pain[110,111]. In both instances, the ligands possessed better analgesic to side-effect ratio profiles compared to the classical cannabinoid ligand WIN 55,212-2[110, 111]. However, some central effects could still be observed with the AstraZeneca compound which has the lowest brain/plasma concentration ratio (~0.05)[111], while the Merck compound with its higher brain/plasma concentration ratio (~0.22) would be expected to have more substantial centrally-mediated side effects. Thus, development of peripherally-acting CB1R agonists continues to represent an important goal. Such brain-impermeant analgesics would still be expected to produce side effects of peripheral CB1R activation such as constipation, hypotension, and possibly weight gain. There is also a potential concern for the development of tolerance to CB1R agonists during prolonged treatment. However, in clinical trials of *cannabis* preparations for neuropathic pain treatment, such side effects were well-tolerated and there was no evidence for development of analgesic tolerance with long-term treatment[92,93,95].

The foregoing summary, as well as the following detailed description of the invention, will be better understood when read in conjunction with the appended figures. For the purpose of illustrating the invention, the figures demonstrate embodiments of the present invention. It should be understood, however, that the invention is not limited to the precise arrangements, examples, and instrumentalities shown.

DETAILED DESCRIPTION

Definitions

Figure 1:
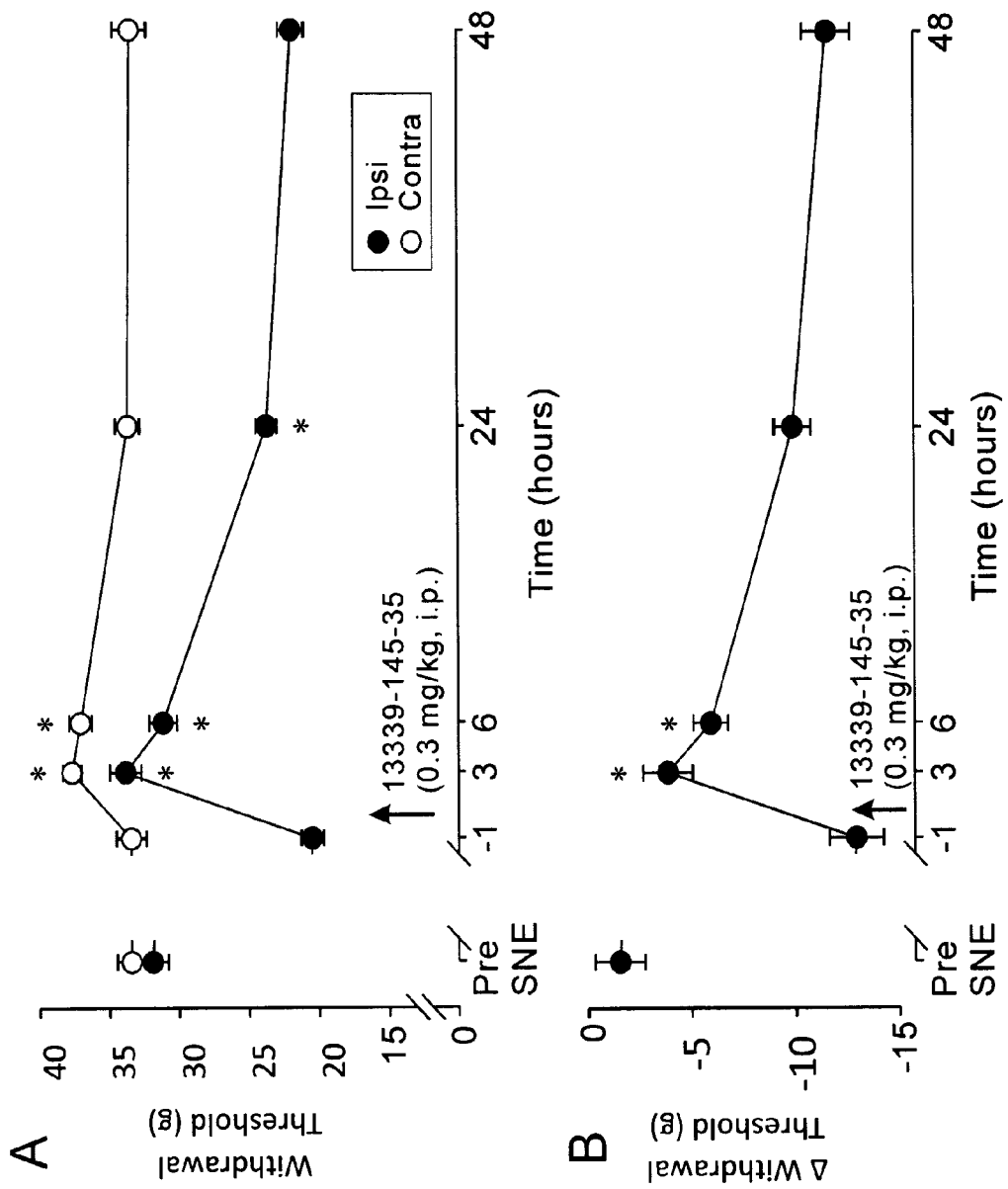
FIG. 1 shows the effect of 13339-145-35 on SNE-induced mechanical allodynia. A: Graph of withdrawal thresholds to mechanical stimulation of rat hindpaws ipsilateral and contralateral to SNE injury at 1 hr before and 3, 6, 24 and 48 hrs after 13339-145-35 injection. Data are presented as mean±SEM, n=7 rats). Note the small, but significant increases in contralateral withdrawal thresholds. B: Graph of differences in hindpaw withdrawal thresholds (ipsilateral-contralateral) before and after 13339-145-35 administration. *, $p<0.05$ from pre-drug values (one-way ANOVA).

As used herein, "agent" is a non-peptide, small molecule compound according to the invention.

By "control" is meant a standard or reference condition.

By "disease" is meant any condition or disorder that damages or interferes with the normal function of a cell, tissue, organ or subject.

By "effective amount" is meant the amount of an agent required to ameliorate the symptoms of a disease relative to an untreated subject. The effective amount of an active therapeutic agent for the treatment of a disease or injury varies depending upon the manner of administration, the age, body weight, and general health of the subject. Ultimately, the attending clinician will decide the appropriate amount and dosage regimen.

By "modifies" is meant alters. An agent that modifies a cell, substrate, or cellular environment produces a biochemical alteration in a component (e.g., polypeptide, nucleotide, or molecular component) of the cell, substrate, or cellular environment.

As used herein, the terms "prevent," "preventing," "prevention," "prophylactic treatment" and the like refer to reducing the probability of developing a disorder or condition in a subject, who does not have, but is at risk of or susceptible to developing a disorder or condition.

By "subject" is meant a mammal, including, but not limited to, a human or non-human mammal, such as a bovine, equine, canine, ovine, or feline.

As used herein, the terms "treat," treating," "treatment," "therapeutic" and the like refer to reducing or ameliorating a disorder and/or symptoms associated therewith. It will be appreciated that, although not precluded, treating a disorder or condition does not require that the disorder, condition or symptoms associated therewith be completely eliminated.

As used herein, the terms "reduce," and "reducing" when used in the context of a method of treatment mean decreasing the extent of or amount of, relative to a condition where no treatment is administered.

As used herein, the term "about" when referring to a measurable value such as an amount, a temporal duration, and the like, is meant to encompass variations of ±0.20% or ±10%, more preferably ±5%, even more preferably ±1%, and still more preferably ±0.1% from the specified value, as such variations are appropriate to perform the disclosed methods.

The terms "alkyl" used alone or as part of a larger moiety (i.e. "alkoxy," "hydroxyalkyl," "alkoxyalkyl," and "alkoxycarbonyl") include both straight and branched chains containing one to ten carbon atoms (i.e. 1, 2, 3, 4, 5, 6, 7, 8, 9, or 10 carbon atoms), as well as cyclic structures such as cyclopropyl and cyclobutyl. Examples of alkyl groups include methyl (Me), ethyl (Et), propyl (Pr) (including n-propyl ($^n$Pr or n-Pr), isopropyl ($^i$Pr or i-Pr) and cyclopropyl ($^c$Pr or c-Pr)), butyl (Bu) (including n-butyl ($^n$Bu or n-Bu), isobutyl ($^i$Bu or i-Bu), tert-butyl ($^t$Bu or t-Bu) and cyclobutyl ($^c$Bu or c-Bu)), pentyl (Pe) (including n-pentyl) and so forth. Alkyl groups also include mixed cyclic and linear alkyl groups, such as cyclopentylmethyl, cyclopentylethyl, cyclohexylmethyl, etc., so long as the total number of carbon atoms is not exceeded.

The term "alkoxy" refers to an —O-alkyl radical, such as, for example —O-Me, —O-Et, —O—Pr, and so on.

The term "hydroxyalkyl" refers to an alkyl group substituted with one or more hydroxyl, such as, for example, hydroxymethyl, 1-hydroxyethyl, 2-hydroxyethyl, 1,2-dihydroxyethyl, and so forth. The term "thioalkyl" refers to an —S-alkyl group, such as, for example, example —S-Me, —S-Et, —S-Pr.

The term "haloalkyl" means alkyl, substituted with one or more halogen atoms, such as trifluoromethyl, chloromethyl, 2,2,2-trifluoroethyl, 1,1,2,2,2,-petanfluoroethyl, and so on.

The term "aminoalkyl" means alkyl, substituted with an amine group ($NH_2$), such as, for example, aminomethyl, 1-aminoethyl, 2-aminoethyl, 3-aminopropyl and so forth.

The term "alkoxyalkyl" refers to an alkyl group, substituted with an alkoxy group, such as, for example, methoxymethyl, ethoxymethyl, methoxyethyl, and so forth.

As used herein, the term "alkylaminoalkyl" refers to an alkyl group substituted with an alkylamine group, such as, for example, N-methylaminomethyl, N,N-dimethylaminomethyl, N,N-methylpentylaminomethyl, 2-(N-methylamino) ethyl, 2-(N,N-dimethylamino)ethyl, and so forth.

The term "halogen" or "halo" means F, Cl, Br, or I.

The term "nitro" means (—$NO_2$).

The term "amine" or "amino" used alone or as part of a larger moiety refers to unsubstituted (—$NH_2$). The term "alkylamine" refers to mono- (—NRH) or di-substituted (—$NR_2$) amine where at least one R group is an alkyl substituent, as defined above. Examples include methylamino (—$NHCH_3$), dimethylamino (—$N(CH_3)_2$). As used herein, the term "tertiary amine" or "tertiary amino" means an amine-containing moiety where the nitrogen atom has three non-hydrogen substituents. "Amino" also includes quaternary amines (—$NR_3^+$) bearing a permanent positive charge, and associated with a suitable counterion. The counterion may be any suitable counter ion, including halide (chloride, bromide, iodide) or sulfonate (methanesulfonate, benzenesulfonate, toluenesulfonate, trifluoromethylsulfonate). Examples include trialkylammonium (e.g. triethylammonium) substituents having three alkyl groups on the amine substituent.

The term "cycloamino" used alone or as part of a larger moiety refers to a disubstituted amine (—$NR_2$), where the two R groups join to form a 3, 4, 5, 6, 7, or 8 membered monocyclic ring, or bicyclic ring having up to fourteen atoms or tricyclic ring system having up to fourteen atoms. The ring may be saturated or unsaturated, but not aromatic. The ring formed by the two R groups in the cycloamine substituent substitutent may be fused to an aromatic ring in a bicyclic or tricyclic system. The ring may include one or more additional heteroatoms, including N, S, O, P, or Si. Examples include morpholine, thiomorpholine, pyrrolidine, azetidine, piperidine, azepane, and so forth. "Cycloamino" also includes cycloammonium substituents (—$NR_3^+$) having an additional substituent on the nitrogen atom, producing a permanent positive charge. The additional substituent on the nitrogen is an alkyl substituent having 1, 2, 3, or 4 carbon atoms. A counterion is associated with the positive charge. The counterion may be any suitable counterion, including halide (chloride, bromide, iodide) or sulfonate (methanesulfonate, benzenesulfonate, toluenesulfonate, trifluoromethylsulfonate).

The term "arylamine" refers to a mono (—NRH) or di-substituted (—$NR_2$) amine, where at least one R group is an aryl group as defined below, including, for example, phenylamino, diphenylamino, and so forth.

The term "heteroarylamine" refers to a mono (—NRH) or di-substituted (—$NR_2$) amine, where at least one R group is a heteroaryl group as defined below, including, for example, 2-pyridylamino, 3-pyridylamino and so forth.

The term "aralkylamine" refers to a mono (—NRH) or di-substituted (—$NR_2$) amine, where at least one R group is an aralkyl group, including, for example, benzylamino, phenethylamino, and so forth.

The term "heteroaralkylamine" refers to a mono (—NRH) or di-substituted (—NR$_2$) amine, where at least one R group is a heteroaralkyl group.

As used herein, the term "alkylaminoalkyl" refers to an alkyl group substituted with an alkylamine group.

Analogously, "arylaminoalkyl" refers to an alkyl group substituted with an arylamine, and so forth, for any substituted amine described herein.

The term "alkenyl" used alone or as part of a larger moiety include both straight and branched chains containing at least one double bond and two to ten carbon atoms (i.e. 2, 3, 4, 5, 6, 7, 8, 9, or 10 carbon atoms), as well as cyclic, non-aromatic alkenyl groups such as cyclopropenyl, cyclobutenyl, cyclopentenyl, cyclopentadienyl, cyclohexenyl, cyclohexadienyl, etc. As used herein, alkenyl groups also include mixed cyclic and linear alkyl groups, such as cyclopentenylmethyl, cyclopentenylethyl, cyclohexenylmethyl, etc., so long as the total number of carbon atoms is not exceeded. When the total number of carbons allows (i.e. more than 4 carbons), an alkenyl group may have multiple double bonds, whether conjugated or non-conjugated, but do not include aromatic structures. Examples of alkenyl groups include ethenyl, propenyl, butenyl, butadienyl, isoprenyl, dimethylallyl, geranyl and so forth.

The term "aryl" used alone or as part of a larger moiety, refers to monocyclic, bicyclic, tricyclic or tetracyclic aromatic hydrocarbon ring system having five to 18 members, such as phenyl, 1-naphthyl, 2-naphthyl, phenanryl, 1-anthracyl and 2-anthracyl. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Polycyclic rings include naphthylene, anthracene, phenanthrene. Also included within the scope of the term "aryl", as it is used herein, is a group in which an aromatic ring is fused to one or more non-aromatic rings, such as in an indanyl, phenanthridinyl, dihydroacenaphthalene, or tetrahydronaphthyl, where the radical or point of attachment is on the aromatic ring. The term "aryl" also refers to aryl rings that are substituted such as, for example, 4-chlorophenyl, 3,4-dibromophenyl and so forth. An aryl group may have more than one substituent, up to the total number of free substitution positions. For example, an aryl group may have 1, 2, 3, 4, or 5 substituents. The substituents may the same or different. Substituents on an aryl group include hydrogen, halogen, alkyl, alkenyl, nitro, hydroxyl, amino, alkylamino, alkoxy, alkylthio, acyl, ester, amide, O-acyl, N-acyl, S-acyl as defined herein.

The term "aralkyl" refers to an alkyl substituent substituted by an aryl group.

The term "aryloxy" refers to an —O-aryl group, such as, for example phenoxy, 4-chlorophenoxy and so forth.

The term "arylthio" refers to an —S-aryl group such as, for example phenylthio, 4-chlorophenylthio, and so forth.

The term "heteroaryl", used alone or as part of a larger moiety, refers to heteroaromatic ring groups having five to fourteen members, five to ten members, or five to six members, in which one or more ring carbons, preferably one to four, are each replaced by a heteroatom such as N, O, or S. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 1-pyrazolyl, 3-pyrazolyl, 4-pyrazolyl, 2-pyridyl, 3-pyridyl, 4-pyridyl, 2-pyrimidyl, 4-pyrimidyl, 5-pyrimidyl, 3-pyridazinyl, 2-thiazolyl, 4-thiazolyl, 5-thiazolyl, 5-tetrazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indazolyl, isoindolyl, acridinyl, or benzoisoxazolyl. Also included within the scope of the term "heteroaryl", as it is used herein, is a group in which a heteroaromatic ring is fused to one or more aromatic or nonaromatic rings where the radical or point of attachment is on the heteroaromatic ring. Examples include tetrahydroquinolinyl, tetrahydroisoquinolinyl, and pyrido[3,4-d]pyrimidinyl. The term "heteroaryl" may be used interchangeably with the term "heteroaryl ring" or the term "heteroaromatic." A heteroaryl group may have more than one substituent, up to the total number of free substitution positions. For example, a heteroaryl group may have 1, 2, 3, 4, or 5 substituents. The substituents may the same or different. Substituents on a heteroaryl group include hydrogen, halogen, alkyl, alkenyl, nitro, hydroxyl, amino, alkylamino, alkoxy, alkylthio, acyl, ester, amide, O-acyl, N-acyl, S-acyl as defined herein.

The term "heteroaralkyl" refers to an alkyl group substituted by a heteroaryl, such as, for example, 2-pyridylmethyl, 3-pyridylmethyl, 1-imidazolomethyl, 2-imidazolomethyl and so forth. The term "heteroaryloxy" refers to an —O-heteroaryl group. The term "heteroarylthio" refers to an —S-aryl group.

The term "acyl" refers to a —C(O)-alkyl, —C(O)-aryl, or —C(O)-heteroaryl group. Accordingly, "alkylacyl" refers to a —C(O)-alkyl, "arylacyl" refers to a —C(O)-aryl, and "heteroarylacyl" refers to a —C(O)-heteroaryl group.

The term "ester" refers to a —C(O)—O-alkyl, —C(O)—O-aryl, or —C(O)—O-heteroaryl group. Accordingly, "alkyl ester" refers to a —C(O)—O-alkyl, "aryl ester" refers to a —C(O)—O-aryl and "heteroaryl ester" refers to a —C(O)—O— heteroaryl group.

The term "amide" refers to a —C(O)—NR-alkyl, —C(O)—NR-aryl, or —C(O)—NR-heteroaryl group where R is hydrogen or an alkyl, hydroxyl, or alkoxy group. Accordingly, "alkyl amide" refers to —C(O)—NR-alkyl, "aryl amide" refers to —C(O)—NR-aryl, and "heteroarylamide refers to —C(O)—NR-heteroaryl group.

The term "O-acyl" refers to an "—O—C(O)-alkyl," "—O—C(O)-aryl," or "—O—C(O)— heteroaryl" group.

The term "N-acyl" refers to an "—NR—C(O)-alkyl," "—NR—C(O)-aryl," or "—NR—C(O)-heteroaryl" where R is hydrogen, alkyl, hydroxyl, or alkoxy group.

The term "S-acyl" refers to "—S—C(O)-alkyl," "—S—C(O)-aryl," or "—S—C(O)— heteroaryl."

The term "N—O-acyl" refers to an "N—O—C(O)-alkyl," "N—O—C(O)-aryl," or "N—O—C(O)-heteroaryl" group.

As used herein, a "substituted" structure refers to a chemical structure where a hydrogen atom has been replaced by a substituent. A "substituent" is a chemical structure that replaces a hydrogen atom on the substituted structure. The term "substituent" does not imply that the substituent is smaller than the substituted structure. Substituents include hydrogen, halogen, alkyl, alkenyl, nitro, hydroxyl, amino, alkylamino, alkoxy, and alkylthio, acyl, ester, amide, O-acyl, N-acyl, S-acyl as defined herein.

As used herein, the term "tertiary amine" or "tertiary amino" means an amine-containing moiety where the nitrogen atom has three non-hydrogen substituents. One of the non-hydrogen substituents may be the core structure of the compound. Tertiary amine containing substituents include dialkylamino, cycloamino where the nitrogen atom is bonded to the parent structure, and N-alkylcycloamino, where a non-nitrogen atom of the a cycloamine moiety is bonded to the parent structure.

Compounds

Embodiments include compounds having the structure

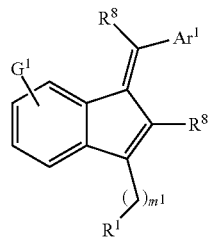

wherein $Ar^1$ is optionally substituted biphenyl, optionally substituted monocyclic aromatic or heteroaromatic, optionally substituted bicyclic aromatic or heteroaromatic, optionally substituted tricyclic aromatic or heteroaromatic, or optionally substituted tetracyclic aromatic or heteroaromatic. $m^1$ is 1, 2, 3, or 4. $R^1$ is a non-aromatic tertiary amine containing substituent having three to ten atoms. Each $R^8$ independently is H or alkyl.

In some embodiments, $Ar^1$ is optionally substituted biphenyl, optionally substituted bicyclic aromatic or heteroaromatic, optionally substituted tricyclic aromatic or heteroaromatic, or optionally substituted tetracyclic aromatic or heteroaromatic; wherein the optional substituents are halo, alkyl, or alkoxy, provided that if $Ar^1$ is naphthyl, then the optional substituents are alkyl. In some embodiments, $R^1$ is morpholin-4-yl.

In some embodiments, $m^1$ is 1 or 2. In some embodiments, $R^8$ is hydrogen.

$G^1$ may be one, two, three, or four substituents, each independently selected. In essence, the indene compound may be substituted by one or more substituents. In some embodiments, $G^1$ may be, for example, hydrogen, halogen, fluorine, hydroxyl, or alkoxy. Alternatively, two substituents may join to form a ring structure, such as methylenedioxy. In some embodiments, the $G^1$ is a single non-hydrogen substituent. In some embodiments, $G^1$ is a fluorine substituent. In some embodiments, the substituent, $G^1$ resides on the 4-position, on the 5-position, on the 6-position, or on the 7-position of the indene structure.

In some embodiments, $R^1$ may be a substructure depicted below:

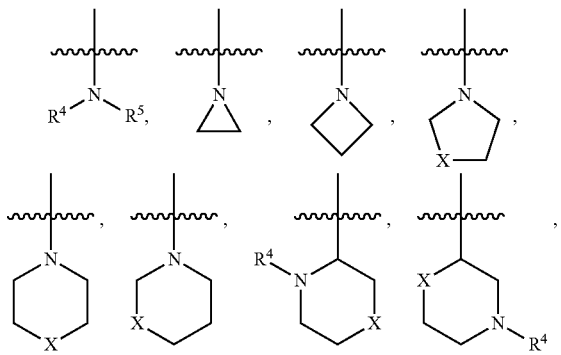

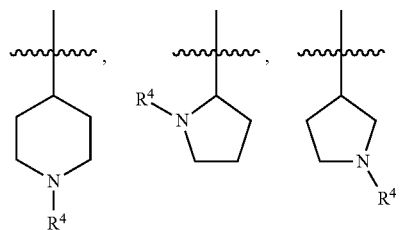

wherein X may be $CH_2$, O, S, $NR^{11}$, SO, or $SO_2$. $R^4$ may be H or alkyl, $R^5$ may be H or alkyl. $R^{11}$ may be an acyl group, —C(O)—N($R^7$)$_2$, —C(O)—O—$R^7$, $S(O)_2$-alkyl, $S(O)_2$-aryl, —C(O)—$NR^7$—$S(O)_2$-alkyl, or —C(O)—$NR^7$—$S(O)_2$-aryl where $R^7$ is H or alkyl. In some embodiments, $R^1$ may be one of

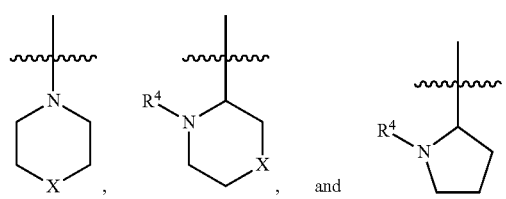

wherein X may be $CH_2$, O, S, $NR^5$, SO, and $SO_2$ and $R^4$ is alkyl, $R^5$ is alkyl. In some embodiments, $R^1$ is morpholine (e.g., morpholin-4-yl), having the structure

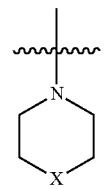

where X is O.

In some embodiments, $Ar^1$ may be an aromatic structure shown below

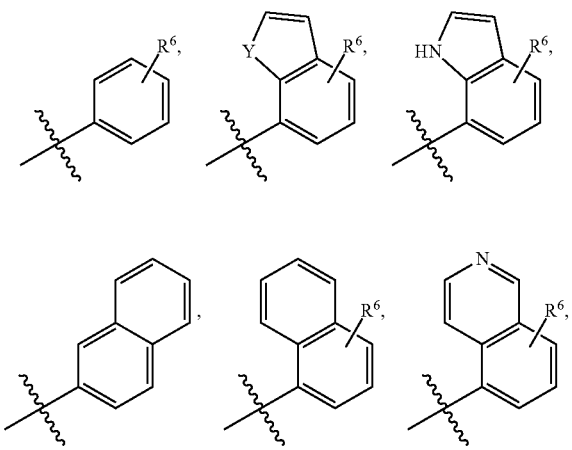

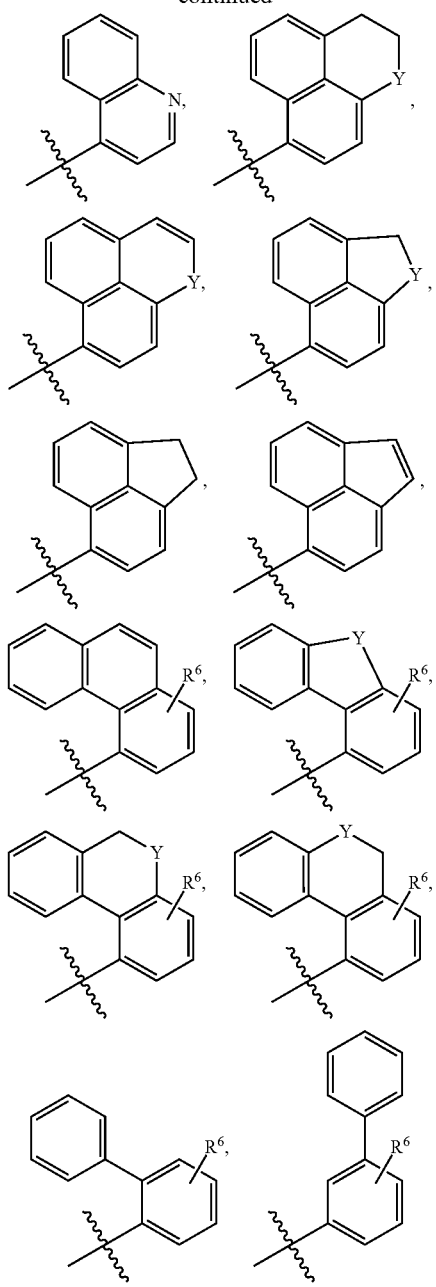
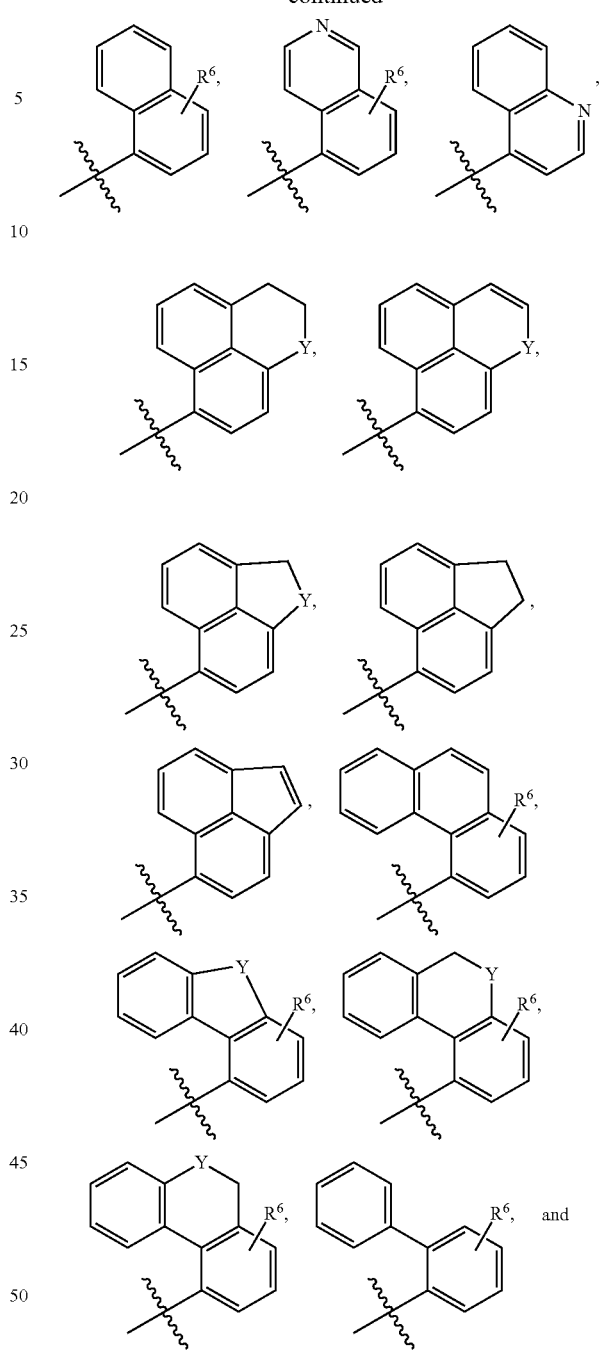
where $R^6$ may be H, alkyl, alkoxy, alkylacyl, alkyl ester, or alkyl amide. Y may be O, S, S(O), S(O)$_2$, NR$^{10}$, or CH$_2$. $R^{10}$ may be H or alkyl.
In some embodiments, Ar$^1$ may be selected from the group consisting of
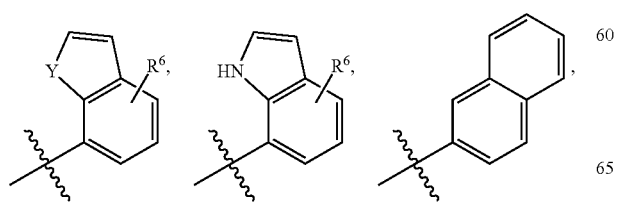
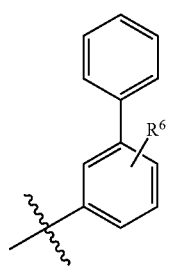
where $R^6$ is H, alkyl, alkoxy, alkylacyl, alkyl ester, or alkyl amide; Y is O, S, S(O), S(O)$_2$, NR$^{10}$, or CH$_2$; and $R^{10}$ is H or alkyl.

In some embodiments, $Ar^1$ may be
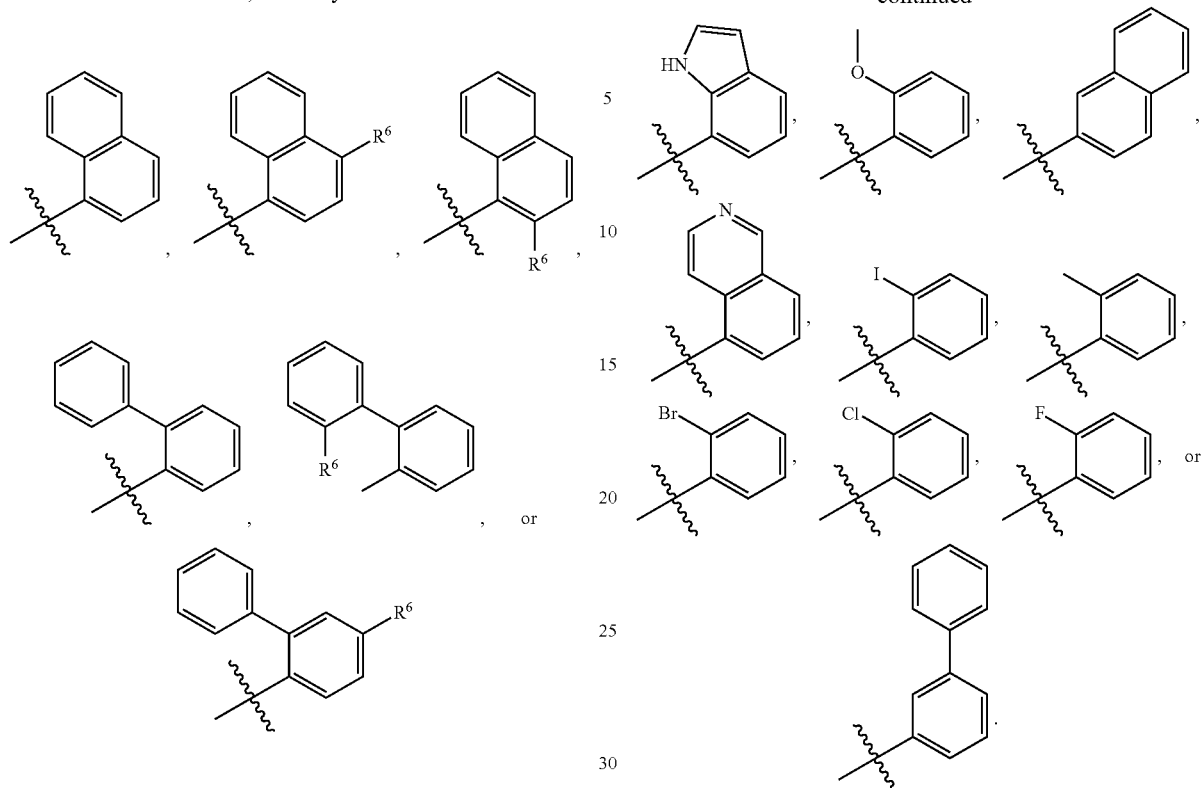
where $R^6$ may be alkyl, alkoxy, alkylacyl, alkyl ester, or alkyl amide. In some embodiments, $R^6$ can be alkyl, or alkoxy. In some embodiments, $Ar^1$ may be
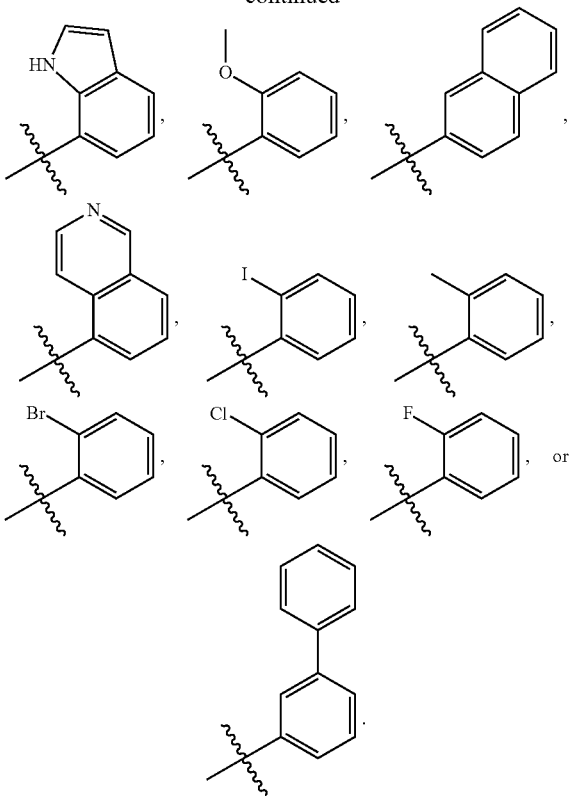
In some embodiments, the compound can be selected from:
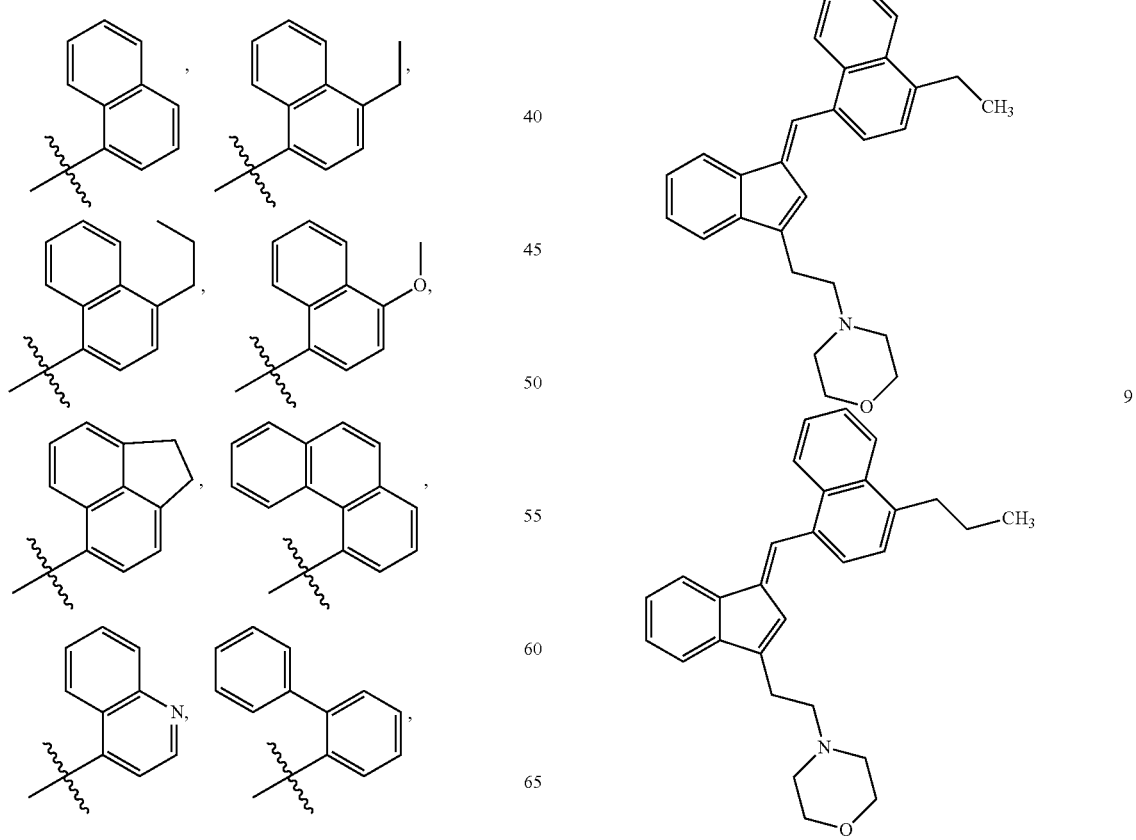

12
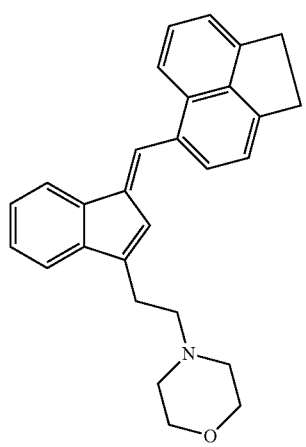
13
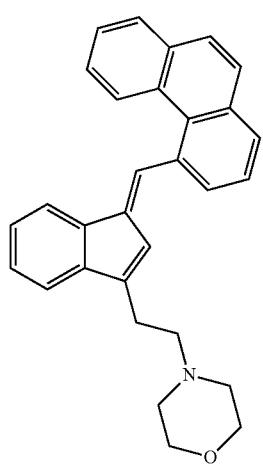
14
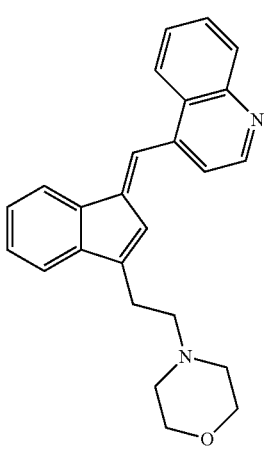
16
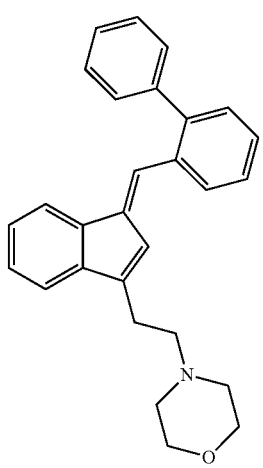
17
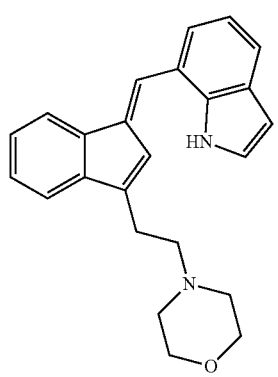
20
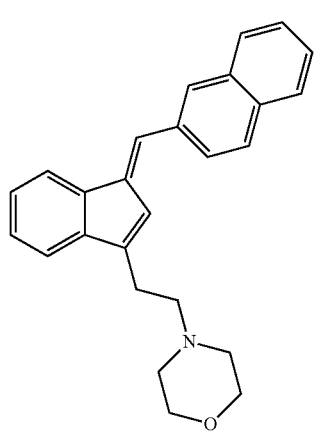

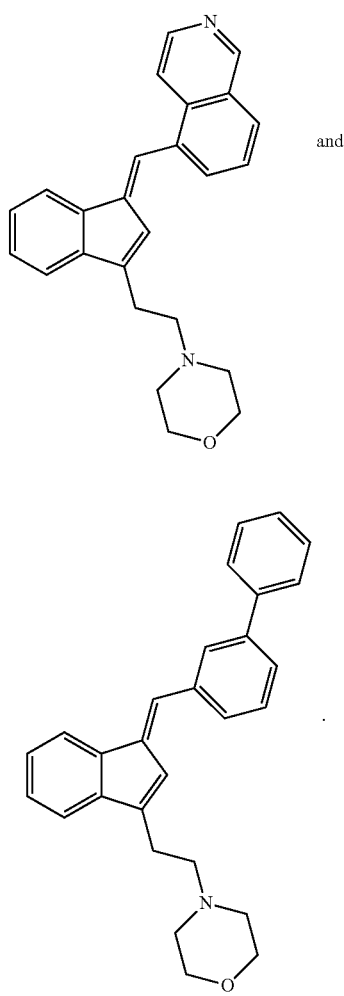

In some embodiments, the compound is not (E)-4-(2-(1-((4-methoxynaphthalen-1-yl)methylene)-1H-inden-3-yl)ethyl)morpholine; (E)-4-(2-(1-(naphthalen-1-ylmethylene)-1H-inden-3-yl)ethyl)morpholine; (E)-4-(2-(2-methyl-1-(naphthalen-1-ylmethylene)-1H-inden-3-yl)ethyl)morpholine; (E)-4-(2-(2-methyl-1-(quinolin-4-ylmethylene)-1H-inden-3-yl)ethyl)morpholine; (E)-4-(3-(1-(naphthalen-1-ylmethylene)-1H-inden-3-yl)propyl)morpholine; (E)-4-(3-(1-(4-methoxynaphthalen-1-ylmethylene)-1H-inden-3-yl)propyl)morpholine; (E)-4-(2-(1-((4-methoxynaphthalen-1-yl)methylene)-2-methyl-1H-inden-3-yl)ethyl)morpholine; (E)-4-(2-(1-((1H-indol-4-yl)methylene)-1H-inden-3-yl)ethyl)morpholine; or (E)-4-(2-(1-(anthracen-9-ylmethylene)-1H-inden-3-yl)ethyl)morpholine. Embodiments include compounds having the structure

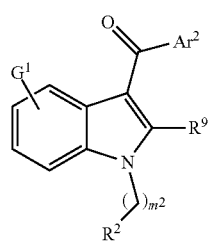

wherein $Ar^2$ is optionally substituted biphenyl, optionally substituted monocyclic aromatic or heteroaromatic, optionally substituted bicyclic aromatic or heteroaromatic, optionally substituted tricyclic aromatic or heteroaromatic, or optionally substituted tetracyclic aromatic or heteroaromatic. $m^2$ is 2, 3, 4, 5, or 6. $R^2$ is $-CH_3$, $-CO_2R^3$, $-CON(R^4)_2$, halogen (F, Cl, Br, I), hydroxyl, nitro, amino, monoalkylamino, or non-aromatic tertiary amine containing substituent having three to ten atoms. $R^3$ is H or alkyl. $R^4$ is, independently, hydrogen or alkyl. $G^2$ is one, two, three, or four substituents, each independently selected from hydrogen, halogen, fluorine, hydroxyl, alkoxy, and methylenedioxy. $R^9$ is H or alkyl.

In some embodiments, $Ar^2$ is optionally substituted biphenyl, optionally substituted bicyclic aromatic or heteroaromatic, optionally substituted tricyclic aromatic or heteroaromatic, or optionally substituted tetracyclic aromatic or heteroaromatic; wherein the optional substituents are halo, alkyl, —O-alkyl, —CO-alkyl, —COOR$^4$, or —CON(R$^4$)$_2$, provided that if $R^8$ is methyl, then $Ar^2$ is not 4-halonaphth-1-yl. In some embodiments, $R^2$ is $-CH_3$, $-CO_2R^3$, $-CON(R^4)_2$, F, Cl, I, hydroxyl, nitro, amino, monoalkylamino, or morpholin-4-yl.

In some embodiments, $m^2$ is 2, 3, 4 or 5. In some embodiments, $m^2$ is 2. In some embodiments, $R^9$ is H.

$G^2$ may be one, two, three, or four substituents, each independently selected. In essence, the indole compound may be substituted by one or more substituents. In some embodiments, $G^2$ may be, for example, hydrogen, halogen, fluorine, hydroxyl, or alkoxy. Alternatively, two substituents may join to form a ring structure, such as methylenedioxy. In some embodiments, the $G^2$ is a single non-hydrogen substituent. In some embodiments, $G^2$ is a fluorine substituent. In some embodiments, the substituent, $G^2$ resides on the 4-position, on the 5-position, on the 6-position, or on the 7-position of the indole structure.

In some embodiments, $R^2$ may be fluorine, $-CH_3$, $-CO_2R^3$ where $R^3$ is alkyl, $-CO_2H$ or a substructure shown below

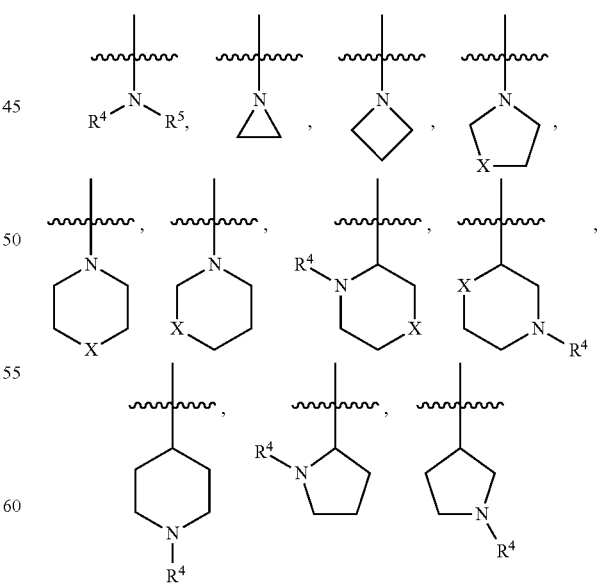

where X may be $CH_2$, O, S, $NR^6$, SO, and $SO_2$. $R^4$ may be H or alkyl, $R^5$ may be H or alkyl. $R^6$ is an acyl group, $-C(O)-N(R^7)_2$, $-C(O)-O-R^7$, $S(O)_2$-alkyl, $S(O)_2$- aryl, —C(O)—NR'—S(O)$_2$-alkyl, or —C(O)—NR$^7$—S(O)$_2$-aryl where R$^7$ is H or alkyl.

In some embodiments, R$^2$ may be fluorine, —CH$_3$, —CO$_2$H, —CO$_2$CH$_2$CH$_3$ or a substructure shown below

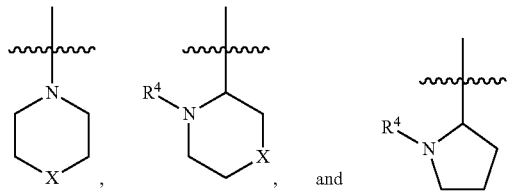

where X may be CH$_2$, O, S, NR$^5$, SO, and SO$_2$. R$^4$ is alkyl, R$^5$ is alkyl. In some embodiments, R$^2$ is methyl (—CH$_3$). In some embodiments, R$^2$ is morpholine.

In some embodiments, R$^2$ may be fluorine, —CH$_3$, —CO$_2$R$^3$ where R$^3$ is alkyl, —CO$_2$H or morpholin-4-yl.

In some embodiments, Ar$^2$ may be

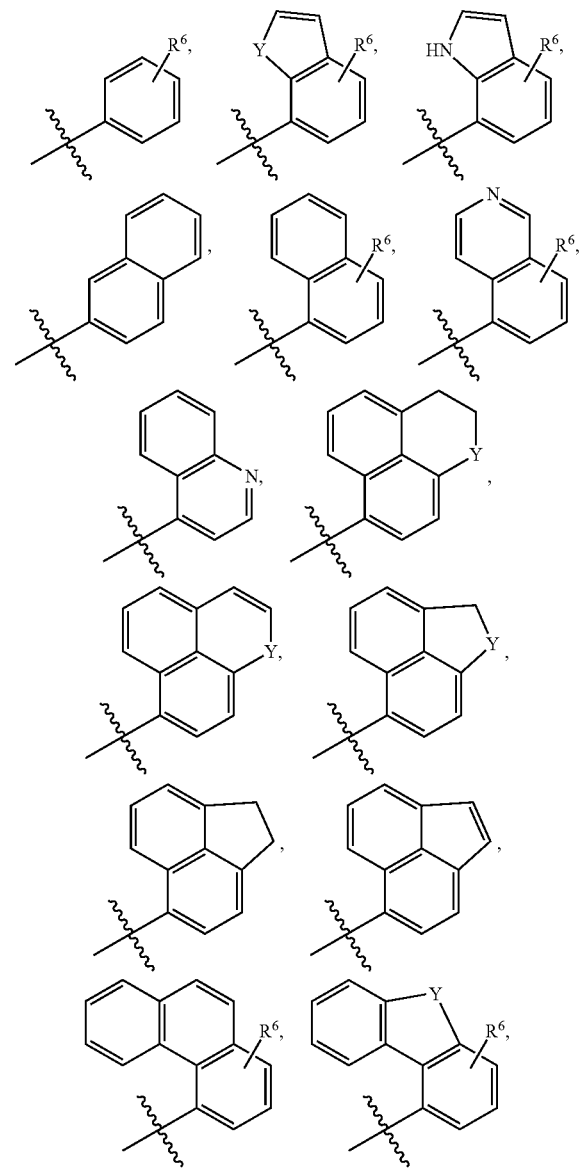

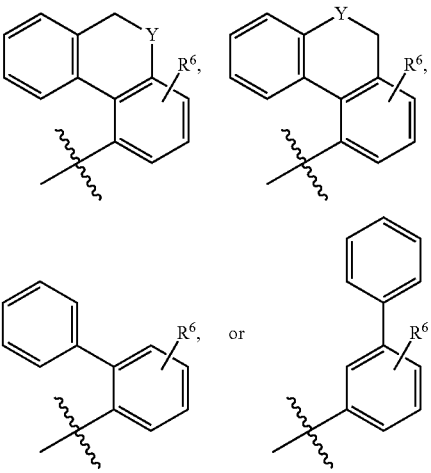

wherein R$^6$ is H, alkyl, alkoxy, alkylacyl, alkyl ester, or alkyl amide. Y is O, S, S(O), S(O)$_2$, NR$^{10}$, or CH$_2$ where R$^{10}$ is H or alkyl.

In some embodiments, Ar$^2$ may be

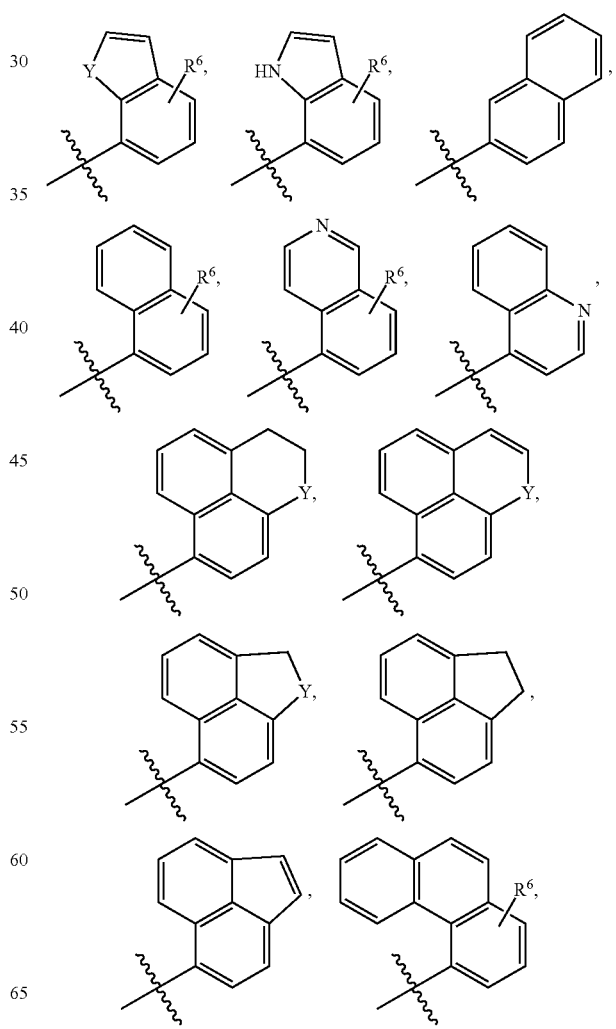

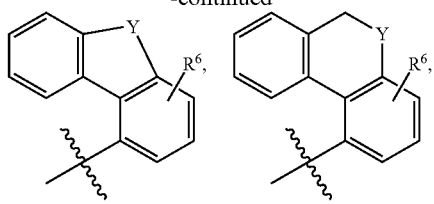
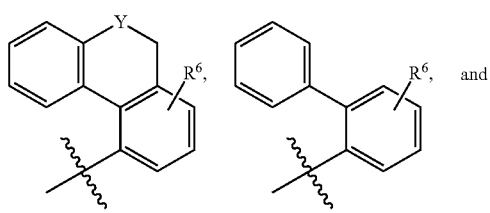
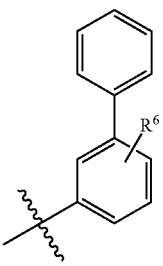
where $R^6$ is H, alkyl, alkoxy, alkylacyl, alkyl ester, or alkyl amide; and Y is O, S, S(O), S(O)$_2$, NR$^{10}$, or CH$_2$; and R$^{10}$ is H or alkyl.
In some embodiments, Ar$^2$ may be
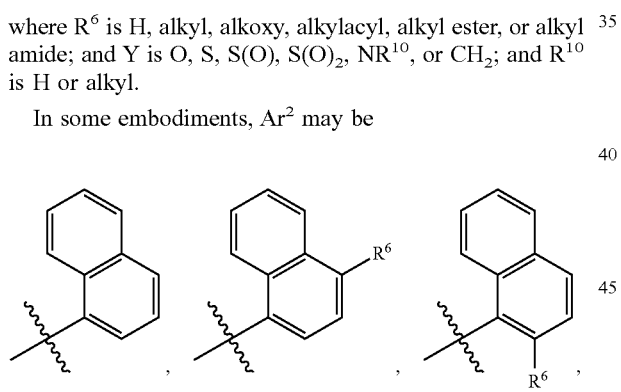
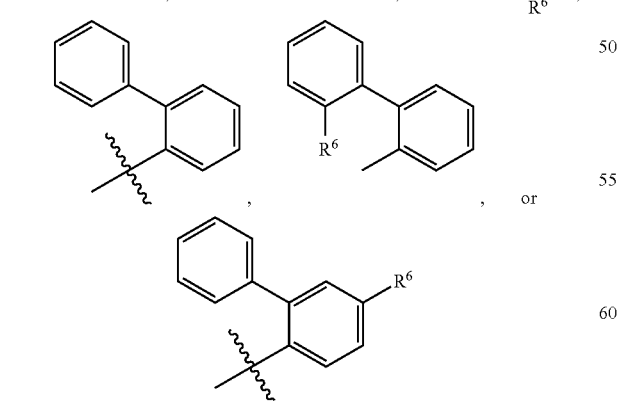
where $R^6$ may be alkyl, alkoxy, alkylacyl, alkyl ester, or alkyl amide.
In some embodiments, Ar$^2$ may be
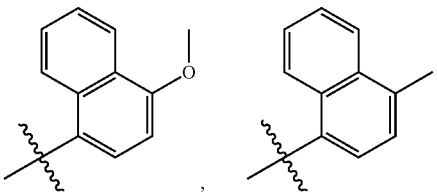
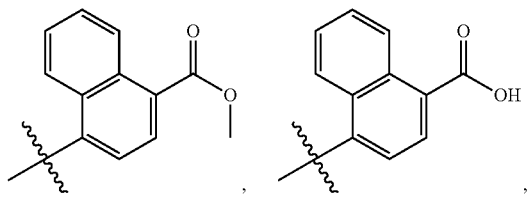
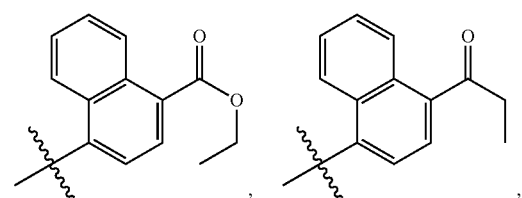
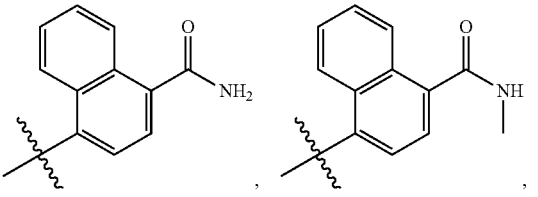
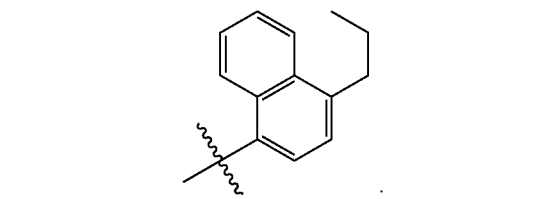
In some embodiments, Ar$^2$ may be
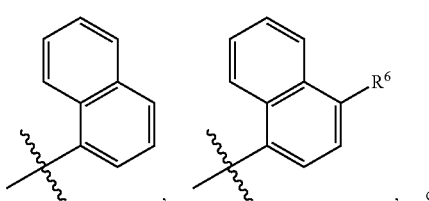
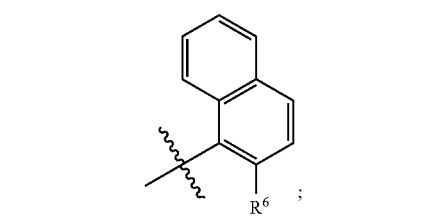
$R^2$ is —CH$_3$ or halogen; and $R^9$ is H.

In some embodiments, the compound is selected from:
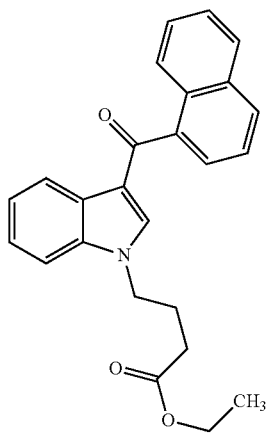
50
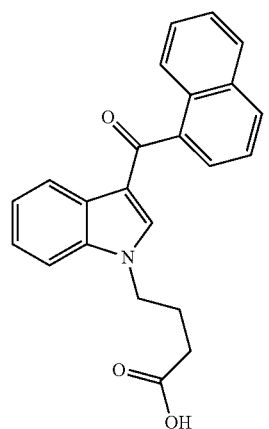
51
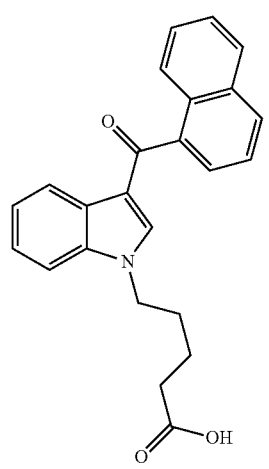
52
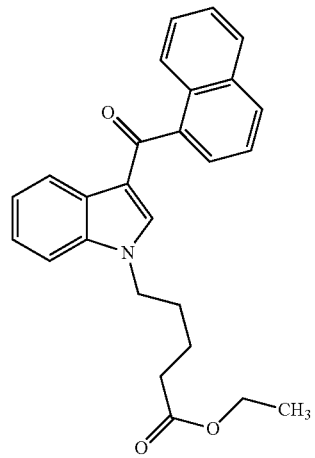
53
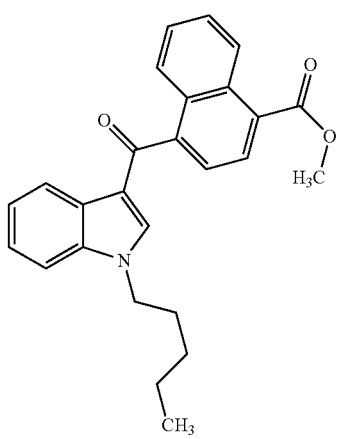
54
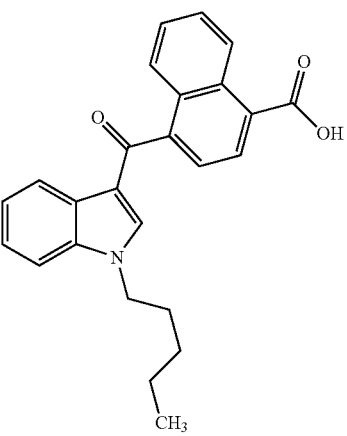
55

56
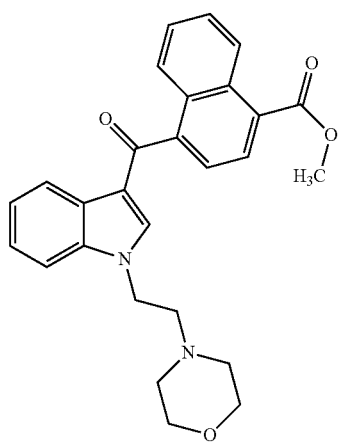
57
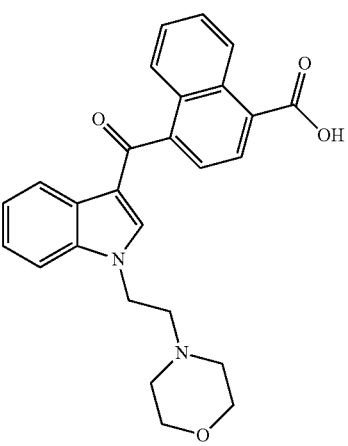
58
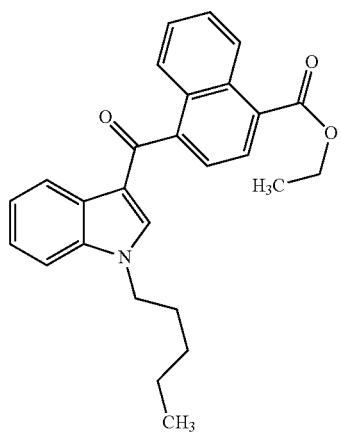
59
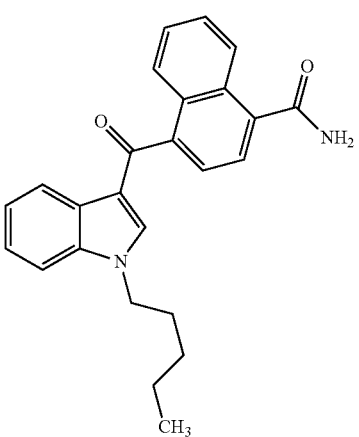
60
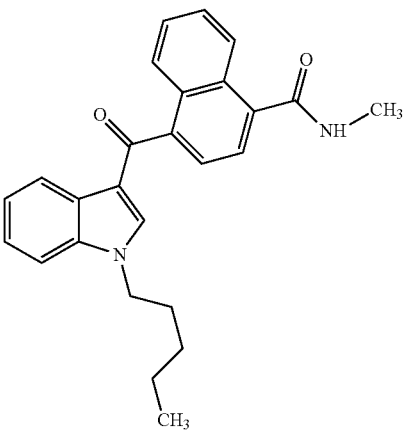
61
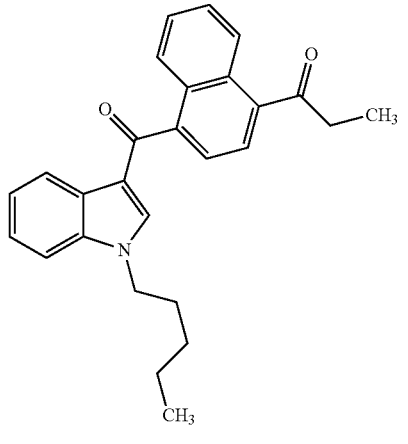

62
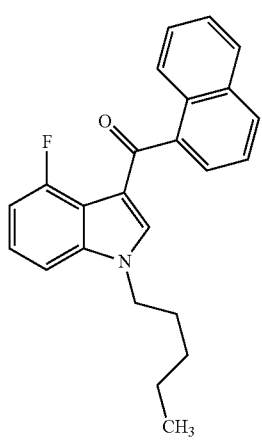
63
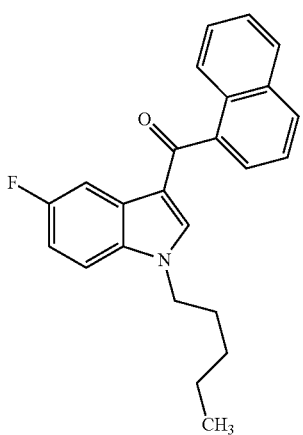
64
65
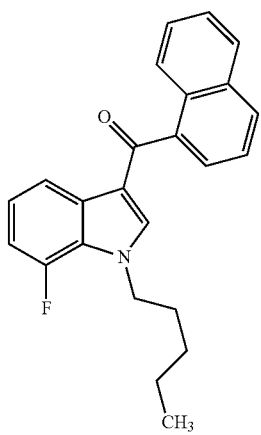
66
67 and
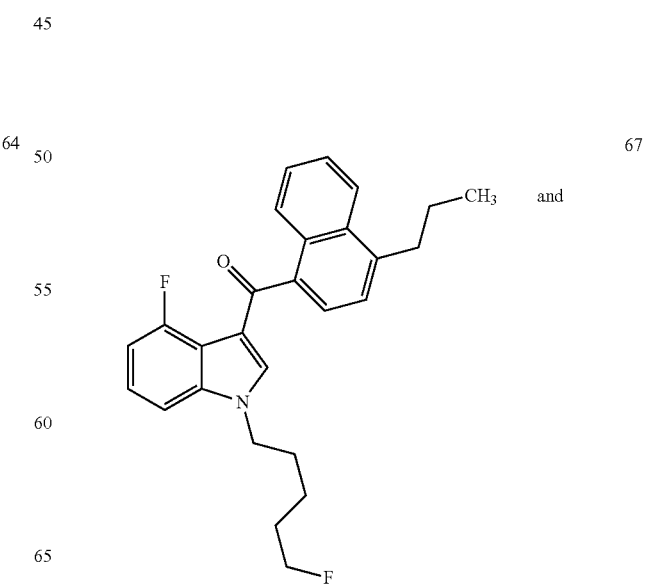

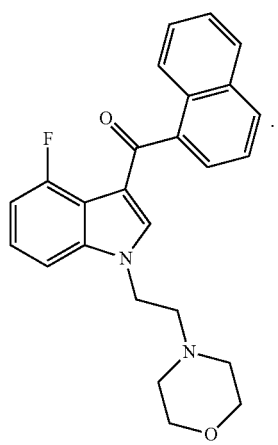

68

In some embodiments, the compound is not (1-(3-bromopropyl)-2-methyl-1H-indol-3-yl)(naphthalen-1-yl) methanone; (4-chloronaphthalen-1-yl)(7-methoxy-2-methyl-1-pentyl-1H-indol-3-yl)methanone; (4-bromonaphthalen-1-yl)(7-methoxy-2-methyl-1-pentyl-1H-indol-3-yl)methanone; or (4-bromonaphthalen-1-yl)(7-fluoro-2-methyl-1-pentyl-1H-indol-3-yl)methanone.

Examples of compounds according to the invention include those shown in Table 1.

Peripherally Acting Compounds

Current clinical treatments with FDA-approved cannabinoid-based analgesics can provide relief from chronic pain symptoms, but also produce several important CNS-mediated side effects which greatly limit their usefulness.

Peripherally-acting cannabinoids compounds may have limited permeability at the blood-brain barrier (BBB) while possessing high affinity for cannabinoid receptors. In pre-clinical testing example compounds were effective in alleviating chronic pain of inflammatory and neuropathic origin without any centrally-mediated side effects.

Compounds described herein have an indole or indene core and substituted about these rings. Examples have substitution on the indole at N-1 with alkyl groups (e.g. n-pentyl), C-3 with 1-naphthoyl that is substituted in the 4-position with various moieties such as alkyl, ether, acyl, or halo. Other examples include other C-3 aroyl (—C(O)—Ar) substituents. Further examples include indole core substituted on the benzene ring with fluorines. The indenes may be substituted in the C-3 position with an ethyl-4-morpholino group, at the C-1-position with a 1-naphthalenylmethylene that is substituted in the 4-position as above for the indoles or with other aryl-methylidene or -ethylidene groups. The indene core may be substituted on the benzene ring with fluorines. The compounds have affinity for the CB1 receptor and exhibit minimal penetration of the MDCK model of the blood-brain barrier.

Some compounds having an indole or indene core are described in U.S. Pat. Nos. 6,013,648; 5,292,736; and 5,013,837, each of which is incorporated by reference in its entirety.

Compounds described herein are those with an indene or indole core, substituted on the 2-indene ring at C-1, C-3 and either or multiple of the 4-7 indene ring positions and for the indole ring on the N-1, C-3 and either or multiple of the 4-7 indole ring positions. Specific to these are those compounds exhibiting the properties of affinity for the cannabinoid CB1 receptor (Ki≤300 nM), peripheral selectivity as indicated by the MDCK assay and/or behavioral testing showing minimal or no CNS penetration or "tetrad" effects respectfully, and reduced neuropathic pain as demonstrated by SNE and/or CFA inflammatory pain testing. Representative examples are given in the appended spreadsheet.

The indene C-1 substituent is a polycyclic arylidene system or heteroaromatic system with N, O, or S as the heteroatom(s) singly or in combination. Such polycyclic systems are those that fit the abcd template (shown below) with some or all of the rings. For a non-limiting example, the non-heteroaromatic system can formally be derived from phenanthrene-4-carboxaldehyde, naphthylene-2-carboxaldehyde or o-phenyl-benzaldehyde heteroaromatic system. The heteroaromatic system can be quinoline, isoquinoline, indole, benzofuran or benzothiophene that is suitably substituted for formal condensation with the indene at C-1 via a carboxaldehyde moiety.

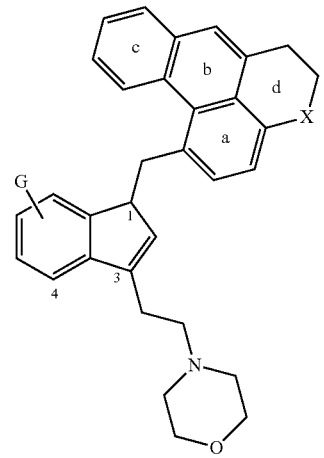

abcd system can involve some or all of the rings.

abc: where a and c are aromatic, b is aromatic or non-aromatic as c6 or c5 carbocyclic or heterocyclic or absent (e.g. 196-41, 138-139).

abd: where a and b are aromatic or heteroaromatic, d is aromatic or c6 or c5 carbocyclic (e.g. 174-38 derived from acenaphthene-5-carboxaldehyde; analogs derived from acenaphthylene-5-carboxaldehyde or fluorene-4-carboxaldehyde) or heterocyclic pyran or lactone.

ac: e.g. o-phenylbenzylidene derived from o-phenylbenzaldehyde (138-39).

x=$(CH_2)_{n=0,1}$; O, S, NR(R=H, alkyl).

Substituents on the 1-naphthylene aromatic system at the indene C-1 are most favored at the 4-position and are carboxy esters of small alcohols, primary and secondary amides, acyl moieties from acetyl through pentanoyl, and ethers as methoxy through pentyloxy, and alkyl as methyl, ethyl, n-propyl and butyl.

The indene 3-substituent in the examples provided is the morpholino-N-ethyl moiety, which surprisingly conferred peripheral selectivity in the indene series. Other beta-amino ethyl groups with other hetero atoms or groups such as sulfone are extensions that are claimed.

The indene 4-7 positions can be substituted with either or multiple halogens (fluorine being a favored example) or oxygens such as hydroxyl, methoxyl or methylenedioxy.

The indole core scaffold follows similar structural patterns except that in lieu of arylidene moieties the C-3 of the indoles are substituted with aroyl moieties following the abcd template in (2) above.

Modified 1-arylidene indenes (A1) and 3-aroyl indoles (A2) as peripherally selective CB1R agonists are described herein. The first four areas focus on the pendant 3-aroyl and the 1-arylidene moieties, which have been majorly implicated in the CB1R binding that stabilizes the active state of CB1R (Figure A). Analogs should be able to adopt the bioactive conformation, similar to the archetypical WIN 55,212-2, aligning the naphthyl rings in the X-Z plane (into the plane of the paper horizontally) (relative to the X-Y plane of the paper for the indole or indene ring) and stack with aromatic residues in the helices of the CB1R transmembrane region TM 3-4-5-6. The four areas contribute to binding affinity and potentially receptor subtype selectivity (CB1R vs CB2R) by 1) optimally juxtaposing aromatic stacking interaction surface, 2) enhancing the strength of the interaction by increasing or decreasing the electron density of the pendant aryl groups, 3) the productive effect of 4-position substituents of 1-naphthyl rings beyond those currently reported, and 4) conformational constraint via atropisomers that favor the binding and activation conformation.

The first area, Aromatic Stacking Interactions demonstrate that favorable binding interactions extend beyond the naphthyl moiety to our current and evolving annotated template A3 for indenes. Numbers 1, 2, 3, 5 and 6 represent regions/rings associated with good binding (Ki=1-83 nM) and underlined numbers (i.e. 4, 7) represent regions of decreased binding (Ki≥1 μM).

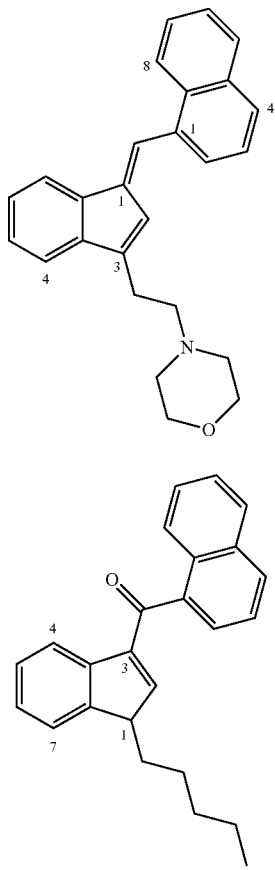

A1

A2

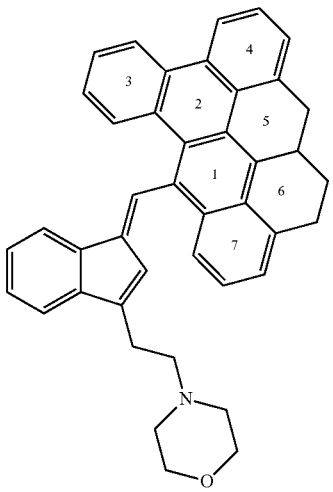

A3

Mapped areas include: the 2/1 ring pair, the naphthyl system (Ki=4.69 nM); the 3/1 non-fused ring pair, 2-phenyl benzylidene (Ki=82.9 nM); the 2/1/5 (or 2/1/6) groupings, which are the possible templates for 4-propyl- or 4-ethyl-1-naphthylidene systems (acyclic propyl and ethyl) (Ki=1.18 and 0.86 nM, respectively), while the 1/4 is the inactive m-phenyl benzylidene (Ki=2603 nM) and the 2/1/7 is the putatively inactive 9-anthracene based on the inactive 9-anthracenoyl system in the indoles[120].

The A3 template may be used as a guide to select aryl carboxaldehydes to couple with 3-(morpholinoethyl)-2-indene to prepare the target indenes. Using this template, the analog 1/2/3 (from phenanthrene-4-carboxaldehyde) was prepared and found to be active (Ki=22.9 nM). Further, based on the 4-ethyl- and the 4-propyl-1-naphthylidene, described above, the ethyl and propyl moieties could be part of either of two additional non-aromatic rings (i.e. 1/2/5 or 1/2/6). This was tested with a, ring constrained, ethyl analog of the 1/2/5 ring configuration from acenaphthene-carboxaldehyde that gave an active, but less active, analog (Ki=15.9 nM). This suggests the possibility that the ethyl might have an out of plane interaction or that the conformation of the ethyl (or propyl) is more like 1/2/6. This suggests preparing a 1/2/6 analog with the number 6 ring as 5- or 6-membered aliphatic. It is understood that as results from analogs are obtained, the template may change towards a more refined SAR that systematically explores enhanced affinity and potential CB1R vs CB2R selectivity.

Stacking of aromatic rings can be in a parallel, offset parallel or edge-to-face (T-stacked) mode that maximizes an attraction between the relatively positive σ-bond carbon framework and the relatively negative π-bond electron cloud[121]. In stacking aromatic rings, attractive interactions can be enhanced by increasing or decreasing the electron density of the ligand's pendant ring relative to that of the receptor ring with which it is stacked. Such altered electron density is observed in heteroaromatic rings that are electron poorer when N is in a 6-member ring (relative to an all carbon 6-member ring) or electron richer (than phenyl) when the heteroatom is in a smaller (i.e. 5-member) ring (e.g. pyrrole, furan). CB1R binding and activation may be modified with indole and indene ligands containing heteroaromatic rings with altered electron density that also match the mapping described previously in the pendant aryl ring systems. Some such substitutions have been examined (e.g., electron-rich 7-coupled indole and electron-poor 5-coupled isoquinoline both of which placed the heterorig distal to the point of coupling, while maintaining the oriented overlap matching the parent naphthyl rings) and found increased affinity with an electron-rich distal ring. The reported[120] electron-rich distal 4- or 7-coupled-benzofuran aromatic ring with good IC$_{50}$ values supports our observations with the 7-coupled indole above. Similarly, we found an electron-poor proximal ring of 4-coupled quinoline to have good affinity (Ki=23 nM) while others reported[120] a good IC$_{50}$ with an electron-poor proximal 2-coupled quinoline. These consistent few examples suggest potential improvement in both binding and activation, by appropriate adjustment of electron density of stacking aromatic rings pendant to indole and indene systems. These merit further examination since the few examples that are available for comparison cross both core templates (indoles and indenes) and position of coupling and hence the positioning of the heteroatom, both of which could influence binding and activation.

The scope of the aryl substituent may enhance ligand properties. We have prepared and screened a 1-naphthoyl-4-carbomethoxy-indole that exhibited good CB1 binding affinity (Ki=20 nM) and <1% MDCK permeability, then significantly improved affinity as the 4-propionyl analog (Ki=5.7 nM). In the indene class of analogs, a 4-methoxy-1-naphthylidene-indene (13339-135-35) had superior affinity (Ki=2.4 nM) and <1% MDCK permeability. Further, the 4-n-propyl- and 4-ethyl-naphthylidene indenes had 1 nM CB1R affinity in accord with results with the corresponding naphthoyl-indole analogs[118]. Peripheral in vivo activity was demonstrated for 4-substituted 1-naphthylidene indenes (see 13339-135-35 results in FIGS. 2B & 5). While the hydrolyzable 4-carbomethoxy ester was unstable in plasma or S9 liver microsomal fraction in vitro (only 3% remained with S9 @ 30 min), non-hydrolyzable analogs such as the 4-n-propyl (13339-145-35) had significantly improved in vitro stability (39% remained with S9 @ 30 min). Further, the latter showed enduring in vivo activity in alleviating neuropathic pain (see FIG. 1) suggesting that stability, activity and peripheral selectivity may be modified. Modulation of 4-naphthyl and other corresponding active pendant aryl indenes and indoles especially may lower BBB permeability. This is often achieved by the addition of topological polar surface area (TPSA) to a structure[3]. This can be achieved by adding heteroatom moieties such as amides, ureas, sulfonamides, sulfonyl ureas, carbamates, etc., that have been partially explored in the context of CB1R peripherally selective agonists[125]. Similar modification were used to develop peripherally selective CB1R antagonists[112,113].

The binding conformation of a ligand in a receptor active site might not be the same conformation as the ground state of the ligand, thus requiring a conformational change that is done at the expense of the binding energy and reduced ligand-receptor affinity. Further, ligand conformation can also affect receptor selectivity (i.e. CB1R and CB2R). Therefore, when a ligand is conformationally constrained, if the restricted conformation is that of the binding conformation, the binding affinity will be improved and potentially the receptor selectivity will be enhanced in favor of one or the other receptors. For the E-naphthylidene indenes (A1), this has been demonstrated by the exocyclic double bond that locks the molecule into an E-configuration, equivalent to the active s-trans conformation of 3-naphthoyl-indoles (A2)[117]. Yet, there is further conformational freedom that can be addressed; rotation about the single bond that links the naphthyl ring to the vinyl group. Computational modeling of the CB1R binding of indoles and indenes, such as those we propose here, supports alignment of the naphthoyl ring with the X-Z plane[115]. Two such alignments, with the distal phenyl of the naphthyl ring into or out of the X-Y plane of the indole or indene, are possible. In the receptor active site, one conformation would favor binding and the other would not.

Some embodiments include analogs of active naphthylidene indenes that are constrained into each of the non-interconverting isomers in the form of atropisomers (isomers formed due to limited rotation about a single bond, e.g. tetra-ortho-substituted biphenyls, B3). Analogous to B3, wherein a-d are of sufficient size (>H) (and are non-identical moieties in B3) and thus lock B3 into enantiomeric atropisomers that can't rotate past the steric blockade, the naphthylidene indene analogs B1 and B2 are similarly locked. All the atoms of each connected ring are rigidly coplanar thus serving the same paradigm as the tetra substituted phenyl rings in B3 in inducing atropisomerism. It can be seen that the moieties a-f in B1 and B2 serve the same steric interplay as a-d in B3 to induce atropisomerism. In analog B2 the extension of e (i.e. e=Me), which replaces the steric role of d in B1, represents an E-naphthylidene-2-methyl-indene that is also active[126]. The synthesis of the B1 analogs will follow that discussed herein but will employ suitably substituted ketones (to provide moieties f, b and d) instead of aldehydes. The E-isomer may be favored for analogs B1 and be chromatographically separable from the Z-isomer that could be present. The resulting mixture of the two enantiomers of the E-isomer would be subsequently resolved on chiral columns. The E-analogs B2, from 2-methyl-indenes may be less favored than the Z-isomer favored in 2-methyl-indenes. Photochemical isomerization has been used in naphthylidene indenes to produce mixtures from either isomer and could be employed to generate E/Z-mixtures from Z-fractions[117].

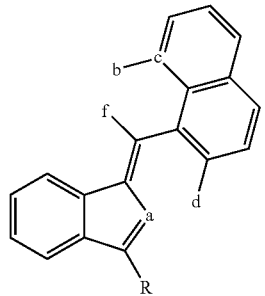

B1

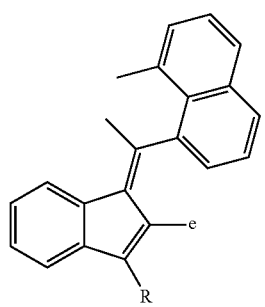

B2

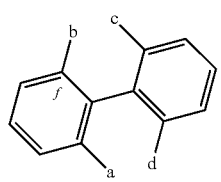

B3

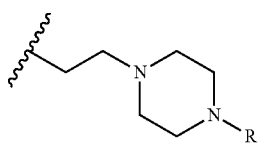

Z

The 1-n-pentyl-3-(1-naphthoyl)-indole family (A2) of CB1R agonists have been widely synthesized[118] as CB1R/CB2R agonist ligands but little has been scientifically pursued in the areas of pharmacology and behavior. The metabolism of the parent A2 and an analog has been investigated[127,128] and found to be rapidly and extensively metabolized (predominantly hydroxylated at indole 4-7 positions) affording full and partial agonists and neutral antagonists. The potential for many active metabolites could create a polypharmacology, which would best be avoided. The introduction of electron drawing substituents at and proximal to metabolism sites inhibit metabolism. We have observed improved metabolic stability in selected fluoroindoles (i.e. 7-fluoro) while maintaining high CB1R affinity and non-permeability of the MDCK model. Accordingly, substitution of the indene ring may improve metabolic stability.

Figure 5:
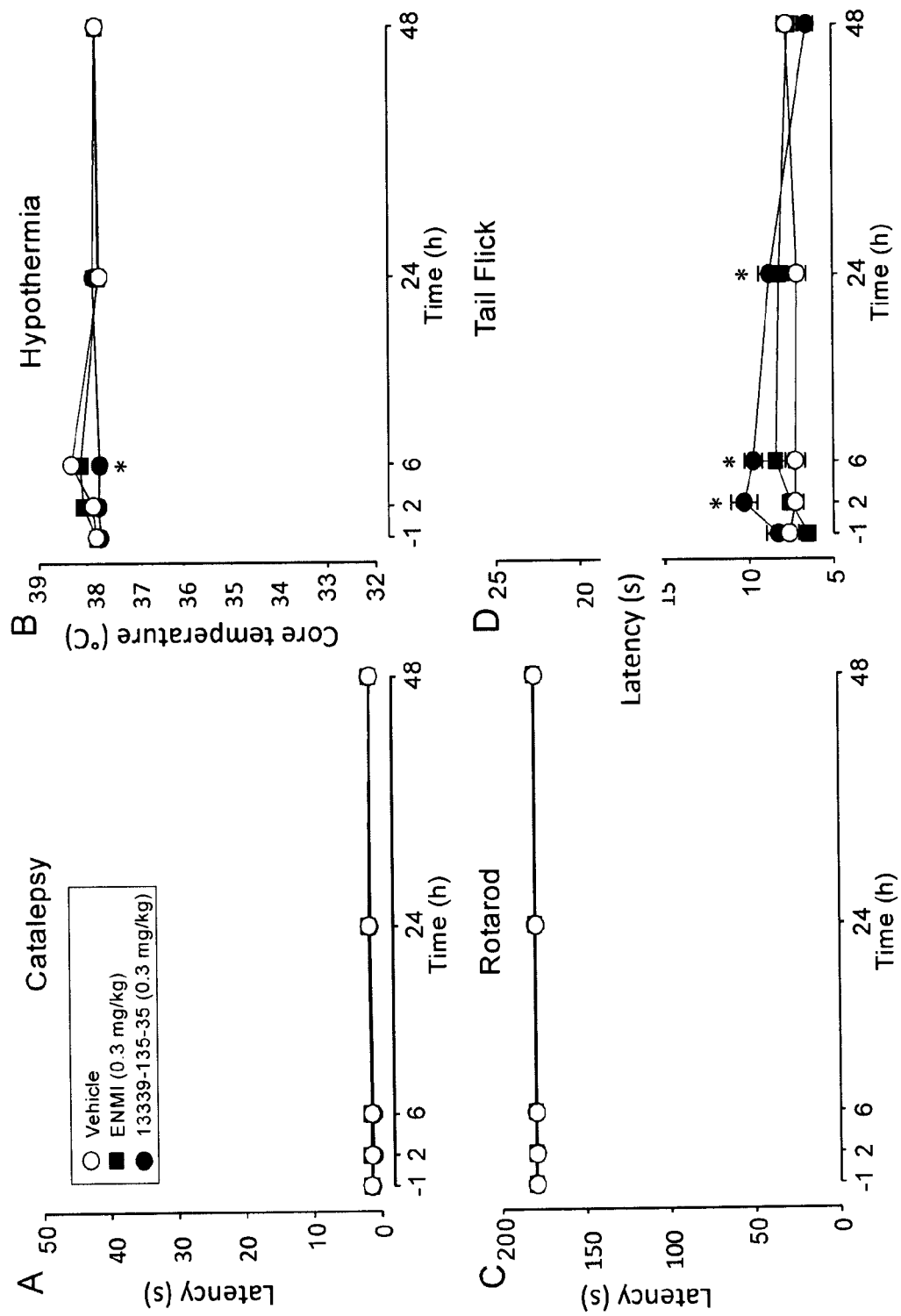
FIG. 5 shows lack of CNS effects of indene CBR ligands in the "Tetrad" of catalepsy, hypothermia, rotarod and tail-flick tests.

The morpholinoethyl-indene family (e.g. A1) has shown peripheral selectivity indicated by the MDCK in vitro model and by behavioral studies in rats (see FIG. 5). While the indoles (A2) also do not permeate the MDCK membrane, behavioral studies are yet to be examined. Peripheral selectivity may be achieved through the addition of topological polar surface area (TPSA) to the structures[122, 123, 129]. This could be pursued, for example, by replacing the 1-[2-(4-morpholino)ethyl] or pentyl group in A1 and A2 with active moieties U, V, X(R=Me)[130] and others Y, Z, subsequently modified with heteroatom moieties (R=amides, ureas, sulfonamides, sulfonyl ureas, carbamates, etc.) which have had good success in affording peripheral selectivity in CB1R antagonists[112, 113].

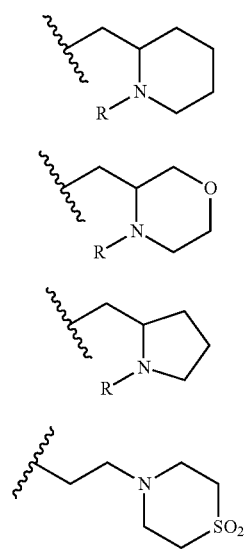

Pharmaceutical Compositions

A further embodiment includes pharmaceutical compositions comprising any compound, discussed herein or pharmaceutically acceptable salts thereof.

In certain embodiments the compositions may include one or more than one compound described herein, and may further contain other suitable substances and excipients, including but not limited to physiologically acceptable buffering agents, stabilizers (e.g. antioxidants), flavoring agents, agents to effect the solubilization of the compound, and the like.

In certain embodiments, the composition may be in any suitable form such as a solution, a suspension, an emulsion, an infusion device, or a delivery device for implantation or it may be presented as a dry powder to be reconstituted with water or another suitable vehicle before use. The composition may include suitable parenterally acceptable carriers and/or excipients.

In certain embodiments, the compositions may comprise an effective amount of a compound in a physiologically-acceptable carrier. The carrier may take a wide variety of forms depending on the form of preparation desired for a particular route of administration. Suitable carriers and their formulation are described, for example, in Remington's Pharmaceutical Sciences by E. W. Martin.

In certain embodiments, the compound may be contained in any appropriate amount in any suitable carrier substance, and is generally present in an amount of 1-95% by weight of the total weight of the composition. The composition may be provided in a dosage form that is suitable for parenteral (e.g., subcutaneously, intravenously, intramuscularly, or intraperitoneally) or oral administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

In certain embodiments, the compositions may be in a form suitable for administration by sterile injection. To prepare such a composition, the compositions(s) are dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, and isotonic sodium chloride solution and dextrose solution. The aqueous formulation may also contain one or more preservatives (e.g., methyl, ethyl or n-propyl p-hydroxybenzoate). For parenteral formulations, the carrier will usually comprise sterile water, though other ingredients, for example, ingredients that aid solubility or for preservation, may be included. Injectable solutions may also be prepared in which case appropriate stabilizing agents may be employed.

Formulations suitable for parenteral administration usually comprise a sterile aqueous preparation of the compound, which preferably is isotonic with the blood of the recipient (e.g., physiological saline solution). Such formulations may include suspending agents and thickening agents and liposomes or other microparticulate systems which are designed to target the compound to blood components or one or more organs. The formulations may be presented in unit-dose or multi-dose form.

Parenteral administration may comprise any suitable form of systemic delivery or localized delivery. Administration may for example be intravenous, intra-arterial, intrathecal, intramuscular, subcutaneous, intramuscular, intra-abdominal (e.g., intraperitoneal), etc., and may be effected by infusion pumps (external or implantable) or any other suitable means appropriate to the desired administration modality.

In certain embodiments, the compositions may be in a form suitable for oral administration. In compositions in oral dosage form, any of the usual pharmaceutical media may be employed. Thus, for liquid oral preparations, such as, for example, suspensions, elixirs and solutions, suitable carriers and additives include water, glycols, oils, alcohols, flavoring agents, preservatives, coloring agents and the like. For solid oral preparations such as, for example, powders, capsules and tablets, suitable carriers and additives include starches, sugars, diluents, granulating agents, lubricants, binders, disintegrating agents and the like. If desired, tablets may be sugar coated or enteric coated by standard techniques.

Compositions suitable for oral administration may be presented as discrete units such as capsules, cachets, tablets, or lozenges, each containing a predetermined amount of the compound as a powder or granules. Optionally, a suspension in an aqueous liquor or a non-aqueous liquid may be employed, such as a syrup, an elixir, an emulsion, or a draught. Formulations for oral use include tablets containing active ingredient(s) in a mixture with pharmaceutically acceptable excipients. Such formulations are known to the skilled artisan. Excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

A syrup may be made by adding the compound to a concentrated aqueous solution of a sugar, for example sucrose, to which may also be added any accessory ingredient(s). Such accessory ingredient(s) may include flavorings, suitable preservative, agents to retard crystallization of the sugar, and agents to increase the solubility of any other ingredient, such as a polyhydroxy alcohol, for example glycerol or sorbitol.

In some embodiments, the composition may be in a form of nasal or other mucosal spray formulations (e.g. inhalable forms). These formulations comprise purified aqueous solutions of the compound with preservative agents and isotonic agents. Such formulations are preferably adjusted to a pH and isotonic state compatible with the nasal or other mucous membranes. Alternatively, they can be in the form of finely divided solid powders suspended in a gas carrier. Such formulations may be delivered by any suitable means or method, e.g., by nebulizer, atomizer, metered dose inhaler, or the like.

In some embodiments, the composition may be in a form suitable for rectal administration. These formulations may be presented as a suppository with a suitable carrier such as cocoa butter, hydrogenated fats, or hydrogenated fatty carboxylic acids.

In some embodiments, the composition may be in a form suitable for transdermal administration. These formulations may be prepared by incorporating the compound in a thixotropic or gelatinous carrier such as a cellulosic medium, e.g., methyl cellulose or hydroxyethyl cellulose, with the resulting formulation then being packed in a transdermal device adapted to be secured in dermal contact with the skin of a wearer.

In addition to the aforementioned ingredients, compositions of the invention may further include one or more accessory ingredient(s) selected from encapsulants, diluents, buffers, flavoring agents, binders, disintegrants, surface active agents, thickeners, lubricants, preservatives (including antioxidants), and the like.

In some embodiments, compositions may be formulated for immediate release, sustained release, delayed-onset release or any other release profile known to one skilled in the art.

In some embodiments, the pharmaceutical composition may be formulated to release the compound substantially immediately upon administration or at any predetermined time or time period after administration. The latter types of compositions are generally known as controlled release formulations, which include (i) formulations that create a substantially constant concentration of the drug within the body over an extended period of time; (ii) formulations that after a predetermined lag time create a substantially constant concentration of the drug within the body over an extended period of time; (iii) formulations that sustain action during a predetermined time period by maintaining a relatively constant, effective level in the body with concomitant minimization of undesirable side effects associated with fluctuations in the plasma level of the active substance (sawtooth kinetic pattern); (iv) formulations that localize action by, e.g., spatial placement of a controlled release composition adjacent to or in the central nervous system or cerebrospinal fluid; (v) formulations that allow for convenient dosing, such that doses are administered, for example, once every one or two weeks; and (vi) formulations that target the site of a pathology. For some applications, controlled release formulations obviate the need for frequent dosing to sustain activity at a medically advantageous level.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the compound is formulated with appropriate excipients into a pharmaceutical composition that, upon administration, releases the compound in a controlled manner. Examples include single or multiple unit tablet or capsule compositions, oil solutions, suspensions, emulsions, microcapsules, microspheres, molecular complexes, nanoparticles, patches, and liposomes.

In some embodiments, the composition may comprise a "vectorized" form, such as by encapsulation of the compound in a liposome or other encapsulate medium, or by fixation of the compound, e.g., by covalent bonding, chelation, or associative coordination, on a suitable biomolecule, such as those selected from proteins, lipoproteins, glycoproteins, and polysaccharides.

In some embodiments, the composition can be incorporated into microspheres, microcapsules, nanoparticles, liposomes, or the like for controlled release. Furthermore, the composition may include suspending, solubilizing, stabilizing, pH-adjusting agents, tonicity adjusting agents, and/or dispersing, agents. Alternatively, the compound may be incorporated in biocompatible carriers, implants, or infusion devices.

Materials for use in the preparation of microspheres and/or microcapsules are, e.g., biodegradable/bioerodible polymers such as polygalactin, poly-(isobutyl cyanoacrylate), poly(2-hydroxyethyl-L-glutamine) and, poly(lactic acid). Biocompatible carriers that may be used when formulating a controlled release parenteral formulation are carbohydrates (e.g., dextrans), proteins (e.g., albumin), lipoproteins, or antibodies. Materials for use in implants can be non-biodegradable (e.g., polydimethyl siloxane) or biodegradable (e.g., poly(caprolactone), poly(lactic acid), poly (glycolic acid) or poly(ortho esters) or combinations thereof).

Unless the context clearly indicates otherwise, compositions of all embodiments can comprise various pharmaceutically acceptable salts, ether derivatives, ester derivatives, acid derivatives, and aqueous solubility altering derivatives of the compound. Certain embodiments can comprise all individual enantiomers, diastereomers, racemates, and other isomer of compounds of the invention. The invention also includes all polymorphs and solvates, such as hydrates and those formed with organic solvents, of this compound. Such isomers, polymorphs, and solvates may be prepared by methods known in the art, such as by regiospecific and/or enantioselective synthesis and resolution, based on the disclosure provided herein.

Suitable salts of the compound include, but are not limited to, acid addition salts, such as those made with hydrochloric, hydrobromic, hydroiodic, perchloric, sulfuric, nitric, phosphoric, acetic, propionic, glycolic, lactic pyruvic, malonic, succinic, maleic, fumaric, malic, tartaric, citric, benzoic, carbonic cinnamic, mandelic, methanesulfonic, ethanesulfonic, hydroxyethanesulfonic, benezenesulfonic, p-toluene sulfonic, cyclohexanesulfamic, salicyclic, p-aminosalicylic, 2-phenoxybenzoic, and 2-acetoxybenzoic acid; salts made with saccharin; alkali metal salts, such as sodium and potassium salts; alkaline earth metal salts, such as calcium and magnesium salts; and salts formed with organic or inorganic ligands, such as quaternary ammonium salts.

Additional suitable salts include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate salts of the compound of the present invention.

The formulation and preparation of such compositions are well known to those skilled in the art of pharmaceutical formulation. Formulations can be found in Remington: The Science and Practice of Pharmacy.

Methods of Treatment

A further embodiment includes uses of compounds described herein for treating a disease in a subject. Embodiments include methods for treating a disease by administering a subject a therapeutically effective amount of a compound described herein.

Embodiments include methods for treating a disease or disorder in a subject comprising administering to a subject a compound described herein, wherein the disease or disorder may be treated by activating or blocking a peripheral cannabinoid receptor.

Other potential therapeutic applications for peripherally-acting CB1R ligands include: 1) pain symptoms of rheumatoid arthritis, inflammatory bowel disorders, soft tissue and bone cancer pain, and chemotherapy-induced neuropathy, particularly since classical CBs have been shown to ameliorate the pain symptoms of cancer and chemotherapy-induced neuropathies mainly by peripheral mechanisms[161-168]; 2) decreasing intraocular pressure in glaucoma resistant to conventional therapies[169]; 3) anti-emetic and anti-nausea actions via CB1R activation in area postrema, which are located outside the blood-brain barrier[170]; 4) antidiarrheal actions[171]; 5) antitumorigenic actions[172]; and 6) treatment of bone diseases associated with accelerated osteoclastic bone resorption including osteoporosis, rheumatoid arthritis and bone metastasis[173].

In some embodiments, the compound has less than about 10% permeability across the blood brain barrier, as measured using the Madin-Darby canine kidney cell line assay. In some embodiments, the compound has less than about 7% permeability, less than about 5% permeability, less than about 4% permeability, less than about 3% permeability, less than about 2% permeability or less than about 1% permeability across the blood brain barrier, as measuring using the Madin-Darby canine kidney cell line assay. In some embodiments, the disorder is pain. The pain may be chronic, inflammatory, or neuropathic. In some embodiments, the disease or disorder is hyperalgesia or allodynia, and the compound alleviates the symptoms of hyperalgesia or allodynia.

In some embodiments, the disease or disorder is one or more of rheumatoid arthritis, inflammatory bowel disorders, soft tissue pain, bone cancer pain, chemotherapy-induced neuropathy, pain caused by thermal injury, pain caused by nerve injury, and pain caused by cancer. In some embodiments, the disease or disorder is intraocular pressure. In some embodiments, the disease or disorder is a tumor.

In some embodiments, the compound acts an anti-emetic, or anti-nausea agent.

In some embodiments, the disease or disorder is a bone disease associated with accelerated bone resorption. Examples include osteoporosis, rheumatoid arthritis, or bone metastasis.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

EXAMPLES

Ligand Screening Assays

Compounds were first screened for: a) CB1R and CB2R binding, b) CB1R agonist activity using the human CB1R (hCB1R) calcium flux assay, and c) BBB permeability using the Madin-Darby canine kidney (MDCK-MDR1) cell line assay. Results are shown in Table 1. Compounds 1, 19, 39, 42, 44, 69, 70 are standards. After identifying ligands with high affinity and agonist activity at CB1Rs and low BBB permeability, ligands were tested for stability in rat plasma and in the rat S9 fraction. Results are shown in Table 2. Subsequently, the most promising candidate compounds were tested in rat models of chronic inflammatory and neuropathic pain. Results are shown in Table 3.

Example 1

In Vitro Assays

1) CB1/CB2R Binding Assays.
Detailed radioligand displacement assays (using the well-characterized CBR agonist CHFCP55940 as the radioligand) were conducted to determine the affinity (Ki) of the test compounds for CB1R and CB2R as has been previously described by our group[112,113]. Heterologous competition binding assays were performed to calculate receptor affinities. Unlabeled SR141716 or SR144528 were used as appropriate controls for non-specific binding (NSB) in the assay. Calculation of the equilibrium dissociation constant (Ki) was performed using the Cheng-Prusoff equation.

2) Calcium Flux Assay.
The calcium 3 dye assays were run according to manufacturer's specifications (http://www.moleculardevices.com/Products/Assay-Kits/GPCRs/FLIPR-Calcium.html) and as reported in our previous publications[112,113]. Briefly, wells of black clear-bottom 96-well tissue culture-treated plates are seeded with 20,000 cells the afternoon before assay. The day of assay, the cells are incubated with the $Ca^{2+}$ indicator dye for 1 hr @ 37° C. For antagonist assays, the test compound is preincubated with the cells during the last 10 min of the dye incubation. Basal or unstimulated fluorescence intensity is recorded in the FlexStation @ 37° C. for 13 sec followed by the addition of test compound or CP 55,940 (depending on the assay endpoint). Fluorescence intensity is recorded for an additional 47 sec. The effect of test compound in each well is determined by subtracting the minimum from the maximum fluorescence during the 47-sec recording period.

3) Permeability Assay.
Potential substrates for crossing the BBB and apparent permeability (Papp) are assessed for various new chemical entities (NCEs) using the MDCK-MDR1 epithelial cell line. Papp of a compound in this particular model is defined as the rate of flux of a molecule across the monolayer and is predictive of potential blood brain barrier penetration[114]. In a typical assay, cells are grown to confluence on Transwell™ filters and the test compound added to the apical side in a transport buffer. Following incubation for 1 hr at 37° C., samples are collected from both compartments and analyzed for transport using LC-MS/MS. Cells are plated onto semipermeable membranes in a system. NCE is dissolved in dimethyl sulfoxide or ethanol. For screening purposes, two concentrations of NCE are assessed, typically 3 µM and 10 µM, each for 60 min, in triplicate for both concentrations. Samples are analyzed by HPLC. Results are reported as a Papp value and NCEs are rank ordered accordingly.

4) Plasma Stability Assay.
Compounds are incubated at 10 µM in rat plasma at 37° C. A solution of each compound is prepared in ethanol at a concentration of 1 mM. A 2.5 µL volume of the 1 mM solution is added to 247.5 µL of rat plasma (male Sprague Dawley) in a glass test tube in a 37° C. water bath. Samples (50 µL) are removed at 0, 30 and 60 min and immediately extracted with 3 volumes (150 µL) of methanol. Samples are centrifuged (2500 rpm for 10 min at 4° C.) to pellet protein and supernatants transferred to LC/MS vials for analysis. Samples are stored at −80° C. prior to analysis.

5) S9 Fraction Stability Assay.
Compounds are incubated at 10 µM in rat (male Sprague Dawley) liver S9 at 37° C. Each compound is prepared in ethanol at a concentration of 1 mM. An assay mixture containing S9 (1 mg protein/mL final concentration) and an NADPH regenerating system (NADP [1 mM final], glucose 6-phosphate [5 mM final] and glucose 6-phosphate dehydrogenase [1 U/mL final]) in a buffer consisting of 50 mM KPO4 phosphate buffer, pH 7.4 with 3 mM MgCl2 is prepared and preincubated at 37° C. for 5 min. A 10 µL volume of the 1 mM solution is added to 990 µL of assay mixture in a glass test tube @ 37° C. to initiate the assay. Samples (50 µL) are removed at 0, 15, 30, 60 and 120 min and immediately extracted with 3 volumes (150 µL) of methanol, centrifuged to pellet protein and supernatants transferred to LC/MS vials for analysis.

Example 2

Indene Synthesis

General Methods
1H and 13C NMR spectra were run on a Bruker Avance 300 MHz or a Varian Unity Inova 500 MHz NMR spectrometer. Mass spectra (MS) were run on a Perkin-Elmer Sciex API 150 EX mass spectrometer. High resolution mass spectra (HRMS) were run on a Waters Synapt G2 Q-TOF mass spectrometer in high-resolution mode. Column chromatography was carried out using a Teledyne Isco Combiflash Rf system with RediSep Rf silica cartridges. Preparative thin layer chromatography was carried out using Analtech TLC Uniplates (silica gel, 1000 µm, 20×20 cm). High pressure liquid chromatography was performed using a system consisting of a Waters 1525 pump unit, driven by Empower software, and a Waters 2487 detector. Microwave chemistry was carried out using a CEM Discover SP microwave with 10 mL irradiation tubes.

Synthesis of ENMI 4-{2-[(1E)-1-(Naphthalen-1-ylmethylidene)-1H-inden-3-yl]ethyl}morpholine (26)

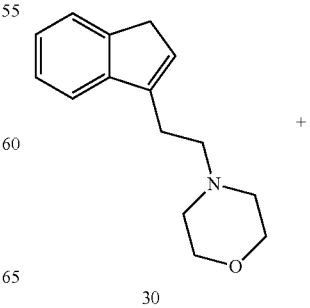

30

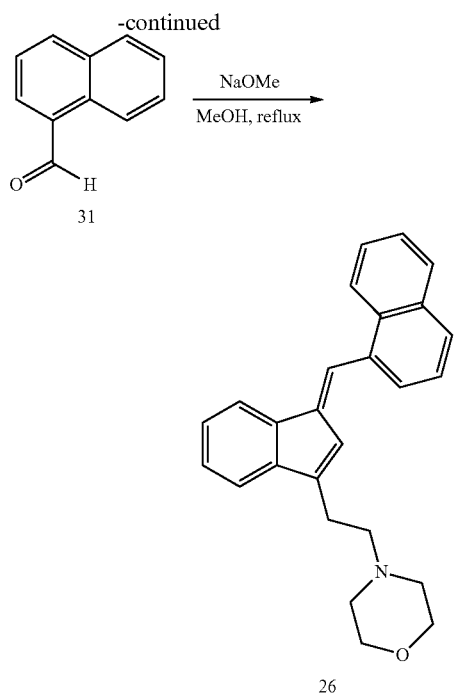

4-[2-(1H-Inden-3-yl)ethyl]morpholine (30) (2.82 g, 12.3 mmol) was dissolved in methanol (75 mL) and cooled in a ice bath to 0° C. The reaction mixture was purged with nitrogen and sodium methoxide (25.8 mL, 0.5M in MeOH; 1.22 mmol) was added dropwise over 5 minutes and the solution stirred at room temperature for 30 minutes. Naphthaldehyde (31) (1.67 mL, 12.3 mmol) was then added dropwise over several minutes. After the addition was complete, the solution was stirred under reflux for 18 hours. At the end of this time the mixture was allowed to cool to room temperature. The resulting solid was removed by filtration and recrystallized from methanol to give a golden solid (2.2 g). The original filtrate and the filtrate from the recrystallization were combined and the solvent removed. This residue was recrystallized twice from methanol to give a golden solid which was combined with the initial recrystallization product (780 mg, 2.98 g total, 65.9%). $^1$H NMR (300 MHz, CDCl$_3$) δ 2.41 (t, J=4.2 Hz, 4H), 2.54-2.64 (m, 2H), 2.71-2.82 (m, 2H), 3.56 (t, J=4.5 Hz, 4H), 3H), 6.67 (s, 1H), 7.26-7.41 (m, 3H), 7.55-7.71 (m, 4H), 7.93-8.08 (m, 3H), 8.22-8.31 (m, 2H). $^{13}$C NMR (75.5 MHz, CDCl$_3$) δ 24.65, 53.15 (2C), 56.74, 66.20 (2C), 118.76, 119.86, 122.11, 124.44, 124.52, 125.32, 125.65, 126.22, 126.55, 127.54, 128.47, 128.51, 128.87, 131.58, 133.21, 133.54, 137.31, 140.67, 142.28, 146.74. HPLC 99.8% (Waters X-Bridge C-18 5 μm, 4.6×100 mm column, 10 mM aqueous NH$_4$OAc—CH$_3$CN, 40:60, UV detection at 254 nm). HRMS: Calculated for C$_{26}$H$_{26}$NO (M+H): 368.2014. Found: 368.2013 (M+H).

Example 3

Indole Synthesis

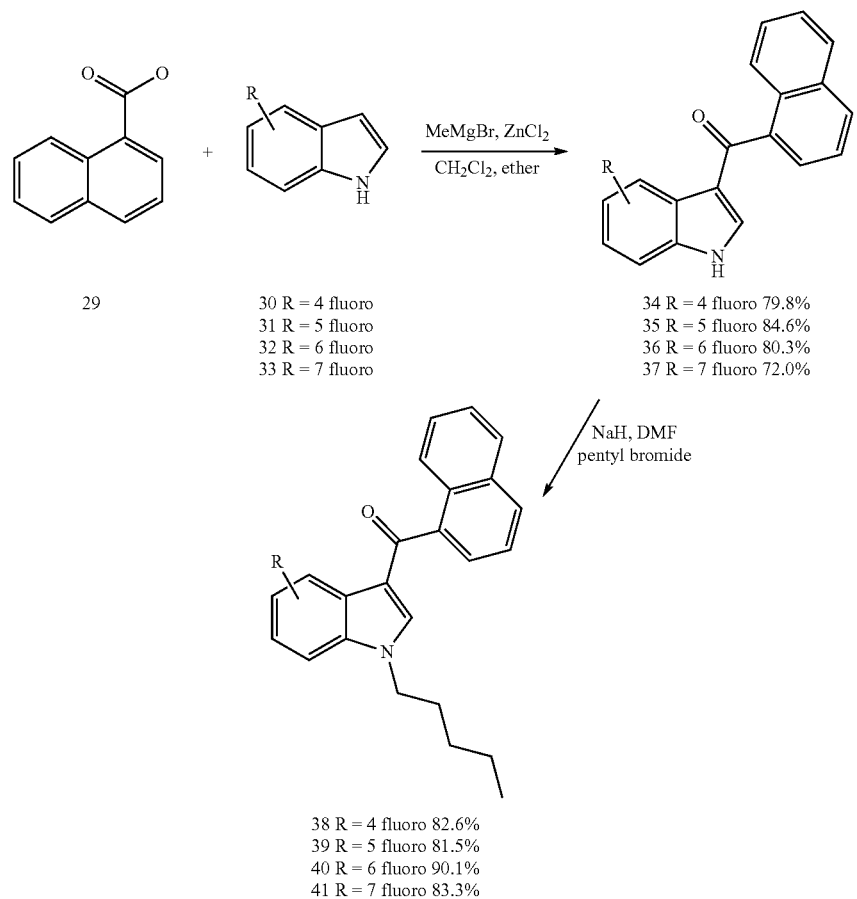

Synthesis of 6-Fluoro-3-[(naphthalen-1-yl)carbonyl]-1-pentyl-1H-indole (40)

Sodium hydride (207 mg, 60% in oil, 5.18 mmol) was added to DMF (20 mL) at 0° C. and the mixture stirred for 10 minutes. A solution of 6-fluoro-3-[(naphthalen-1-yl)carbonyl]-1H-indole (36) (750 mg, 2.59 mmol) in DMF (10 mL) was added dropwise over 5 minutes and the resulting solution stirred at 0° C. for 30 minutes. A solution of 1-bromopentane (431 mg, 2.85 mmol) in DMF (1 mL) was then added dropwise to the stirred mixture. Cooling was continued for an additional 10 minutes before allowing the solution to warm to room temperature and stir overnight. The reaction was quenched with water (75 mL), and EtOAc (50 mL) was added. The mixture was shaken and the organic layer removed. The aqueous layer was then extracted with additional EtOAc (50 mL). The organic layers were combined, dried over $Na_2SO_4$ and the solvent removed under reduced pressure. The residue was purified over silica gel (Isco, 120 g column, gradient from 100% hexane to 30% EtOAc/70% hexane) to give the title compound as a colorless resin (840 mg, 90.1%). $^1$H NMR (300 MHz, $CDCl_3$) δ 0.85 (t, J=6.8 Hz, 3H), 1.18-1.40 (m, 4H), 1.72-1.87 (m, 2H), 4.00 (t, J=7.2 Hz, 2H), 7.02-7.16 (m, 2H), 7.32 (s, 1H), 7.43-7.58 (m, 3H), 7.61-7.69 (m, 1H), 7.87-7.95 (m, 1H), 7.98 (d, J=8.2 Hz, 1H), 8.14-8.22 (m, 1H), 8.39-8.48 (m, 1H). $^{13}$C NMR (75.5 MHz, CDCl3) δ 13.82, 22.15, 28.88, 29.35, 47.32, 96.64 (d, J=26.6 Hz, 1C), 111.34 (d, J=23.9 Hz, 1C), 117.70, 123.38, 124.09 (d, J=9.9 Hz, 1C), 124.51, 125.91 (d, J=2.6 Hz, 1C), 126.35, 126.83, 128.21, 130.13, 130.80, 133.79, 137.31 (d, J=11.7 Hz, 1C), 138.13 (d, J=2.6 Hz, 1C), 138.83, 160.57 (d, J=241.0 Hz, 1C), 191.88. HPLC 98.7% (Waters X-Bridge C-18 5 μm, 4.6×100 mm column, $H_2O$—$CH_3CN$, 35:65, UV detection at 254 nm). HRMS: Calculated for $C_{24}H_{23}NOF$ (M+H): 360.1764. Found: 360.1758 (M+H).

Example 4

Repeated Systemic Treatment with Different Novel Compounds with Agonist Activity at CB1 Receptors Reversibly Attenuates Symptoms of Mechanical Allodynia in a Rat Model of Neuropathic Pain The effectiveness of CBR agonists was tested for alleviating the painful symptoms of neuropathy induced by unilateral sciatic nerve entrapment (SNE)[131]. The peripheral neuropathy induced by SNE is highly comparative to that of chronic constriction injury (CCI), which uses chromic gut suture materials instead of polyethylene cuffs[132]. SNE was demonstrated to produce consistent pain behaviors[131, 133], a bona fide transient loss of varicosities in nociceptive fibers[134], and increases in evoked excitability of sciatic nerve compound action potentials[135]. This increased excitability is at least in part attributable to injury-induced post-transcriptional transport of the voltage-gated sodium channel 1.8 (NaV1.8) mRNA, axonal accumulation of NaV1.8 mRNA, and its local protein translation leading to the increased NaV1.8 functional expression in injured nerve[136]. The hyperexcitability and ectopic burst discharge of primary sensory neurons are widely considered to be the major contributors to pain symptomatology of peripheral neuropathy models. The SNE-induced mechanical allodynia effectively models the most common complaint of human neuropathy patients of dynamic mechanical allodynia.

Behavioral measurements of mechanical sensitivity were conducted before and after induction of SNE as follows:

Mechanical Sensitivity Testing.

Rats are placed in a plastic-walled cage (10×20×13 cm) with a metal mesh floor (0.6×0.6 cm holes) and allowed to acclimate for 10 min. The amount of pressure (g) needed to evoke a hindpaw withdrawal response is measured 4 times on each paw separated by 30-s intervals using a von Frey-type digital meter (Model 1601C, IITC Instr.). Results of 4 tests/session are averaged for each paw.

FIG. 1 illustrates that systemic injection of 13339-145-35 (4-{2-[-(1E)-1[(4-propylnaphthalen-1-yl)methylidene]-1H-inden-3-yl]ethyl}morpholine, compound 9 in Table 1, 0.3 mg/kg) results in large, reversible increases in the hindpaw withdrawal thresholds ipsilateral to SNE injury. The investigator performing the behavioral tests was blind to the dose or nature of the drug treatments.

Figure 2:
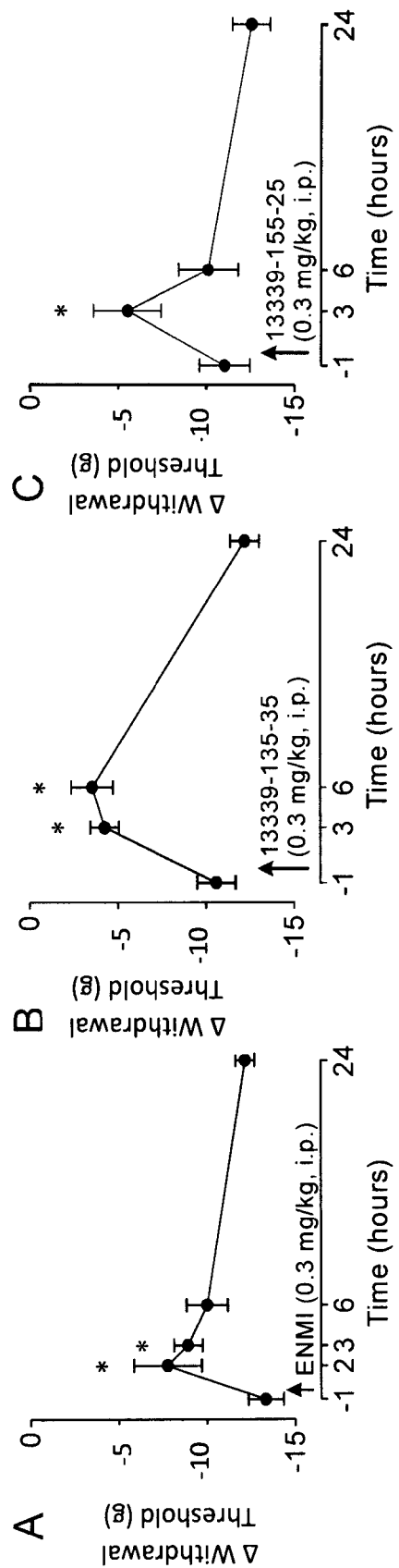
FIG. 2 shows the effect of ENMI, 13339-135-35, and 13339-155-35 on SNE-induced mechanical allodynia. A: Graph of differences in hindpaw withdrawal thresholds (ipsilateral-contralateral) before and after ENMI administration. Data are presented as mean±SEM, n=7 rats). B: Graph of differences in hindpaw withdrawal thresholds (ipsi-contra) before and after 13339-135-25 administration. C: Graph of differences in hindpaw withdrawal thresholds (ipsi-contra) before and after 13339-155-25 administration. *, $p<0.05$ from pre-drug values (one-way ANOVA). Neither ENMI nor 13339-135-25 had any significant effect on contralateral hindpaw thresholds (data not shown). These data demonstrate that our novel CBR ligands repeatedly and reversibly attenuate mechanical allodynia symptoms of peripheral neuropathy.

In the same group of rats we also tested several other novel CB1R ligands (at 3 day intervals) for effectiveness against symptoms of mechanical allodynia. FIG. 2 illustrates the anti-allodynic effects of ENMI (4-E-[2-[1-(1-Naphthalenylmethylene)-1H-inden-3-yl]ethyl]morpholine), whose synthesis and structure were previously reported 6, 13339-135-35 (Compound 10 in Table 1) (4-{2-[-(1E)-1 [(4-methoxynaphthalen-1-yl)methylidene]-1H-inden-3-yl] ethyl}morpholine), and 13339-155-55, 6-fluoro-3-(naphthalene-1-carbonyl)-1-pentyl-1H-indole, (Compound 64 in Table 1) each at 0.3 mg/kg.

Example 5

At Systemic Doses that Relieve Neuropathy Symptoms CBR Agonists Show a Complete Lack of Side Effects in the Assays that Test for CNS-Mediated Side Effects of Catalepsy, Hypothermia and Motor Incoordination The CNS-mediated psychotropic actions of CB1R ligands represent their most troubling side effects. The cannabinoid agonists such as Δ9-THC or anandamide produce a complex pattern of behavioral effects which are unique to this class of compounds: at low doses a mixture of stimulatory and depressant effects is observed, while at higher doses central depression predominates[137,138]. The tetrad of tests which is classically predictive of cannabinoid receptor activation includes: catalepsy, motor performance, hypothermia, and analgesia tests[139-141]. Effects observed in all four tests have been thought to be mediated by the activation of central CBRs, but it is now well established that peripheral CBRs make a major contribution to the analgesic effects of cannabinoids[142-144]. The catalepsy and motor deficits induced by CB1R ligands are likely produced by their action on CB1Rs within the basal ganglia and cerebellum, while hypothermia is thought to be mediated mainly through hypothalamic and brainstem CB1Rs[137, 145-150]. If the novel analgesic compounds possess activity consistent with activation of central CB1Rs this could limit their usefulness as clinical analgesics. Therefore, "tetrad" tests were used to determine whether the novel CB1R ligands have antinociceptive effects and side-effect profile consistent with the activation of central CB1Rs. We first studied the potent CB1R agonist, HU-210, to determine its CNS actions in order to allow comparisons of this positive control with the putatively brain-impermeant analogs which we developed. The experiments were performed using the classic "tetrad" tests modified for rats, with rotarod substituting for the spontaneous activity test as follows:

Tail-Flick Test.

A modified Hargreaves apparatus (Model 390, IITC Instr.) is used to measure tail-flick latency (TFL). Radiant heat is directed to a point 3 cm from the tail tip and the TFL observed and timed with a photo cell counter. The intensity of the radiant heat is adjusted for a baseline TFL of approximately 5-7 seconds for naïve rats, with a 25 s cutoff set to avoid tissue damage (see FIG. 3).

Rotarod.

Rats were tested for motor function and the ataxic effects of novel drugs as described previously[151-153]. To determine drug effects on motor coordination, rats are trained 72 h before the test (3 sessions 24 h apart) to remain for at least 180 s on a rotarod revolving at an acceleration of 4-40 revs over 5 min). Rats are tested immediately before vehicle or drug injections and tested again at 2, 6, 24 and 48 hrs after injection. The time for which the rats are able to remain on the rotarod is recorded up to a cut-off of 5 min.

Hypothermia.

Rats are acclimated to a plastic restrainer apparatus (Model RTV-180 Braintree Scientific Inc.) on the day of testing by placing them in the restrainer twice for 5 min separated by 20 min. Baseline core temperature is taken before treatment, and the rectal temperature is measured again at various times after injection of the CB1R ligands.

Catalepsy (ring) test. Catalepsy was determined with a ring immobility test[154], modified for rats[139, 153]. Rats are placed with their forepaws on a horizontal metal ring (12 cm diameter) at a height that allows their hindpaws to just touch the bench surface. Immobility is recorded as the time for the rat to move off the ring with a 100 s cutoff. Rats are tested before vehicle/drug injections and again at various times after injection.

We used systemic doses of HU-210 consistent with its demonstrated effectiveness in alleviating painful neuropathy symptoms after peripheral or systemic injection (FIG. 3)[153].

Figure 3:
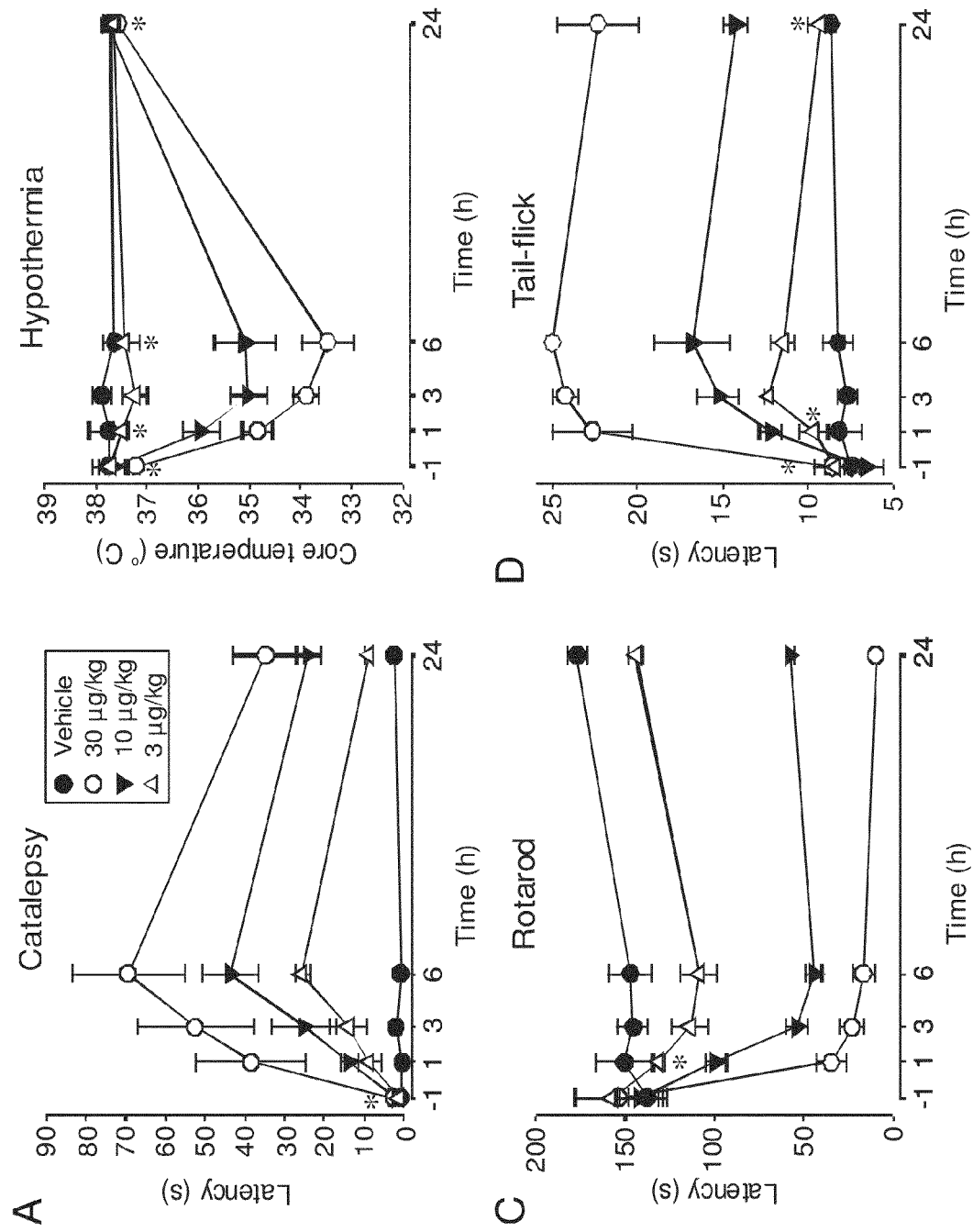
FIG. 3 shows the CNS effects of HU-210 in the "Tetrad" of catalepsy, hypothermia, rotarod and tail-flick tests.

FIG. 3. Activity of HU-210 (i.p.) in the: (A) catalepsy, (B) hypothermia, (C) rotarod, and (D) tail-flick assays. Rats were tested in each assay 1 h prior and up to 24 h following intraperitoneal injection of HU-210 or vehicle. (A-D) Data points represent the mean±SEM from six rats/treatment group. For all points, p<0.05, except *, p>0.05 compared to time-matched vehicle group (two-way RM ANOVA with Tukey's post hoc test).

These data show the potent CNS side effects of the brain-permeant cannabinoid HU-210 in the "tetrad" assays at doses which are effective in relieving painful symptoms of peripheral neuropathy.

Figure 4:
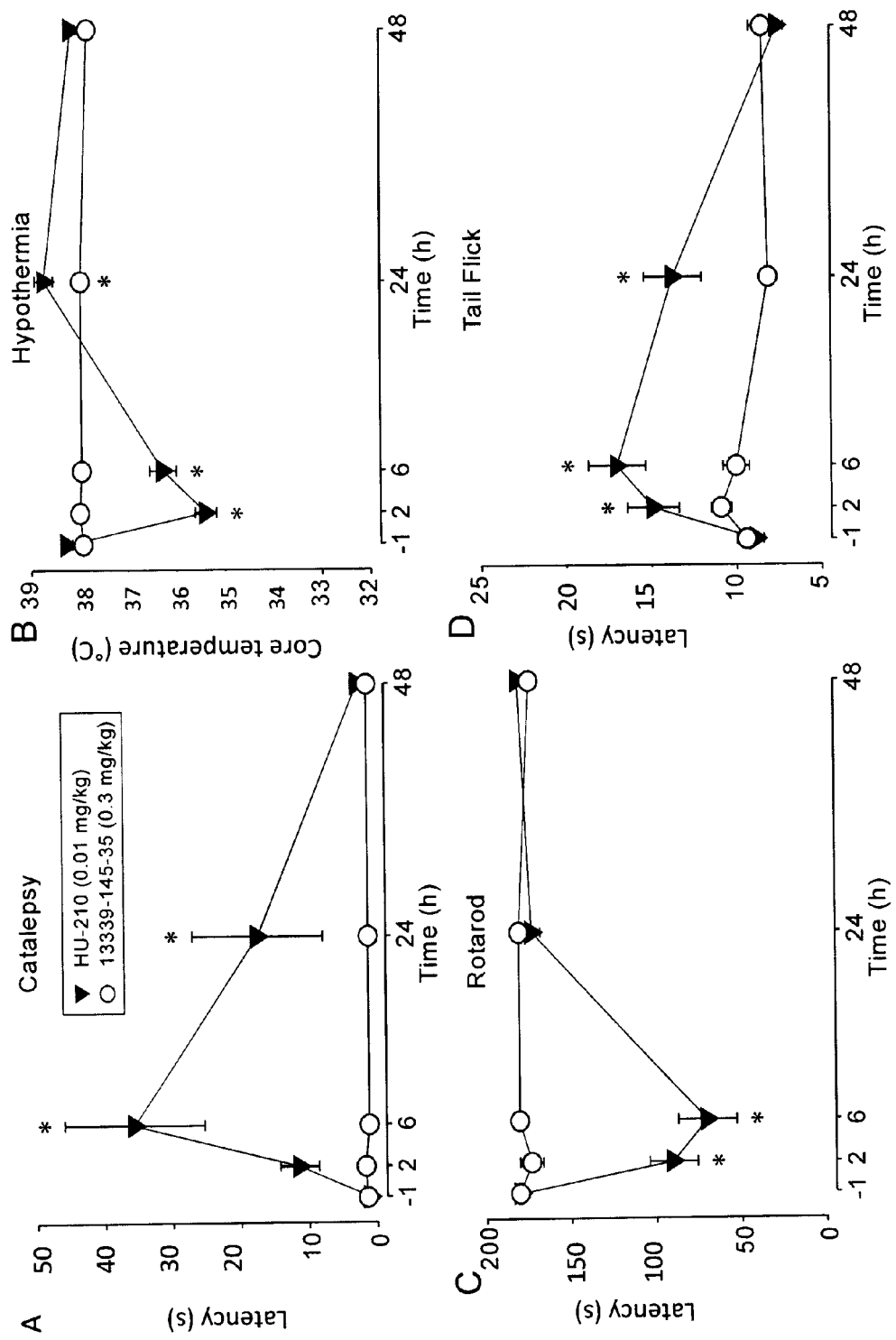
FIG. 4 shows the CNS effects of HU-210 and 13339-145-35 in the "Tetrad" of catalepsy, hypothermia, rotarod and tail-flick tests.

The activity of CBR ligands were tested in the "tetrad" assays using the 0.3 mg/kg doses which were effective in reversibly attenuating mechanical allodynia symptoms of peripheral neuropathy (see FIGS. 1 and 2). As before, rats were trained in the "tetrad" assays for 5 days and the investigator performing the assays was blind to the nature and dose of the drug treatments. In this new set of eight rats we also tested a 10 mg/kg dose of HU-210 as a positive control. FIG. 4 illustrates that unlike HU-210, the novel compound 13339-145-35 has no effect in the catalepsy, rotarod or hypothermia assays, although a small effect in the tail-flick assay is observed, as expected for an analgesic peripherally-acting CB1R ligand.

FIG. 4 shows activity of HU-210 (10 µg/kg) and 13339-145-35 (Compound 9, Table 1) (0.3 mg/kg) in the: (A) catalepsy, (B) rotarod, (C) tail flick, and (D) hypothermia assays. Rats were tested in each assay 1 h prior to and up to 48 h following intraperitoneal injection. Drugs were tested in the same group of 8 rats at 3 day intervals. (A-D) Data points represent the mean±SEM from eight rats. *, p<0.05 (two-way RM ANOVA).

FIG. 5 shows activity of ENMI (0.3 mg/kg) and 13339-145-35 (0.3 mg/kg) in the: (A) catalepsy, (B) rotarod, (C) tail flick, and (D) hypothermia assays. Rats were tested in each assay 1 h prior to and up to 48 h following intraperitoneal injection. Each drug was tested in the same group of rats at 3 day intervals. (A-D) Data points represent the mean±SEM from eight rats. Note the complete lack of effects in the catalepsy and rotarod assays. A small difference between vehicle and 13339-135-35 was observed at 6 hr post-injection, attributed to the vehicle-induced increases in core temperature at that time point. Also note the small, but significant effects of 13339-135-35 in the tail-flick assay. *, p<0.05 compared to time-matched vehicle group (two-way RM ANOVA). These studies show that at doses that produce significant relief from mechanical allodynia of peripheral neuropathy our novel CB1R ligands are devoid of side effects mediated by central CB1Rs. This represents the first demonstration of a complete dissociation of peripheral analgesic effects from centrally-mediated side effects.

Example 6

Figure 6:
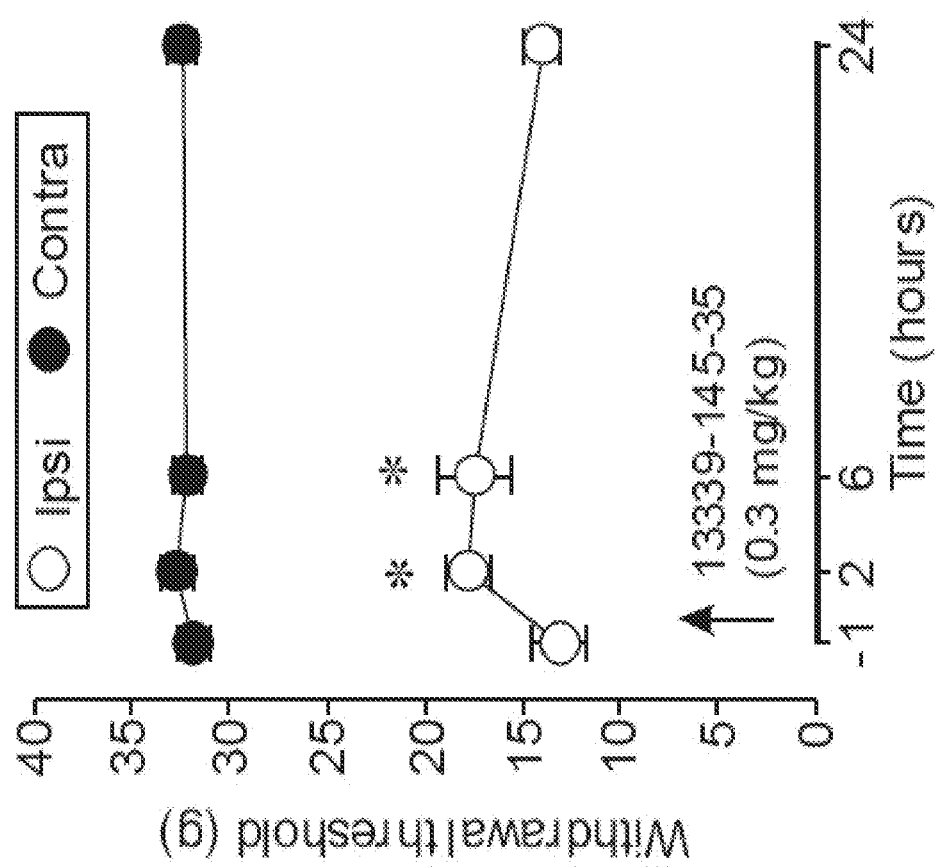
FIG. 6 shows the effect of 13339-145-35 on CFA-induced mechanical allodynia. Graph of ipsilateral and contralateral hindpaw withdrawal thresholds before and after administration of 13339-145-35 (0.3 mg/kg, i.p.). Data are presented as mean±SEM, n=8 rats). *, $p<0.05$ from pre-drug values (one-way ANOVA).

Repeated Treatment with CB1 Receptor Agonists Reversibly Attenuates Symptoms of Mechanical Allodynia in a Rat Model of Chronic Inflammatory Pain Compounds were tested in a well-established model of chronic inflammation. In this model, unilateral intraplantar injection of complete Freund's adjuvant (CFA) leads to long-lasting symptoms of mechanical allodynia and thermal hyperalgesia of the affected hindpaw, which is alleviated by local, but not systemic administration of CB1R ligands[125, 155]. We show that even after systemic injection of our novel CB1R ligands, there is a small but significant relief of mechanical allodynia symptoms (FIG. 6). This is consistent with the higher CB1R affinity of our novel compound 13339-145-35 (Compound 9, see Table 1) compared with the AstraZeneca AZ11713908 compound[125].

Based on the above data, peripherally-acting CBR agonists will be particularly useful in alleviating chronic pain of inflammatory and neuropathic origin. Peripherally-acting CB1R-selective analgesics are unlikely to replace non-steroidal anti-inflammatory analgesics (NSAIAs) and opioids as the mainstay treatment for acute or post-operative pain. Indeed, several studies demonstrated the relatively poor response of cannabinoids in post-operative pain relief[156,157]. However, CB1R-selective analgesics may be a panacea for the treatment of various types of chronic pain in situations where NSAIAs or opioids may be contraindicated. For example, patients with G-I ulcers treated with CB1R agonists could benefit from the demonstrated anti-ulcer effects of cannabinoids[158]. Similarly, asthmatic patients in need of pain relief could benefit from the bronchodilator properties of cannabinoids[159], which are not dependent on prostaglandins[160].

Example 7

Anti-Allodynic Effects of PrNMI in the SNE Neuropathy are Mediated by CB1Rs

Figure 7:
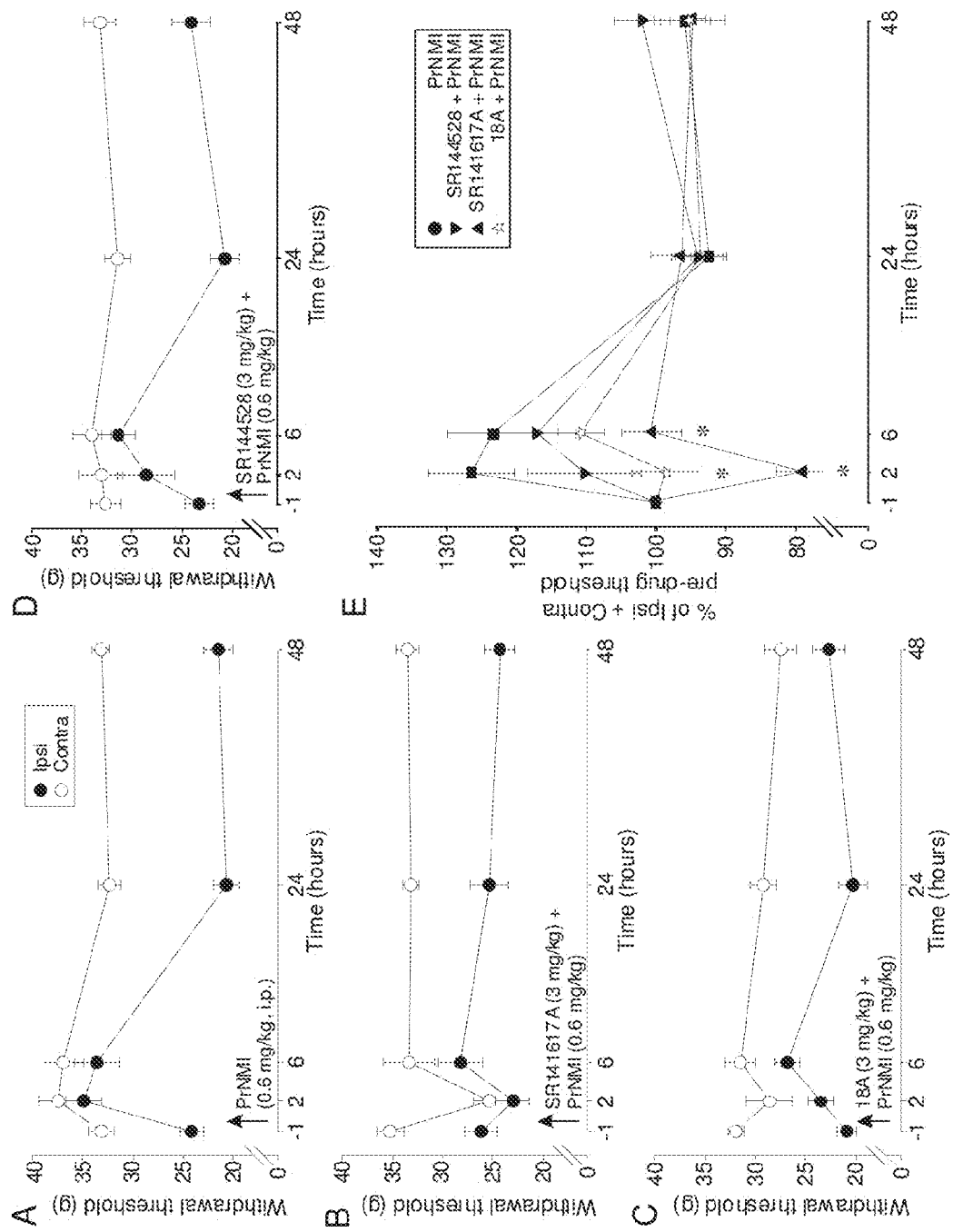
FIG. 7 shows that anti-allodynic effects of PrNMI in the SNE neuropathy are mediated by CB1Rs. A: Suppression of SNE-induced mechanical allodynia by PrNMI (0.6 mg/kg). B: In the same rats (n=8), pre-treatment with the CB1R inhibitor SR141617A (rimonabant, 3 mg/kg, i.p.) completely blocks the response to PrNMI. C: A peripherally-restricted rimonabant analogue, 18A also blocked the response to PrNMI. D. By contrast, the selective CB2R inhibitor SR144528 (3 mg/kg, i.p.) produced only a small decrease in the response to PrNMI. E: Summary of effects of selective CB1R and CB2R inhibition on anti-allodynic effects of PrNMI. *, $p<0.05$ from treatment with PrNMI alone (one-way ANOVA).

The PRCBRLs shown in Table 1 had similar affinities for the CB1Rs and CB2Rs (Table 1). Therefore, it was important to determine which receptor subtype was responsible for the anti-allodynic effects of our the CBR ligands in the SNE neuropathy. To that end, the ability of a representative ligand, 13339-145-35 (PrNMI) to suppress mechanical allodynia in SNE rats in the presence of either CB1R or CB2R selective antagonists was measured. PrNMI was administered alone or after pretreatment with CBR blockers at 3 day intervals in SNE rats. Pretreatment with a CB2R selective inverse agonist, SR144528 had little effect on suppression of allodynia by PrNMI, whereas pretreatment with a CB1R inverse agonist, SR141617A (rimonabant), completely blocked the anti-allodynic effect of PrNMI (FIG. 7). In the same rats, pretreatment with a peripherally-restricted rimonabant analogue, 18A, recently developed by Fulp et al.[113], also prevented the anti-allodynic effect of PrNMI (FIG. 7). These studies demonstrated the CB1R dependence of PrNMI's anti-allodynic effects in the SNE neuropathy. FIG. 7A: Suppression of SNE-induced mechanical allodynia by PrNMI (0.6 mg/kg). FIG. 7B: In the same rats (n=8), pre-treatment with the CB1R inhibitor SR141617A (rimonabant, 3 mg/kg, i.p.) completely blocks the response to PrNMI. FIG. 7C: A peripherally-restricted rimonabant analogue, 18A also blocked the response to PrNMI. FIG. 7D: By contrast, the selective CB2R inhibitor SR144528 (3 mg/kg, i.p.) produced only a small decrease in the response to PrNMI. FIG. 7E: Summary of effects of selective CB1R and CB2R inhibition on anti-allodynic effects of PrNMI. *, $p<0.05$ from treatment with PrNMI alone (one-way ANOVA).

Example 8

Pharmacokinetic Profiling

Figure 8:
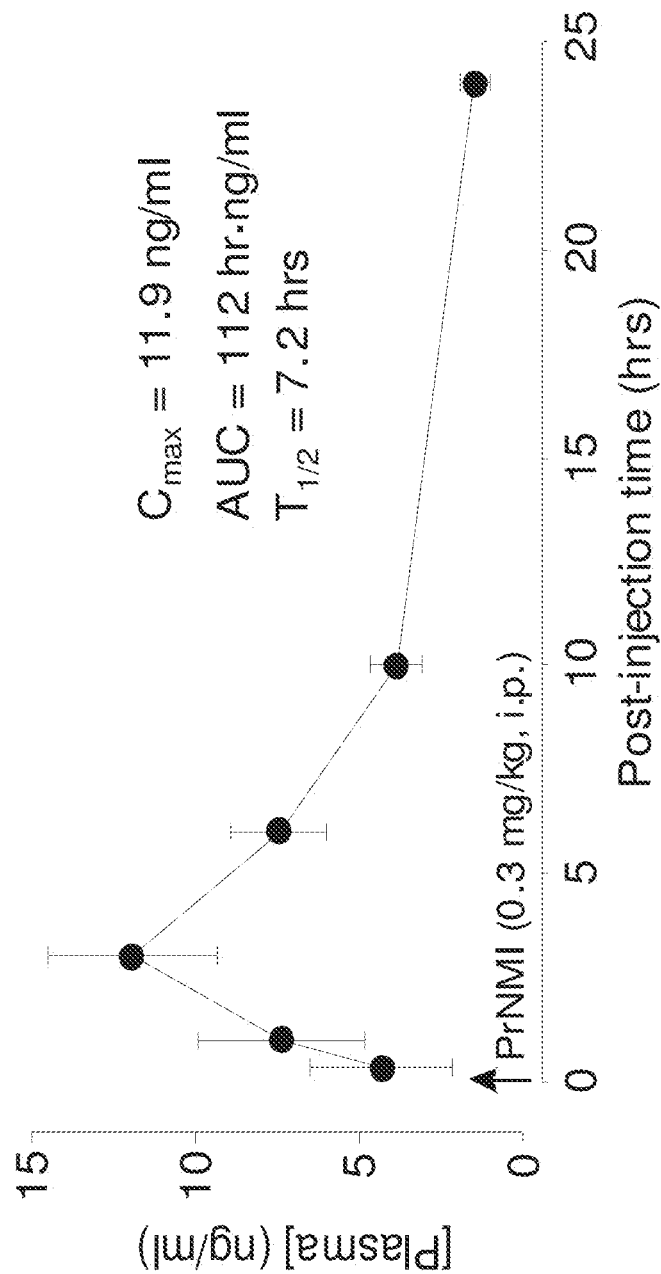
FIG. 8 shows mass spectroscopy analysis of fluid and tissue samples for pharmacokinetic profiling. Data are mean±SEM, n=3 rats.

Pharmacokinetic profiling of novel compounds is prerequisite to their clinical development. Analysis of plasma samples after PrNMI injections provided initial pharmacokinetic profile data (FIG. 8) which was in good agreement with its anti-allodynic effects in the SNE model. Plasma, cerebrospinal fluid (CSF), and brain samples were analyzed by LC-MS/MS and quantified using standard curves prepared from appropriate drug dilutions in fluids obtained from untreated animals.

Measurements of brain levels are a must for putative peripherally-restricted analogs. Total brain levels include drug partitioned into brain lipids+unbound drug in equilibrium with extracellular fluid. Therefore, cerebrospinal fluid (CSF)/plasma ratios are considered to be more precise estimates of brain penetration of a given drug because of the continuity of CSF with extracellular space[174]. However, both measures are needed to confirm minimal CNS access and to compare with other reported peripherally-restricted CB1R ligands[110, 111]. Analysis of plasma, brain and cerebrospinal fluid (CSF) samples confirmed the minimal penetration of PrNMI into the CNS after systemic administration (Table 2). Plasma, brain and CSF samples were obtained at ~75 min after PrNMI administration. Data presented as mean±SEM, n=3 rats.

TABLE 2

| Drug | CSF: Plasma | Brain: Plasma |
| --- | --- | --- |
| PrNMI (0.3 mg/kg, i.p.) | 0.001 ± 0.0005 | 0.182 ± 0.043 |

Example 9

Reversible Suppression of Neuropathy Symptoms by Orally Administered PrNMI

Figure 9:
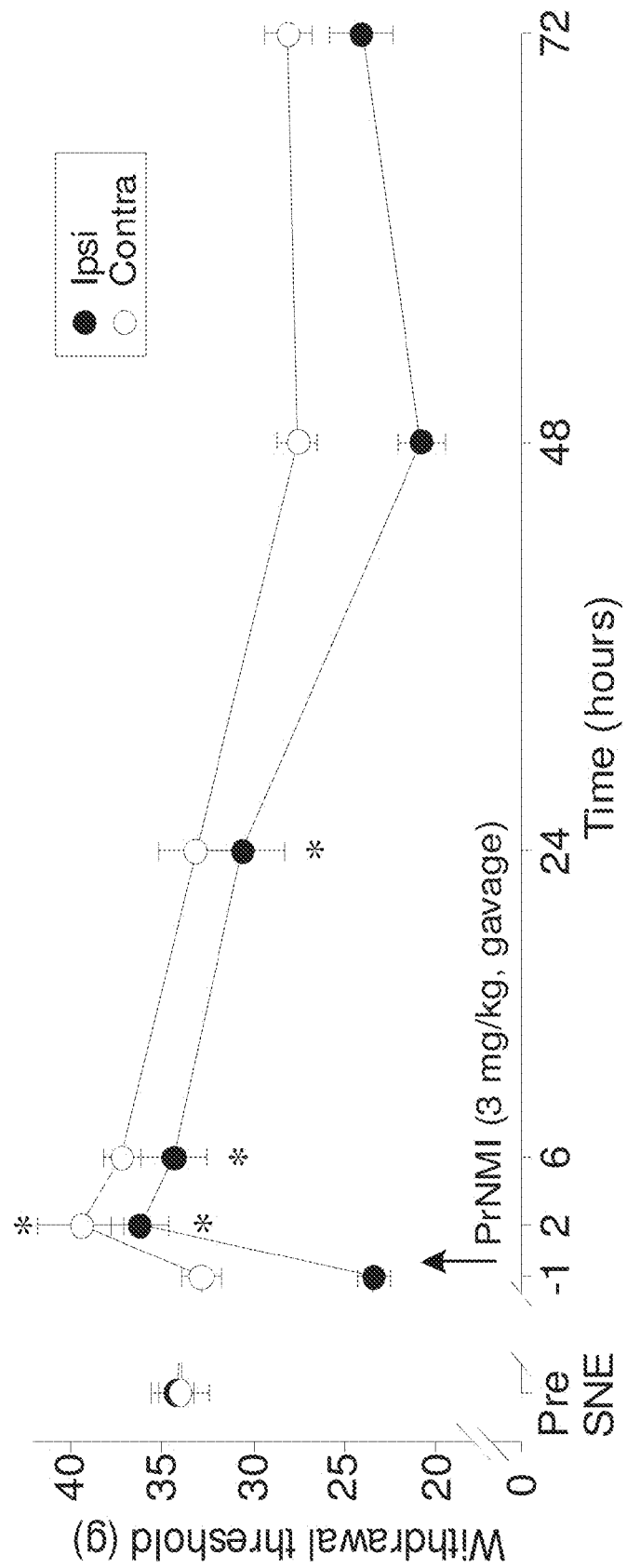
FIG. 9 shows the effect of PrNMI (3 mg/kg, gavage) on SNE-induced mechanical allodynia. Graph of withdrawal thresholds to mechanical stimulation of hindpaws ipsilateral and contralateral to SNE at 1 hr before and 2, 6, 24, 48 and 72 hrs after PrNMI (mean±SEM, n=8 rats). *, $p<0.05$ from pre-drug values (one-way ANOVA).

In other experiments we demonstrated that PrNMI was also effective in suppressing neuropathy symptoms after oral administration. The high oral dose of PrNMI (3 mg/kg) likely accounted for its potent anti-allodynic effects at the 24 hr time point. FIG. 9 shows the effect of PrNMI (3 mg/kg, gavage) on SNE-induced mechanical allodynia. Graph of withdrawal thresholds to mechanical stimulation of hindpaws ipsilateral and contralateral to SNE at 1 hr before and 2, 6, 24, 48 and 72 hrs after PrNMI (mean±SEM, n=8 rats). *, $p<0.05$ from pre-drug values (one-way ANOVA). Note maintained drug effectiveness at 24 hrs.

Example 10

Figure 10:
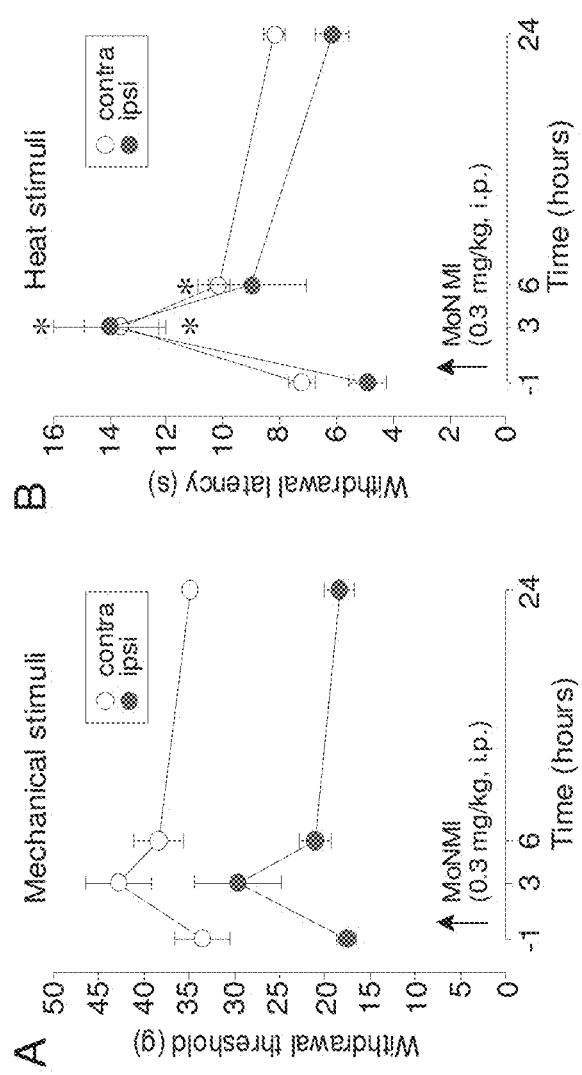
FIG. 10 shows the effect of 13339-135-35 (MoNMI, Compound 10 in Table 1), on CFA-induced mechanical allodynia and heat hyperalgesia. A: Graph of withdrawal thresholds to mechanical stimulation of hindpaws ipsilateral and contralateral to CFA injection. B: Graph of withdrawal latencies to heat stimulation of hindpaws. Data are mean±SEM, n=6 rats. *, $p<0.05$ from pre-drug values (one-way ANOVA).

In another set of rats, we showed that after systemic injection of 13339-135-35 (MoNMI, Compound 10 in Table 1), there was a relatively small effect on mechanical allodynia and robust relief of heat hyperalgesia symptoms (FIG. 10).

Thermal Sensitivity.

The Hargreaves method was used to assess paw-withdrawal latency to a thermal nociceptive stimulus[175]. Rats were acclimated (10 min) within Plexiglas enclosures (10× 20×20 cm) on a clear glass plate preheated to 30° C. A radiant heat source (adjustable infrared lamp) and a timer were used to measure paw withdrawal latency (Model 390, IITC Instruments). Each paw was tested 4 times at 30% maximal intensity allowing 5 min between each test. This intensity setting resulted in a baseline withdrawal of 8-10 s. Results of 4 tests were averaged for each paw for that session.

REFERENCE LIST

1. Herkenham, M., Lynn, A. B., Little, M. D., Johnson, M. R., Melvin, L. S., de Costa, B. R., & Rice, K. C. Cannabinoid receptor localization in brain. *Proc. Natl. Acad. Sci. U.S.A.* 87, 1932-1936 (1990).
2. Mackie, K. Distribution of cannabinoid receptors in the central and peripheral nervous system. *Handb. Exp. Pharmacol.* 299-325 (2005).
3. Spigelman, I Therapeutic targeting of peripheral cannabinoid receptors in inflammatory and neuropathic pain states in Translational Pain Research: from Mouse to Man (eds. Kruger, L. & Light, A. R.) 99-137 (Taylor & Francis Group, LLC, Boca Raton, 2010).
4. Van Sickle, M. D., Oland, L. D., Ho, W., Hillard, C. J., Mackie, K., Davison, J. S., & Sharkey, K. A. Cannabinoids inhibit emesis through CB1 receptors in the brainstem of the ferret. *Gastroenterology* 121, 767-774 (2001).
5. Pertwee, R. G. Pharmacological actions of cannabinoids. *Handb. Exp. Pharmacol.* 1-51 (2005).
6. Mitrirattanakul, S., Ramakul, N., Guerrero, A. V., Matsuka, Y., Ono, T., Iwase, H., Mackie, K., Faull, K., & Spigelman, I. Site-specific increases in peripheral cannabinoid receptors and their endogenous ligands in a model of neuropathic pain. *Pain* 126, 102-114 (2006).
7. Izzo, A. A., Mascolo, N., & Capasso, F. The gastrointestinal pharmacology of cannabinoids. *Curr. Opin. Pharmacol.* 1, 597-603 (2001).
8. Izzo, A. A. & Coutts, A. A. Cannabinoids and the digestive tract. *Handb. Exp. Pharmacol.* 573-598 (2005).

9. Straiker, A. J., Maguire, G., Mackie, K., & Lindsey, J. Localization of cannabinoid CB1 receptors in the human anterior eye and retina. *Invest Ophthalmol. Vis. Sci.* 40, 2442-2448 (1999).
10. Porcella, A., Maxia, C., Gessa, G. L., & Pani, L. The human eye expresses high levels of CB1 cannabinoid receptor mRNA and protein. *Eur. J. Neurosci.* 12, 1123-1127 (2000).
11. Oltmanns, M. H., Samudre, S. S., Castillo, I. G., Hosseini, A., Lichtman, A. H., Allen, R. C., Lattanzio, F. A., & Williams, P. B. Topical WIN55212-2 alleviates intraocular hypertension in rats through a CB1 receptor mediated mechanism of action. *J. Ocul. Pharmacol. Ther.* 24, 104-115 (2008).
12. Lynn, A. B. & Herkenham, M. Localization of cannabinoid receptors and nonsaturable high-density cannabinoid binding sites in peripheral tissues of the rat: implications for receptor-mediated immune modulation by cannabinoids. *J. Pharmacol. Exp. Ther.* 268, 1612-1623 (1994).
13. Galiegue, S., Mary, S., Marchand, J., Dussossoy, D., Carriere, D., Carayon, P., Bouaboula, M., Shire, D., Le Fur, G., & Casellas, P. Expression of central and peripheral cannabinoid receptors in human immune tissues and leukocyte subpopulations. *Eur. J. Biochem.* 232, 54-61 (1995).
14. Griffin, G., Fernando, S. R., Ross, R. A., McKay, N. G., Ashford, M. L., Shire, D., Huffman, J. W., Yu, S., Lainton, J. A., & Pertwee, R. G. Evidence for the presence of CB2-like cannabinoid receptors on peripheral nerve terminals. *Eur. J. Pharmacol.* 339, 53-61 (1997).
15. Onaivi, E. S., Ishiguro, H., Gong, J. P., Patel, S., Perchuk, A., Meozzi, P. A., Myers, L., Mora, Z., Tagliaferro, P., Gardner, E., Brusco, A., Akinshola, B. E., Liu, Q. R., Hope, B., Iwasaki, S., Arinami, T., Teasenfitz, L., & Uhl, G. R. Discovery of the presence and functional expression of cannabinoid CB2 receptors in brain. *Ann. N. Y. Acad. Sci.* 1074:514-36., 514-536 (2006).
16. Hanus, L., Breuer, A., Tchilibon, S., Shiloah, S., Goldenberg, D., Horowitz, M., Pertwee, R. G., Ross, R. A., Mechoulam, R., & Fride, E. HU-308: a specific agonist for CB(2), a peripheral cannabinoid receptor. *Proc. Natl. Acad. Sci. U.S.A* 96, 14228-14233 (1999).
17. Malan, T. P., Jr., Ibrahim, M. M., Deng, H., Liu, Q., Mata, H. P., Vanderah, T., Porreca, F., & Makriyannis, A. CB2 cannabinoid receptor-mediated peripheral antinociception. *Pain* 93, 239-245 (2001).
18. Bisogno, T., Ligresti, A., & Di Marzo, V The endocannabinoid signalling system: biochemical aspects. *Pharmacol. Biochem. Behav.* 81, 224-238 (2005).
19. Chevaleyre, V., Takahashi, K. A., & Castillo, P. E. Endocannabinoid-mediated synaptic plasticity in the CNS. *Annu. Rev. Neurosci.* 29:37-76., 37-76 (2006).
20. Fride, E. & Mechoulam, R. Pharmacological activity of the cannabinoid receptor agonist, anandamide, a brain constituent. *Eur. J. Pharmacol.* 231, 313-314 (1993).
21. Lichtman, A. H. & Martin, B. R. Spinal and supraspinal components of cannabinoid-induced antinociception. *J. Pharmacol. Exp. Ther.* 258, 517-523 (1991).
22. Martin, W. J., Hohmann, A. G., & Walker, J. M. Suppression of noxious stimulus-evoked activity in the ventral posterolateral nucleus of the thalamus by a cannabinoid agonist: correlation between electrophysiological and antinociceptive effects. *J. Neurosci.* 16, 6601-6611 (1996).
23. Smith, P. B., Compton, D. R., Welch, S. P., Razdan, R. K., Mechoulam, R., & Martin, B. R. The pharmacological activity of anandamide, a putative endogenous cannabinoid, in mice. *J. Pharmacol. Exp. Ther.* 270, 219-227 (1994).
24. Sofia, R. D., Nalepa, S. D., Harakal, J. J., & Vassar, H. B. Anti-edema and analgesic properties of delta9-tetrahydrocannabinol (THC). *J Pharmacol Exp Ther* 186, 646-655 (1973).
25. Welch, S. P., Huffman, J. W., & Lowe, J. Differential blockade of the antinociceptive effects of centrally administered cannabinoids by SR141716A. *J. Pharmacol. Exp. Ther.* 286, 1301-1308 (1998).
26. Richardson, J. D., Aanonsen, L., & Hargreaves, K. M. SR 141716A, a cannabinoid receptor antagonist, produces hyperalgesia in untreated mice. *Eur. J. Pharmacol.* 319, R3-R4 (1997).
27. Strangman, N. M., Patrick, S. L., Hohmann, A. G., Tsou, K., & Walker, J. M. Evidence for a role of endogenous cannabinoids in the modulation of acute and tonic pain sensitivity. *Brain Res.* 813, 323-328 (1998).
28. Calignano, A., La Rana, G., Giuffrida, A., & Piomelli, D. Control of pain initiation by endogenous cannabinoids. *Nature* 394, 277-281 (1998).
29. Brusberg, M., Arvidsson, S., Kang, D., Larsson, H., Lindstrom, E., & Martinez, V. $CB_1$ receptors mediate the analgesic effects of cannabinoids on colorectal distension-induced visceral pain in rodents. *J. Neurosci.* 29, 1554-1564 (2009).
30. Martin, W. J., Loo, C. M., & Basbaum, A. I. Spinal cannabinoids are anti-allodynic in rats with persistent inflammation. *Pain* 82, 199-205 (1999).
31. Richardson, J. D., Kilo, S., & Hargreaves, K. M. Cannabinoids reduce hyperalgesia and inflammation via interaction with peripheral CB1 receptors. *Pain* 75, 111-119 (1998).
32. Richardson, J. D., Aanonsen, L., & Hargreaves, K. M. Antihyperalgesic effects of spinal cannabinoids. *Eur. J Pharmacol* 345, 145-153 (1998).
33. Herzberg, U., Eliav, E., Bennett, G. J., & Kopin, I. J. The analgesic effects of R(+)-WIN 55,212-2 mesylate, a high affinity cannabinoid agonist, in a rat model of neuropathic pain. *Neurosci. Lett.* 221, 157-160 (1997).
34. Berman, J. S., Symonds, C., & Birch, R. Efficacy of two *cannabis* based medicinal extracts for relief of central neuropathic pain from brachial plexus avulsion: results of a randomised controlled trial. *Pain* 112, 299-306 (2004).
35. Karst, M., Salim, K., Burstein, S., Conrad, I., Hoy, L., & Schneider, U. Analgesic effect of the synthetic cannabinoid CT-3 on chronic neuropathic pain: a randomized controlled trial. *JAMA* 290, 1757-1762 (2003).
36. Notcutt, W., Price, M., Miller, R., Newport, S., Phillips, C., Simmons, S., & Sansom, C. Initial experiences with medicinal extracts of *cannabis* for chronic pain: results from 34 'N of 1' studies. *Anaesthesia* 59, 440-452 (2004).
37. Wilsey, B., Marcotte, T., Tsodikov, A., Millman, J., Bentley, H., Gouaux, B., & Fishman, S. A randomized, placebo-controlled, crossover trial of *cannabis* cigarettes in neuropathic pain. *J. Pain.* 9, 506-521 (2008).
38. Nurmikko, T. J., Serpell, M. G., Hoggart, B., Toomey, P. J., Morlion, B. J., & Haines, D. Sativex successfully treats neuropathic pain characterised by allodynia: a randomised, double-blind, placebo-controlled clinical trial. *Pain.* 133, 210-220 (2007).
39. Abrams, D. I., Jay, C. A., Shade, S. B., Vizoso, H., Reda, H., Press, S., Kelly, M. E., Rowbotham, M. C., & Petersen, K. L. *Cannabis* in painful HIV-associated sensory neuropathy: a randomized placebo-controlled trial. *Neurology.* 68, 515-521 (2007).

40. Bridges, D., Ahmad, K., & Rice, A. S. The synthetic cannabinoid WIN55,212-2 attenuates hyperalgesia and allodynia in a rat model of neuropathic pain. *Br. J. Pharmacol.* 133, 586-594 (2001).
41. Costa, B., Colleoni, M., Conti, S., Trovato, A. E., Bianchi, M., Sotgiu, M. L., & Giagnoni, G. Repeated treatment with the synthetic cannabinoid WIN 55,212-2 reduces both hyperalgesia and production of pronociceptive mediators in a rat model of neuropathic pain. *Br. J. Pharmacol.* 141, 4-8 (2004).
42. Mao, J., Price, D. D., & Mayer, D. J. Experimental mononeuropathy reduces the antinociceptive effects of morphine: implications for common intracellular mechanisms involved in morphine tolerance and neuropathic pain. *Pain* 61, 353-364 (1995).
43. Ossipov, M. H., Lopez, Y., Nichols, M. L., Bian, D., & Porreca, F. The loss of antinociceptive efficacy of spinal morphine in rats with nerve ligation injury is prevented by reducing spinal afferent drive. *Neurosci. Lett.* 199, 87-90 (1995).
44. Rashid, M. H., Inoue, M., Toda, K., & Ueda, H. Loss of peripheral morphine analgesia contributes to the reduced effectiveness of systemic morphine in neuropathic pain. *J. Pharmacol. Exp. Ther.* 309, 380-387 (2004).
45. Lichtman, A. H. & Martin, B. R. The selective cannabinoid antagonist SR 141716A blocks cannabinoid-induced antinociception in rats. *Pharmacol Biochem. Behav.* 57, 7-12 (1997).
46. Rinaldi-Carmona, M., Barth, F., Heaulme, M., Shire, D., Calandra, B., Congy, C., Martinez, S., Maruani, J., Neliat, G., & Caput, D. SR141716A, a potent and selective antagonist of the brain cannabinoid receptor. *FEBS Lett.* 350, 240-244 (1994).
47. Hampson, R. E. & Deadwyler, S. A. Cannabinoids, hippocampal function and memory. *Life Sci.* 65, 715-723 (1999).
48. Pertwee, R. G. The central neuropharmacology of psychotropic cannabinoids. *Pharmacol. Ther.* 36, 189-261 (1988).
49. Dewey, W. L. Cannabinoid pharmacology. *Pharmacol. Rev.* 38, 151-178 (1986).
50. Maccarrone, M. & Wenger, T. Effects of cannabinoids on hypothalamic and reproductive function. *Handb. Exp. Pharmacol.* 555-571 (2005).
51. Basavarajappa, B. S. & Hungund, B. L. Role of the endocannabinoid system in the development of tolerance to alcohol. *Alcohol Alcohol.* 40, 15-24 (2005).
52. Di Marzo, V. & Petrocellis, L. D. Plant, synthetic, and endogenous cannabinoids in medicine. *Annu. Rev. Med.* 57, 553-574 (2006).
53. Mechoulam, R., Spatz, M., & Shohami, E. Endocannabinoids and neuroprotection. *Sci. STKE.* 2002, RE5 (2002).
54. Robson, P. Therapeutic aspects of *cannabis* and cannabinoids. *Br. J. Psychiatry* 178, 107-115 (2001).
55. Ibrahim, M. M., Deng, H., Zvonok, A., Cockayne, D. A., Kwan, J., Mata, H. P., Vanderah, T. W., Lai, J., Porreca, F., Makriyannis, A., & Malan, T. P., Jr. Activation of $CB_2$ cannabinoid receptors by AM1241 inhibits experimental neuropathic pain: pain inhibition by receptors not present in the CNS. *Proc. Natl. Acad. Sci. U.S.A.* 100, 10529-10533 (2003).
56. Walker, J. M., Huang, S. M., Strangman, N. M., Tsou, K., & Sanudo-Pena, M. C. Pain modulation by release of the endogenous cannabinoid anandamide. *Proc. Natl. Acad. Sci. U.S.A.* 96, 12198-12203 (1999).
57. Pertwee, R. G. The diverse CB1 and CB2 receptor pharmacology of three plant cannabinoids: delta9-tetrahydrocannabinol, cannabidiol and delta9-tetrahydrocannabivarin. *Br. J. Pharmacol.* 153, 199-215 (2008).
58. Ballantyne, J. C. Opioid analgesia: perspectives on right use and utility. *Pain Physician* 10, 479-491 (2007).
59. Ballantyne, J. C. & LaForge, K. S. Opioid dependence and addiction during opioid treatment of chronic pain. *Pain.* 129, 235-255 (2007).
60. Horvath, R. J., Romero-Sandoval, E. A., De Leo, J. A., Horvath, B., Mukhopadhyay, P., Hasko, G., & Pacher, P. Glial Modulation in Pain States: Translation into Humans The endocannabinoid system and plant-derived cannabinoids in diabetes and diabetic complications. *Am. J. Pathol.* 180, 432-442 (2012).
61. Szolcsanyi, J. Anandamide and the question of its functional role for activation of capsaicin receptors. *Trends Pharmacol. Sci.* 21, 203-204 (2000).
62. Di Marzo, V., Bisogno, T., & De Petrocellis, L. Anandamide: some like it hot. *Trends Pharmacol. Sci.* 22, 346-349 (2001).
63. Amaya, F., Shimosato, G., Kawasaki, Y., Hashimoto, S., Tanaka, Y., Ji, R. R., & Tanaka, M. Induction of CB1 cannabinoid receptor by inflammation in primary afferent neurons facilitates antihyperalgesic effect of peripheral CB1 agonist. *Pain* 124, 175-183 (2006).
64. Gutierrez, T., Farthing, J. N., Zvonok, A. M., Makriyannis, A., & Hohmann, A. G. Activation of peripheral cannabinoid CB1 and CB2 receptors suppresses the maintenance of inflammatory nociception: a comparative analysis. *Br. J. Pharmacol.* 150, 153-163 (2007).
65. Potenzieri, C., Brink, T. S., Pacharinsak, C., & Simone, D. A. Cannabinoid modulation of cutaneous Adelta nociceptors during inflammation. *J. Neurophysiol.* 100, 2794-2806 (2008).
66. Johanek, L. M. & Simone, D. A. Activation of peripheral cannabinoid receptors attenuates cutaneous hyperalgesia produced by a heat injury. *Pain* 109, 432-442 (2004).
67. Fox, A., Kesingland, A., Gentry, C., McNair, K., Patel, S., Urban, L., & James, I. The role of central and peripheral Cannabinoid$_1$ receptors in the antihyperalgesic activity of cannabinoids in a model of neuropathic pain. *Pain* 92, 91-100 (2001).
68. Potenzieri, C., Harding-Rose, C., & Simone, D. A. The cannabinoid receptor agonist, WIN 55, 212-2, attenuates tumor-evoked hyperalgesia through peripheral mechanisms. *Brain Res.* 1215, 69-75 (2008).
69. Guerrero, A. V., Quang, P., Dekker, N., Jordan, R. C., & Schmidt, B. L. Peripheral cannabinoids attenuate carcinoma-induced nociception in mice. *Neurosci. Lett.* 433, 77-81 (2008).
70. Agarwal, N., Pacher, P., Tegeder, I., Amaya, F., Constantin, C. E., Brenner, G. J., Rubino, T., Michalski, C. W., Marsicano, G., Monory, K., Mackie, K., Marian, C., Batkai, S., Parolaro, D., Fischer, M. J., Reeh, P., Kunos, G., Kress, M., Lutz, B., Woolf, C. J., & Kuner, R. Cannabinoids mediate analgesia largely via peripheral type 1 cannabinoid receptors in nociceptors. *Nat. Neurosci.* 10, 870-879 (2007).
71. Burke, A, Smyth, E. M., & FitzGerald, G. A. Analgesic-antipyretic agents; pharmacotherapy of gout in *Goodman & Gilman's The Pharmacological Basis of Therapeutics* (eds. Brunton, L. L., Lazo, J. S. & Parker, L. K.) 671-715 (McGraw-Hill, New York, 2006).
72. Wickerts, L., Warren, S. M., Brattwall, M., & Jakobsson, J. Coxibs: is there a benefit when compared to traditional non-selective NSAIDs in postoperative pain management? Minerva Anestesiol. 77, 1084-1098 (2011).
73. Mathew, S. T., Devi, S. G., Prasanth, V. V., & Vinod, B. Efficacy and Safety of COX-2 Inhibitors in the Clinical Management of Arthritis: Mini Review. ISRN. Pharmacol. 2011, 480291 (2011).
74. McCormack, P. L. Celecoxib: a review of its use for symptomatic relief in the treatment of osteoarthritis, rheumatoid arthritis and ankylosing spondylitis. Drugs. 71, 2457-2489 (2011).
75. Garcia Rodriguez, L. A., Gonzalez-Perez, A., Bueno, H., & Hwa, J. NSAID use selectively increases the risk of non-fatal myocardial infarction: a systematic review of randomised trials and observational studies. PLoS. ONE. 6, e16780 (2011).
76. Morlion, B. Pharmacotherapy of low back pain: targeting nociceptive and neuropathic pain components. Curr. Med. Res. Opin. 27, 11-33 (2011).
77. Vo, T., Rice, A. S., & Dworkin, R. H. Non-steroidal anti-inflammatory drugs for neuropathic pain: how do we explain continued widespread use? Pain 143, 169-171 (2009).
78. Dworkin, R. H., O'Connor, A. B., Backonja, M., Farrar, J. T., Finnerup, N. B., Jensen, T. S., Kalso, E. A., Loeser, J. D., Miaskowski, C., Nurmikko, T. J., Portenoy, R. K., Rice, A. S., Stacey, B. R., Treede, R. D., Turk, D. C., & Wallace, M. S. Pharmacologic management of neuropathic pain: evidence-based recommendations. Pain 132, 237-251 (2007).
79. Ballantyne, J. C. Opioid analgesia: perspectives on right use and utility. Pain Physician 10, 479-491 (2007).
80. Ballantyne, J. C. & LaForge, K. S. Opioid dependence and addiction during opioid treatment of chronic pain. Pain. 129, 235-255 (2007).
81. Ramasubbu, C. & Gupta, A. Pharmacological treatment of opioid-induced hyperalgesia: a review of the evidence. J. Pain Palliat. Care Pharmacother. 25, 219-230 (2011).
82. Johnston, M. M. & Rapoport, A. M. Triptans for the management of migraine. Drugs 70, 1505-1518 (2010).
83. Saarto, T. & Wiffen, P. J. Antidepressants for neuropathic pain. Cochrane Database Syst. Rev. CD005454 (2007).
84. Baldessarini, R J Drug therapy of depression and anxiety disorders in Goodman & Gilman's The Pharmacological Basis of Therapeutics (eds. Brunton, L. L., Lazo, J. S. & Parker, L. K.) 429-459 (McGraw-Hill, New York, 2006).
85. Finnerup, N. B., Sindrup, S. H., & Jensen, T. S. The evidence for pharmacological treatment of neuropathic pain. Pain 150, 573-581 (2010).
86. Siler, A. C., Gardner, H., Yanit, K., Cushman, T., & McDonagh, M. Systematic review of the comparative effectiveness of antiepileptic drugs for fibromyalgia. J. Pain. 12, 407-415 (2011).
87. Smith, H. S. & Argoff, C. E. Pharmacological treatment of diabetic neuropathic pain. Drugs 71, 557-589 (2011).
88. Waszkielewicz, A. M., Gunia, A., Sloczynska, K., & Marona, H. Evaluation of anticonvulsants for possible use in neuropathic pain. Curr. Med. Chem. 18, 4344-4358 (2011).
89. Berman, J. S., Symonds, C., & Birch, R. Efficacy of two *cannabis* based medicinal extracts for relief of central neuropathic pain from brachial plexus avulsion: results of a randomised controlled trial. Pain 112, 299-306 (2004).
90. Karst, M., Salim, K., Burstein, S., Conrad, I., Hoy, L., & Schneider, U. Analgesic effect of the synthetic cannabinoid CT-3 on chronic neuropathic pain: a randomized controlled trial. JAMA 290, 1757-1762 (2003).
91. Notcutt, W., Price, M., Miller, R., Newport, S., Phillips, C., Simmons, S., & Sansom, C. Initial experiences with medicinal extracts of *cannabis* for chronic pain: results from 34 'N of 1' studies. Anaesthesia 59, 440-452 (2004).
92. Wilsey, B., Marcotte, T., Tsodikov, A., Millman, J., Bentley, H., Gouaux, B., & Fishman, S. A randomized, placebo-controlled, crossover trial of *cannabis* cigarettes in neuropathic pain. J. Pain. 9, 506-521 (2008).
93. Nurmikko, T. J., Serpell, M. G., Hoggart, B., Toomey, P. J., Morlion, B. J., & Haines, D. Sativex successfully treats neuropathic pain characterised by allodynia: a randomised, double-blind, placebo-controlled clinical trial. Pain. 133, 210-220 (2007).
94. Abrams, D. I., Jay, C. A., Shade, S. B., Vizoso, H., Reda, H., Press, S., Kelly, M. E., Rowbotham, M. C., & Petersen, K. L. *Cannabis* in painful HIV-associated sensory neuropathy: a randomized placebo-controlled trial. Neurology. 68, 515-521 (2007).
95. Ellis, R. J., Toperoff, W., Vaida, F., van den, B. G., Gonzales, J., Gouaux, B., Bentley, H., & Atkinson, J. H. Smoked medicinal *cannabis* for neuropathic pain in HIV: a randomized, crossover clinical trial. Neuropsychopharmacology 34, 672-680 (2009).
96. Beltramo, M., Bernardini, N., Bertorelli, R., Campanella, M., Nicolussi, E., Fredduzzi, S., & Reggiani, A. CB2 receptor-mediated antihyperalgesia: possible direct involvement of neural mechanisms. Eur. J. Neurosci. 23, 1530-1538 (2006).
97. Wotherspoon, G., Fox, A., McIntyre, P., Colley, S., Bevan, S., & Winter, J. Peripheral nerve injury induces cannabinoid receptor 2 protein expression in rat sensory neurons. Neuroscience 135, 235-245 (2005).
98. Guindon, J. & Hohmann, A. G. Cannabinoid CB2 receptors: a therapeutic target for the treatment of inflammatory and neuropathic pain. Br. J. Pharmacol. 153, 319-334 (2008).
99. Pacher, P., Mukhopadhyay, P., Mohanraj, R., Godlewski, G., Batkai, S., & Kunos, G. Modulation of the endocannabinoid system in cardiovascular disease: therapeutic potential and limitations. Hypertension. 52, 601-607 (2008).
100. Huffman, J. W., Bushell, S. M., Miller, J. R., Wiley, J. L., & Martin, B. R. 1-Methoxy-, 1-deoxy-11-hydroxy- and 11-hydroxy-1-methoxy-Delta(8)-tetrahydrocannabinols: new selective ligands for the CB2 receptor. Bioorg. Med. Chem. 10, 4119-4129 (2002).
101. Huffman, J. W. The search for selective ligands for the CB2 receptor. Curr. Pharm. Des 6, 1323-1337 (2000).
102. Ibrahim, M. M., Deng, H., Zvonok, A., Cockayne, D. A., Kwan, J., Mata, H. P., Vanderah, T. W., Lai, J., Porreca, F., Makriyannis, A., & Malan, T. P., Jr. Activation of CB2 cannabinoid receptors by AM1241 inhibits experimental neuropathic pain: pain inhibition by receptors not present in the CNS. Proc. Natl. Acad. Sci. U.S.A 100, 10529-10533 (2003).
103. Zhang, J., Hoffert, C., Vu, H. K., Groblewski, T., Ahmad, S., & O'Donnell, D. Induction of CB2 receptor expression in the rat spinal cord of neuropathic but not inflammatory chronic pain models. Eur. J. Neurosci. 17, 2750-2754 (2003).
104. Benito, C., Tolon, R. M., Pazos, M. R., Nunez, E., Castillo, A. I., & Romero, J. Cannabinoid CB2 receptors in human brain inflammation. Br. J. Pharmacol. 153, 277-285 (2008).
105. Dziadulewicz, E. K., Bevan, S. J., Brain, C. T., Coote, P. R., Culshaw, A. J., Davis, A. J., Edwards, L. J., Fisher, A. J., Fox, A. J., Gentry, C., Groarke, A., Hart, T. W., Huber, W., James, I. F., Kesingland, A., La, V. L., Loong, Y., Lyothier, I., McNair, K., O'Farrell, C., Peacock, M., Portmann, R., Schopfer, U., Yagoob, M., & Zadrobilek, J. Naphthalen-1-yl-(4-pentyloxynaphthalen-1-yl)methanone: a potent, orally bioavailable human CB1/CB2 dual agonist with antihyperalgesic properties and restricted central nervous system penetration. J. Med. Chem. 50, 3851-3856 (2007).

106. Brusberg, M., Arvidsson, S., Kang, D., Larsson, H., Lindstrom, E., & Martinez, V. CB1 receptors mediate the analgesic effects of cannabinoids on colorectal distension-induced visceral pain in rodents. J. Neurosci. 29, 1554-1564 (2009).

107. Fride, E., Feigin, C., Ponde, D. E., Breuer, A., Hanus, L., Arshaysky, N., & Mechoulam, R. (+)-Cannabidiol analogues which bind cannabinoid receptors but exert peripheral activity only. Eur. J. Pharmacol. 506, 179-188 (2004).

108. Pertwee, R. G., Thomas, A., Stevenson, L. A., Maor, Y., & Mechoulam, R. Evidence that (−)-7-hydroxy-4'-dimethylheptyl-cannabidiol activates a non-CB(1), non-CB(2), non-TRPV1 target in the mouse vas deferens. Neuropharmacology. 48, 1139-1146 (2005).

109. Ben-Shabat, S., Hanus, L. O., Katzavian, G., & Gallily, R. New cannabidiol derivatives: synthesis, binding to cannabinoid receptor, and evaluation of their antiinflammatory activity. J. Med. Chem. 49, 1113-1117 (2006).

110. Adam, J. M., Clark, J. K., Davies, K., Everett, K., Fields, R., Francis, S., Jeremiah, F., Kiyoi, T., Maidment, M., Morrison, A., Ratcliffe, P., Prosser, A., Schulz, J., Wishart, G., Baker, J., Boyce, S., Campbell, R., Cottney, J. E., Deehan, M., & Martin, I. Low brain penetrant CB1 receptor agonists for the treatment of neuropathic pain. Bioorg. Med. Chem. Lett. 22, 2932-2937 (2012).

111. Yu, X. H., Cao, C. Q., Martino, G., Puma, C., Morinville, A., St-Onge, S., Lessard, E., Perkins, M. N., & Laird, J. M. A peripherally restricted cannabinoid receptor agonist produces robust anti-nociceptive effects in rodent models of inflammatory and neuropathic pain. Pain 151, 337-344 (2010).

112. Fulp, A., Bortoff, K., Zhang, Y., Seltzman, H., Snyder, R., & Maitra, R. Towards rational design of cannabinoid receptor 1 (CB1) antagonists for peripheral selectivity. Bioorg. Med. Chem. Lett. 21, 5711-5714 (2011).

113. Fulp, A., Bortoff, K., Seltzman, H., Zhang, Y., Mathews, J., Snyder, R., Fennell, T., & Maitra, R. Design and synthesis of cannabinoid receptor 1 antagonists for peripheral selectivity. J. Med. Chem. 55, 2820-2834 (2012).

114. Wang, Q., Rager, J. D., Weinstein, K., Kardos, P. S., Dobson, G. L., Li, J., & Hidalgo, I. J. Evaluation of the MDR-MDCK cell line as a permeability screen for the blood-brain barrier. Int. J. Pharm. 288, 349-359 (2005).

115. Huffman, J. W., Mabon, R., Wu, M. J., Lu, J., Hart, R., Hurst, D. P., Reggio, P. H., Wiley, J. L., & Martin, B. R. 3-Indolyl-1-naphthylmethanes: new cannabimimetic indoles provide evidence for aromatic stacking interactions with the CB1 cannabinoid receptor. Bioorg. Med. Chem. 11, 539-549 (2003).

116. McAllister, S. D., Rizvi, G., navi-Goffer, S., Hurst, D. P., Barnett-Norris, J., Lynch, D. L., Reggio, P. H., & Abood, M. E. An aromatic microdomain at the cannabinoid CB1 receptor constitutes an agonist/inverse agonist binding region. J. Med. Chem. 46, 5139-5152 (2003).

117. Reggio, P. H., Basu-Dutt, S., Barnett-Norris, J., Castro, M. T., Hurst, D. P., Seltzman, H. H., Roche, M. J., Gilliam, A. F., Thomas, B. F., Stevenson, L. A., Pertwee, R. G., & Abood, M. E. The bioactive conformation of aminoalkylindoles at the cannabinoid CB1 and CB2 receptors: insights gained from (E)- and (Z)-naphthylidene indenes. J. Med. Chem. 41, 5177-5187 (1998).

118. Carroll, F. I., Lewin, A. H., Mascarella, S. W., Seltzman, H. H., & Reddy, P. A. Designer drugs: a medicinal chemistry perspective. Ann. N. Y. Acad. Sci. 1248, 18-38 (2012).

119. Kumar, V., Alexander, M. D., Bell, M. R., Eissenstat, M. A., Casiano, F. M., Chippari, S. M., Haycock, D. A., Luttinger, D. A., Kuster, J. E., Miller, M. S., Stevenson, J. I., & Ward, S. J. Morpholinoalkylindenes as antinociceptive agents: Novel cannabinoid receptor agonists. Bioorganic & Medicinal Chemistry Letters 5, 381-386 (1995).

120. Eissenstat, M. A., Bell, M. R., D'Ambra, T. E., Alexander, E. J., Daum, S. J., Ackerman, J. H., Gruett, M. D., Kumar, V., Estep, K. G., Olefirowicz, E. M., & Aminoalkylindoles: structure-activity relationships of novel cannabinoid mimetics. J. Med. Chem. 38, 3094-3105 (1995).

121. Hunter, C. A., Lawson, K. R., Perkins, J., & Urch, C. J. Aromatic interactions. J. Chem. Soc. Perkin Trans. 2, 651-669 (2001).

122. Clark, D. E. Rapid calculation of polar molecular surface area and its application to the prediction of transport phenomena. 2. Prediction of blood-brain barrier penetration. J. Pharm. Sci. 88, 815-821 (1999).

123. Clark, D. E. & Pickett, S. D. Computational methods for the prediction of 'drug-likeness'. Drug Discov. Today 5, 49-58 (2000).

124. Clark, D. E. Computational prediction of blood-brain barrier permeation. Ann. Reports Med. Chem. 40, 403-415 (2005).

125. Yu, X. H., Cao, C. Q., Martino, G., Puma, C., Morinville, A., St-Onge, S., Lessard, E., Perkins, M. N., & Laird, J. M. A peripherally restricted cannabinoid receptor agonist produces robust anti-nociceptive effects in rodent models of inflammatory and neuropathic pain. Pain 151, 337-344 (2010).

126. Reggio, P. H. Pharmacophores for ligand recognition and activation/inactivation of the cannabinoid receptors. Curr. Pharm. Des. 9, 1607-1633 (2003).

127. Brents, L. K., Reichard, E. E., Zimmerman, S. M., Moran, J. H., Fantegrossi, W. E., & Prather, P. L. Phase I hydroxylated metabolites of the K2 synthetic cannabinoid JWH-018 retain in vitro and in vivo cannabinoid 1 receptor affinity and activity. PLoS. ONE. 6, e21917 (2011).

128. Brents, L. K., Gallus-Zawada, A., Radominska-Pandya, A., Vasiljevik, T., Prisinzano, T. E., Fantegrossi, W. E., Moran, J. H., & Prather, P. L. Monohydroxylated metabolites of the K2 synthetic cannabinoid JWH-073 retain intermediate to high cannabinoid 1 receptor (CB1R) affinity and exhibit neutral antagonist to partial agonist activity. Biochem. Pharmacol. 83, 952-961 (2012).

129. Ertl, P., Rohde, B., & Selzer, P. Fast calculation of molecular polar surface area as a sum of fragment-based contributions and its application to the prediction of drug transport properties. J. Med. Chem. 43, 3714-3717 (2000).

130. D'Ambra, T. E., Eissenstat, M. A., Abt, J., Ackerman, J. H., Bacon, E. R., Bell, M. R., Carabateas, P. M., Josef, K. A., Kumar, V., Weaver, J. D. I., Arnold, R., Casiano, F. M., Chippari, S. M., Haycock, D. A., Kuster, J. E., Luttinger, D. A., Stevenson, J. I., Ward, S. J., Hill, W. A., Khanolkar, A., & Makriyannis, A. C-Attached aminoalky- 130. (continued) lindoles: potent cannabinoid mimetics. Bioorg. Med. Chem. Lett. 6, 17-22 (1996).

131. Mosconi, T. & Kruger, L. Fixed-diameter polyethylene cuffs applied to the rat sciatic nerve induce a painful neuropathy: Ultrastructural morphometric analysis of axonal alterations. Pain 64, 37-57 (1996).

132. Bennett, G. J. & Xie, Y. K. A peripheral mononeuropathy in rat that produces disorders of pain sensation like those seen in man. Pain 33, 87-107 (1988).

133. Pitcher, G. M., Ritchie, J., & Henry, J. L. Nerve constriction in the rat: model of neuropathic, surgical and central pain. Pain 83, 37-46 (1999).

134. Bailey, A. L. & Ribeiro-da-Silva, A. Transient loss of terminals from non-peptidergic nociceptive fibers in the substantia gelatinosa of spinal cord following chronic constriction injury of the sciatic nerve. Neuroscience 138, 675-690 (2006).

135. Thakor, D. K., Lin, A., Matsuka, Y., Meyer, E. M., Ruangsri, S., Nishimura, I., & Spigelman, I. Increased peripheral nerve excitability and local NaV1.8 mRNA up-regulation in painful neuropathy. Mol. Pain 5:14., 14 (2009).

136. Ruangsri, S., Lin, A., Mulpuri, Y., Lee, K., Spigelman, 1., & Nishimura, I. Relationship of axonal voltage-gated sodium channel 1.8 (NaV1.8) mRNA accumulation to sciatic nerve injury-induced painful neuropathy in rats. J. Biol. Chem. 286, 39836-39847 (2011).

137. Pertwee, R. G. The central neuropharmacology of psychotropic cannabinoids. Pharmacol. Ther. 36, 189-261 (1988).

138. Dewey, W. L. Cannabinoid pharmacology. Pharmacol. Rev. 38, 151-178 (1986).

139. Martin, B. R., Compton, D. R., Thomas, B. F., Prescott, W. R., Little, P. J., Razdan, R. K., Johnson, M. R., Melvin, L. S., Mechoulam, R., & Ward, S. J. Behavioral, biochemical, and molecular modeling evaluations of cannabinoid analogs. Pharmacol. Biochem. Behav. 40, 471-478 (1991).

140. Smith, P. B., Compton, D. R., Welch, S. P., Razdan, R. K., Mechoulam, R., & Martin, B. R. The pharmacological activity of anandamide, a putative endogenous cannabinoid, in mice. J. Pharmacol. Exp. Ther. 270, 219-227 (1994).

141. Compton, D. R., Rice, K. C., de Costa, B. R., Razdan, R. K., Melvin, L. S., Johnson, M. R., & Martin, B. R. Cannabinoid structure-activity relationships: correlation of receptor binding and in vivo activities. J. Pharmacol. Exp. Ther. 265, 218-226 (1993).

142. Calignano, A., La Rana, G., Giuffrida, A., & Piomelli, D. Control of pain initiation by endogenous cannabinoids. Nature 394, 277-281 (1998).

143. Malan, T. P., Jr., Ibrahim, M. M., Deng, H., Liu, Q., Mata, H. P., Vanderah, T., Porreca, F., & Makriyannis, A. CB2 cannabinoid receptor-mediated peripheral antinociception. Pain 93, 239-245 (2001).

144. Richardson, J. D., Kilo, S., & Hargreaves, K. M. Cannabinoids reduce hyperalgesia and inflammation via interaction with peripheral CB1 receptors. Pain 75, 111-119 (1998).

145. Maccarrone, M. & Wenger, T. Effects of cannabinoids on hypothalamic and reproductive function. Handb. Exp. Pharmacol. 555-571 (2005).

146. Pertwee, R G Effects of Cannabinoids on Thermoregulation: A Brief Review in Marihuana '84 (ed. Harvey, D. J.) 263-277 (IRL Press, Oxford, 1985).

147. Rawls, S. M., Tallarida, R. J., Kon, D. A., Geller, E. B., & Adler, M. W. GABAA receptors modulate cannabinoid-evoked hypothermia. Pharmacol. Biochem. Behav. 78, 83-91 (2004).

148. Freiman, I. & Szabo, B. Cannabinoids depress excitatory neurotransmission between the subthalamic nucleus and the globus pallidus. Neuroscience 133, 305-313 (2005).

149. Sanudo-Pena, M. C., Romero, J., Seale, G. E., Fernandez-Ruiz, J. J., & Walker, J. M. Activational role of cannabinoids on movement. Eur. J. Pharmacol. 391, 269-274 (2000).

150. Rodriguez, d. F., del Arco, I., Martin-Calderon, J. L., Gorriti, M. A., & Navarro, M. Role of the endogenous cannabinoid system in the regulation of motor activity. Neurobiol. Dis. 5, 483-501 (1998).

151. DUNHAM, N. W. & MIYA, T. S. A note on a simple apparatus for detecting neurological deficit in rats and mice. J. Am. Pharm. Assoc. (Baltim.) 46, 208-209 (1957).

152. Pryor, G. T., Husain, S., Larsen, F., McKenzie, C. E., Carr, J. D., & Braude, M. C. Interactions between D9-tetrahydrocannabinol and phencyclidine hydrochloride in rats. Pharmacol Biochem. Behav. 6, 123-136 (1977).

153. Fox, A., Kesingland, A., Gentry, C., McNair, K., Patel, S., Urban, L., & James, I. The role of central and peripheral Cannabinoid1 receptors in the antihyperalgesic activity of cannabinoids in a model of neuropathic pain. Pain 92, 91-100 (2001).

154. Pertwee, R. G. The ring test: a quantitative method for assessing the 'cataleptic' effect of *cannabis* in mice. Br. J. Pharmacol. 46, 753-763 (1972).

155. Amaya, F., Shimosato, G., Kawasaki, Y., Hashimoto, S., Tanaka, Y., Ji, R. R., & Tanaka, M. Induction of CB1 cannabinoid receptor by inflammation in primary afferent neurons facilitates antihyperalgesic effect of peripheral CB1 agonist. Pain 124, 175-183 (2006).

156. Buggy, D. J., Toogood, L., Maric, S., Sharpe, P., Lambert, D. G., & Rowbotham, D. J. Lack of analgesic efficacy of oral delta-9-tetrahydrocannabinol in postoperative pain. Pain. 106, 169-172 (2003).

157. Beaulieu, P. Effects of nabilone, a synthetic cannabinoid, on postoperative pain. Can. J. Anaesth. 53, 769-775 (2006).

158. Izzo, A. A., Mascolo, N., & Capasso, F. The gastrointestinal pharmacology of cannabinoids. Curr. Opin. Pharmacol. 1, 597-603 (2001).

159. Gong, H., Jr., Tashkin, D. P., Simmons, M. S., Calvarese, B., & Shapiro, B. J. Acute and subacute bronchial effects of oral cannabinoids. Clin. Pharmacol. Ther. 35, 26-32 (1984).

160. Laviolette, M. & Belanger, J. Role of prostaglandins in marihuana-induced bronchodilation. Respiration. 49, 10-15 (1986).

161. Potenzieri, C., Harding-Rose, C., & Simone, D. A. The cannabinoid receptor agonist, WIN 55, 212-2, attenuates tumor-evoked hyperalgesia through peripheral mechanisms. Brain Res. 1215, 69-75 (2008).

162. Guerrero, A. V., Quang, P., Dekker, N., Jordan, R. C., & Schmidt, B. L. Peripheral cannabinoids attenuate carcinoma-induced nociception in mice. Neurosci. Lett. 433, 77-81 (2008).

163. National Diabetes Information Clearinghouse. National Institute of Diabetes & Digestive & Kidney Diseases. 2003. Ref Type: Electronic Citation
164. Burgos, E., Gomez-Nicola, D., Pascual, D., Martin, M. I., Nieto-Sampedro, M., & Goicoechea, C. Cannabinoid agonist WIN 55,212-2 prevents the development of paclitaxel-induced peripheral neuropathy in rats. Possible involvement of spinal glial cells. Eur. J. Pharmacol. 682, 62-72 (2012).
165. Pascual, D., Goicoechea, C., Suardiaz, M., & Martin, M. I. A cannabinoid agonist, WIN 55,212-2, reduces neuropathic nociception induced by paclitaxel in rats. Pain 118, 23-34 (2005).
166. Rahn, E. J., Makriyannis, A., & Hohmann, A. G. Activation of cannabinoid CB1 and CB2 receptors suppresses neuropathic nociception evoked by the chemotherapeutic agent vincristine in rats. Br. J. Pharmacol. (2007).
167. Rahn, E. J., Zvonok, A. M., Thakur, G. A., Khanolkar, A. D., Makriyannis, A., & Hohmann, A. G. Selective activation of cannabinoid CB2 receptors suppresses neuropathic nociception induced by treatment with the chemotherapeutic agent paclitaxel in rats. J. Pharmacol. Exp. Ther. 327, 584-591 (2008).
168. Xu, J. J., Diaz, P., struc-Diaz, F., Craig, S., Munoz, E., & Naguib, M. Pharmacological characterization of a novel cannabinoid ligand, MDA19, for treatment of neuropathic pain. Anesth. Analg. 111, 99-109 (2010).
169. Porcella, A., Maxia, C., Gessa, G. L., & Pani, L. The synthetic cannabinoid WIN55212-2 decreases the intraocular pressure in human glaucoma resistant to conventional therapies. Eur. J. Neurosci. 13, 409-412 (2001).
170. Machado Rocha, F. C., Stefano, S. C., De Cassia, H. R., Rosa Oliveira, L. M., & Da Silveira, D. X. Therapeutic use of *Cannabis sativa* on chemotherapy-induced nausea and vomiting among cancer patients: systematic review and meta-analysis. Eur. J. Cancer Care (Engl.) 17, 431-443 (2008).
171. Esfandyari, T., Camilleri, M., Busciglio, I., Burton, D., Baxter, K., & Zinsmeister, A. R. Effects of a cannabinoid receptor agonist on colonic motor and sensory functions in humans: a randomized, placebo-controlled study. Am. J. Physiol Gastrointest. Liver Physiol. 293, G137-G145 (2007).
172. Ligresti, A., Moriello, A. S., Starowicz, K., Matias, I., Pisanti, S., De Petrocellis, L., Laezza, C., Portella, G., Bifulco, M., & Di Marzo, V. Antitumor activity of plant cannabinoids with emphasis on the effect of cannabidiol on human breast carcinoma. J. Pharmacol. Exp. Ther. 318, 1375-1387 (2006).
173. Idris, A. I. Role of cannabinoid receptors in bone disorders: Alternatives for treatment. Drug News Perspect. 21, 533-540 (2008).
174. Martin, I. Prediction of blood-brain barrier penetration: are we missing the point? Drug Discov. Today 9, 161-162 (2004).
175. Hargreaves, K., Dubner, R., Brown, F., Flores, C., & kris, J. A new and sensitive method for measuring thermal nociception in cutaneous hyperalgesia. Pain 32, 77-88 (1988).

TABLE 1

| # | Structure | IUPAC Name | CB1_KI_CP | CB2_KI_CP | MDCK_BA | Ca_Flux | Ca Flux % Emax |
|---|---|---|---|---|---|---|---|
| 1 | 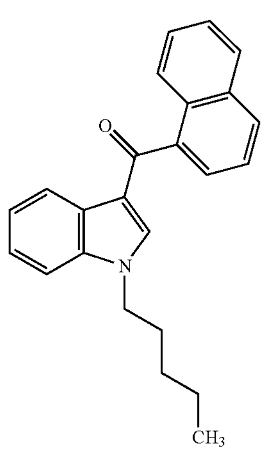 [SMILES: CCCCCn1cc(C(=O)c2cccc3ccccc23)c2ccccc21] | 3-(naphthalene-1-carbonyl)-1-pentyl-1H-indole | 4.31 | 7.38 | | | |

TABLE 1-continued

| # | Structure | IUPAC Name | CB1_KI_CP | CB2_KI_CP | MDCK_BA | Ca_Flux | Ca Flux % Emax |
|---|---|---|---|---|---|---|---|
| 8 | 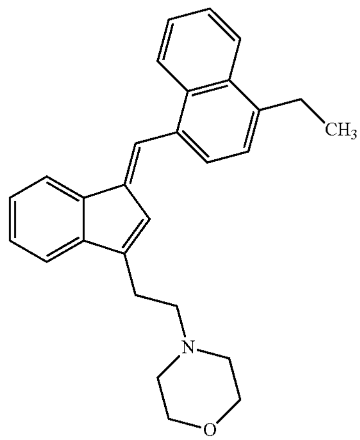 [SMILES: CCc1ccc(/C=C2\C=C(CCN3CCOCC3)c3ccccc32)c2ccccc12] | 4-{2-[(1E)-1-[(4-ethylnaphthalen-1-yl)methylidene]-1H-inden-3-yl]ethyl} morpholine | 0.86 | 0.79 | 0.00 | 141.00 | 121 |
| 9 | 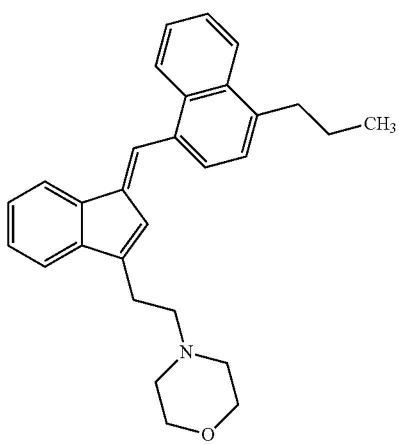 [SMILES: CCCc1ccc(/C=C2\C=C(CCN3CCOCC3)c3ccccc32)c2ccccc12] | 4-{2-[(1E)-1-[(4-propylnaphthalen-1-yl)methylidene]-1H-inden-3-yl]ethyl} morpholine | 1.18 | 1.00 | 0.00 | 182.00 | 108 |
| 10 | 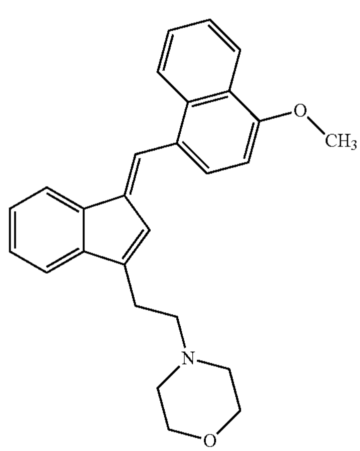 [SMILES: COc1ccc(/C=C2\C=C(CCN3CCOCC3)c3ccccc32)c2ccccc12] | 4-{2-[(1E)-2-[(4-methoxy-naphthalen-1-yl)methylidene]-1H-inden-3-yl]ethyl} morpholine | 2.43 | 4.17 | 0.00 | 196.00 | 114 |

TABLE 1-continued

| # | Structure | IUPAC Name | CB1_KI_CP | CB2_KI_CP | MDCK_BA | Ca_Flux | Ca Flux % Emax |
|---|---|---|---|---|---|---|---|
| 11 | 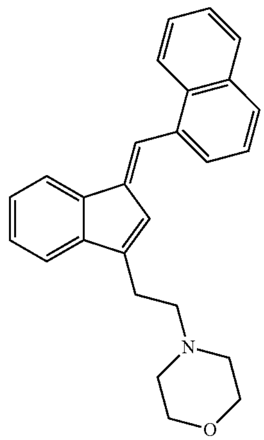 [SMILES: C1=C(CCN2CCOCC2)c2ccccc2/C1=C/c1cccc2ccccc12] | 4-{2-[(1E)-1-(naphthalen-1-ylmethylidene)-1H-inden-3-yl]ethyl} morpholine | 4.69 | 5.62 | 0.00 | 126.80 | 103 |
| 12 | 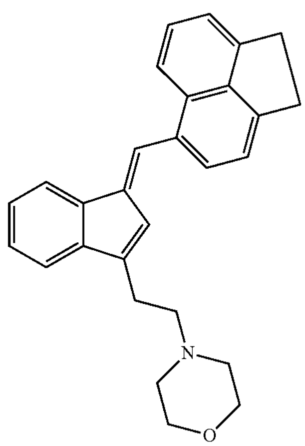 [SMILES: C1=C(CCN2CCOCC2)c2ccccc2/C1=C/c1ccc2c3c(cccc13)CC2] | 4-{2-[(1E)-1-(1,2-dihydroacenaphthylen-5-ylmethylidene)-1H-inden-3-yl]ethyl} morpholine | 15.90 | 4.22 | 0.00 | | |
| 13 | 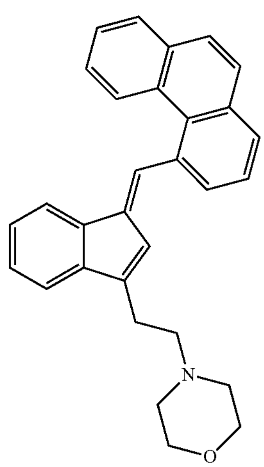 [SMILES: C1=C(CCN2CCOCC2)c2ccccc2/C1=C/c1cccc2ccc3ccccc3c12] | 4-{2-[(1E)-1-(phenanthren-4-ylmethylidene)-1H-inden-3-yl]ethyl} morpholine | 22.90 | 6.00 | 0.00 | | |

TABLE 1-continued

| # | Structure | IUPAC Name | CB1_KI_CP | CB2_KI_CP | MDCK_BA | Ca_Flux | Ca Flux % Emax |
|---|---|---|---|---|---|---|---|
| 14 | 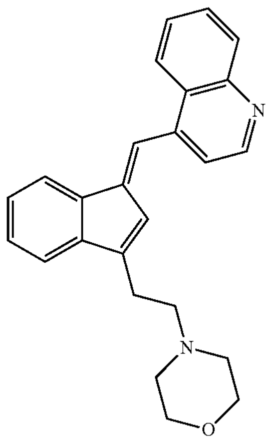 [SMILES: C1=C(CCN2CCOCC2)c2ccccc2/C1=C/c1ccnc2ccccc12] | 4-{[(1E)-3-[2-(morpholin-4-yl)ethyl]-1H-inden-1-ylidene]methyl} quinoline | 23.30 | 12.10 | | | |
| 15 | 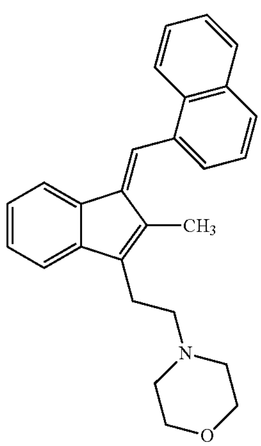 [SMILES: CC1=C(CCN2CCOCC2)c2ccccc2/C1=C/c1cccc2ccccc12] | 4-{2-[(1E)-2-methyl-1-(naphthalen-1-ylmethylidene)-1H-inden-3-yl]ethyl} morpholine | 26.30 | 2.84 | | 557.00 | |
| 16 | 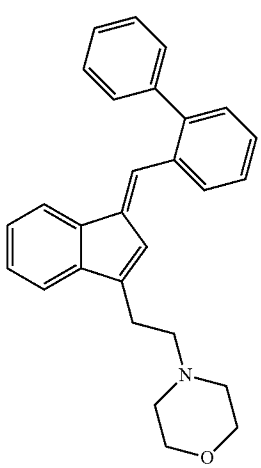 [SMILES: C1=C(CCN2CCOCC2)c2ccccc2/C1=C/c1ccccc1-c1ccccc1] | 4-{2-[(1E)-1-[(2-phenylphenyl)methylidene]-1H-inden-3-yl]ethyl} morpholine | 82.90 | 15.30 | | | |

TABLE 1-continued
| # | Structure | IUPAC Name | CB1_KI_CP | CB2_KI_CP | MDCK_BA | Ca_Flux | Ca Flux % Emax |
|---|---|---|---|---|---|---|---|
| 17 | 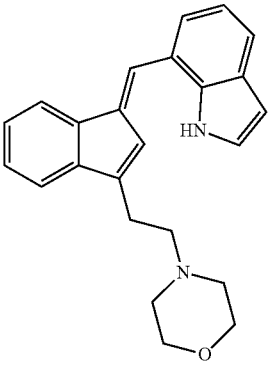 [SMILES: C1=C(CCN2CCOCC2)c2ccccc2/C1=C/c1cccc2cc[nH]c12] | 7-{[(1E)-3-[2-(morpholin-4-yl)ethyl]-1H-inden-1-ylidene]methyl}-1H-indole | 107.00 | 8.70 | | | |
| 18 | 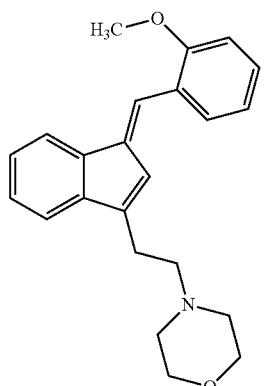 | 4-{2-[(1E)-1-[(2-methoxyphenyl)methylidene]-1H-inden-3-yl]ethyl}morpholine | 149.00 | 29.80 | | | |
| 19 | 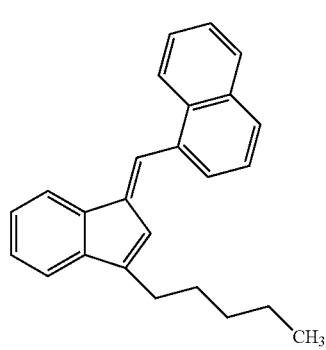 [SMILES: CCCCCC1=C/C(=C\c2cccc3ccccc23)c2ccccc21] | 1-{[(1E)-3-pentyl-1H-inden-1-ylidene]methyl}naphthalene | 17.20 | 163.00 | | | |
| 20 | 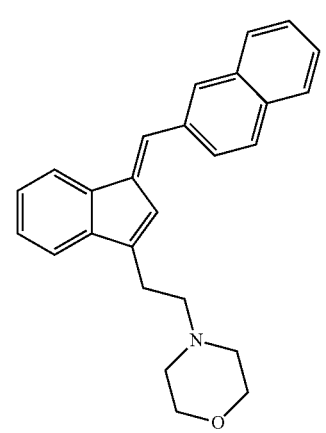 [SMILES: C1=C(CCN2CCOCC2)c2ccccc2/C1=C/c1ccc2ccccc2c1] | 4-{2-[(1E)-1-(naphthalen-2-ylmethylidene)-1H-inden-3-yl]ethyl}morpholine | 134.00 | 24.40 | 0.00 | | |

TABLE 1-continued

| # | Structure | IUPAC Name | CB1_KI_CP | CB2_KI_CP | MDCK_BA | Ca_Flux | Ca Flux % Emax |
|---|---|---|---|---|---|---|---|
| 21 | 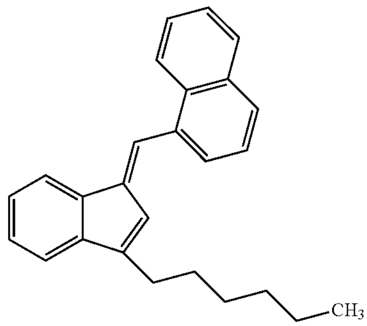 [SMILES: CCCCCCC1=C/C(=C\c2cccc3ccccc23)c2ccccc21] | 1-{[(1E)-3-hexyl-1H-inden-1-ylidene]methyl} naphthalene | | 1454.00 | | | |
| 22 | 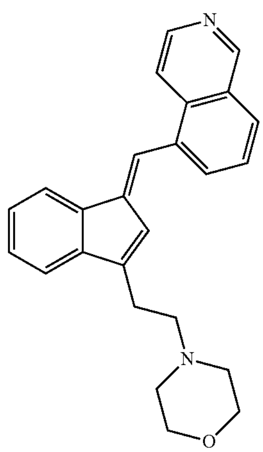 [SMILES: C1=C(CCN2CCOCC2)c2ccccc2/C1=C/c1cccc2cnccc12] | 5-{[(1E)-3-[2-(morpholin-4-yl)ethyl]-1H-inden-1-ylidene]methyl} isoquinoline | 454.00 | 51.40 | | | |
| 23 | 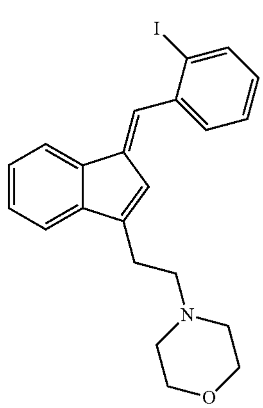 [SMILES: Ic1ccccc1/C=C1\C=C(CCN2CCOCC2)c2ccccc21] | 4-{2-[(1E)-1-[(2-iodophenyl) methyl-idene]-1H-inden-3-yl]ethyl} morpholine | 607.00 | 109.00 | | | |

TABLE 1-continued

| # | Structure | IUPAC Name | CB1_KI_CP | CB2_KI_CP | MDCK_BA | Ca_Flux | Ca Flux % Emax |
|---|---|---|---|---|---|---|---|
| 24 | 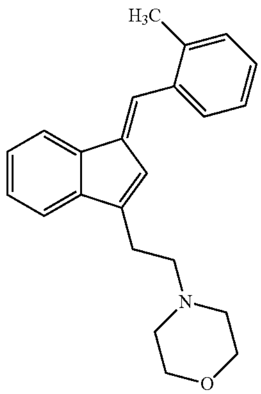 [SMILES: Cc1ccccc1/C=C1\C=C(CCN2CCOCC2)c2ccccc21] | 4-{2-[(1E)-1-[(2-methylphenyl)methylidene]-1H-inden-3-yl]ethyl}morpholine | 623.00 | 95.40 | | | |
| 25 | 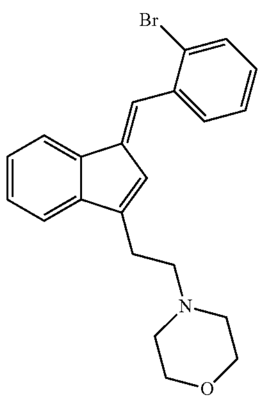 [SMILES: Brc1ccccc1/C=C1\C=C(CCN2CCOCC2)c2ccccc21] | 4-{2-[(1E)-1-[(2-bromophenyl)methylidene]-1H-inden-3-yl]ethyl}morpholine | 647.00 | 206.00 | | | |
| 26 | 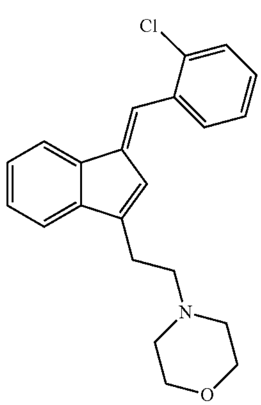 [SMILES: Clc1ccccc1/C=C1\C=C(CCN2CCOCC2)c2ccccc21] | 4-{2-[(1E)-1-[(2-chlorophenyl)methylidene]-1H-inden-3-yl]ethyl}morpholine | 862.00 | | | | |

TABLE 1-continued

| # | Structure | IUPAC Name | CB1_KI_CP | CB2_KI_CP | MDCK_BA | Ca_Flux | Ca Flux % Emax |
|---|---|---|---|---|---|---|---|
| 28 | 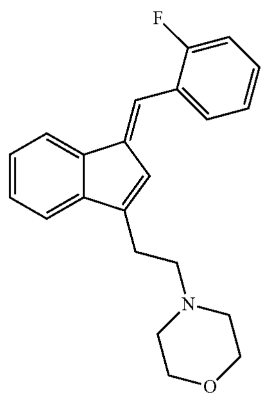 | 4-{2-[(1E)-1-[(2-fluorophenyl)methylidene]-1H-inden-3-yl]ethyl}morpholine | 1000.00 | 429.00 | | | |
| 29 | 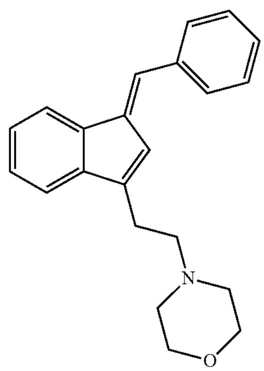 [SMILES: C1=C(CCN2CCOCC2)c2ccccc2/C1=C/c1ccccc1] | 4-{2-[(1E)-1-(phenyl-methylidene)-1H-inden-3-yl]ethyl}morpholine | 1297.00 | 295.00 | | | |
| 30 | 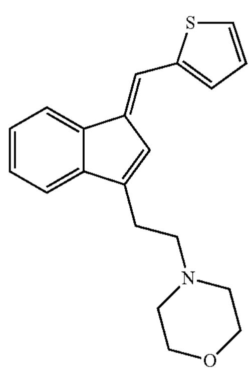 [SMILES: C1=C(CCN2CCOCC2)c2ccccc2/C1=C/c1cccs1] | 4-{2-[(1E)-1-(thiophen-2-ylmethylidene)-1H-indene-3-yl]ethyl}morpholine | 8528.00 | 3018.00 | | | |
| 31 | 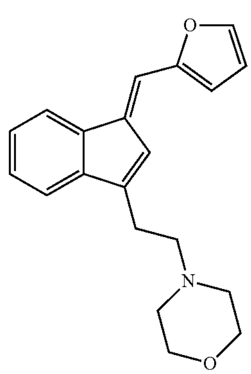 [SMILES: C1=C(CCN2CCOCC2)c2ccccc2/C1=C/c1ccco1] | 4-{2-[(1E)-1-(furan-2-ylmethylidene)-1H-inden-3-yl]ethyl}morpholine | 10000.00 | 1258.00 | | | |

TABLE 1-continued

| # | Structure | IUPAC Name | CB1_KI_CP | CB2_KI_CP | MDCK_BA | Ca_Flux | Ca Flux % Emax |
|---|---|---|---|---|---|---|---|
| 34 | 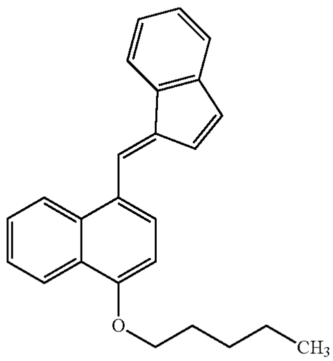 [SMILES: CCCCCOc1ccc(/C=C2\C=Cc3ccccc32)c2ccccc12] | 1-[(1E)-1H-inden-1-ylidenemethyl]-4-(penyloxy)naphthalene | 10000.00 | | | | |
| 35 | 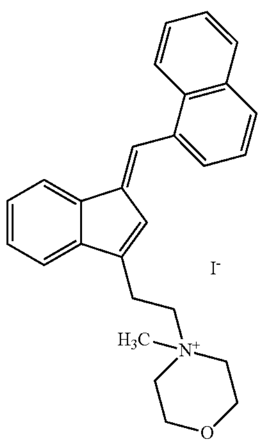 [SMILES: C[N+]1(CCC2=C/C(=C\c3cccc4ccccc34)c3ccccc32)CCOCC1 ; [I-]] | 4-methyl-4-{2-[(1E)-1-(naphthalen-1-ylmethylidene)-1H-inden-3-yl]ethyl}morpholin-4-ium iodide | 982.00 | | | | |
| 36 | 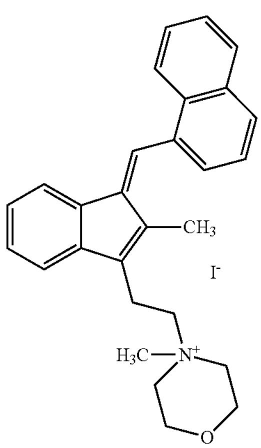 [SMILES: CC1=C(CC[N+]2(C)CCOCC2)c2ccccc2/C1=C/c1cccc2ccccc12 ; [I-]] | 4-methyl-4-{2-[(1E)-2-methyl-1-(naphthalen-1-ylmethylidene)-1H-inden-3-yl]ethyl}morpholin-4-ium iodide | 1614.00 | | | | |

TABLE 1-continued

| # | Structure | IUPAC Name | CB1_KI_CP | CB2_KI_CP | MDCK_BA | Ca_Flux | Ca Flux % Emax |
|---|---|---|---|---|---|---|---|
| 37 | 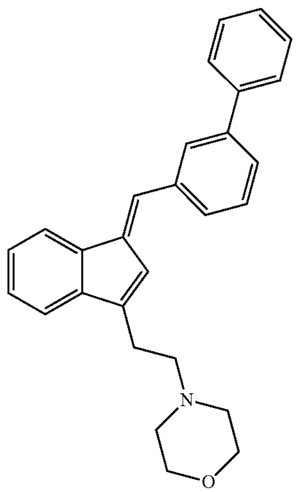 [SMILES: C1=C(CCN2CCOCC2)c2ccccc2/C1=C/c1cccc(-c2ccccc2)c1] | 4-{2-[(1E)-1-[(3-phenylphenyl)methylidene]-1H-inden-3-yl]ethyl}morpholine | 2603.00 | 132.00 | | | |
| 38 | 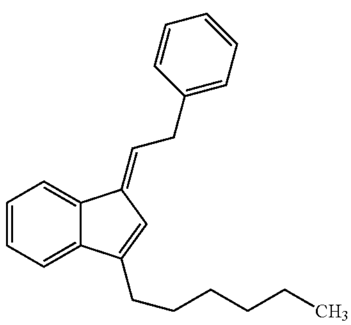 [SMILES: CCCCCCC1=C/C(=C\Cc2ccccc2)c2ccccc21] | (1E)-3-hexyl-1-(2-phenyl-ethylidene)-1H-indene | 4414.00 | 13667.00 | | | |
| 39 | 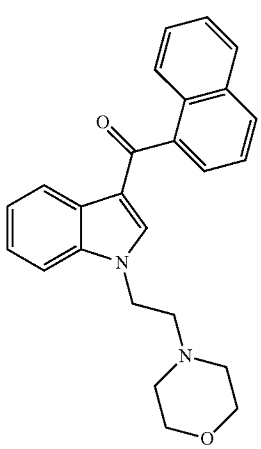 [SMILES: O=C(c1cccc2ccccc12)c1cn(CCN2CCOCC2)c2ccccc12] | 1-[2-(morpholin-4-yl)ethyl]-3-(naphthalene-1-carbonyl)-1H-indole | 81.60 | | | 272.90 | |

TABLE 1-continued

| # | Structure | IUPAC Name | CB1_KI_CP | CB2_KI_CP | MDCK_BA | Ca_Flux | Ca Flux % Emax |
|---|---|---|---|---|---|---|---|
| 40 | 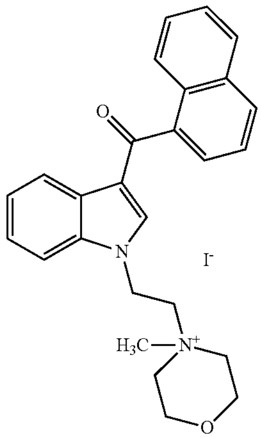 [SMILES: C[N+]1(CCn2cc(C(=O)c3cccc4ccccc34)c3ccccc32)CCOCC1 ; [I-]] | 4-methyl-4-{2-[3-(naphthalene-1-carbonyl)-1H-indol-1-yl]ethyl}morpholin-4-ium iodide | 10000.00 | | | | |
| 41 | 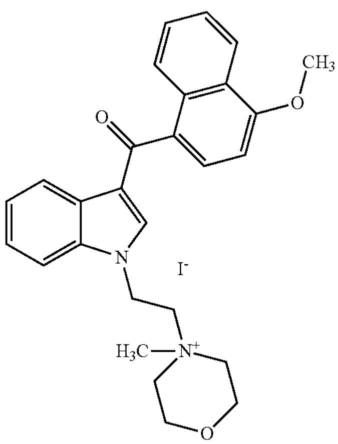 [SMILES: COc1ccc(C(=O)c2cn(CC[N+]3(C)CCOCC3)c3ccccc23)c2ccccc12 ; [I-]] | 4-{2-[3-(4-methoxynaphth-alene-1-carbonyl)-1H-indol-1-yl]ethyl}-4-methylmorpholin-4-ium iodide | 4083.00 | | | | |
| 42 | 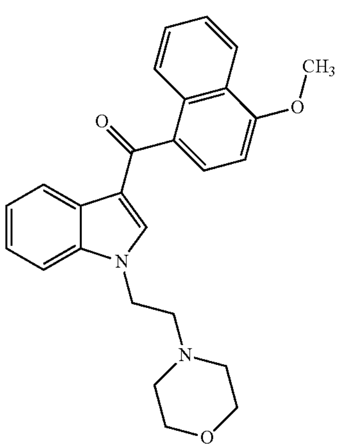 [SMILES: COc1ccc(C(=O)c2cn(CCN3CCOCC3)c3ccccc23)c2ccccc12] | 3-(4-methoxynaphtha-lene-1-carbonyl)-1-[2-(morpholin-4-yl)ethyl]-1H-indole | 88.10 | | | 445.00 | |

TABLE 1-continued

| # | Structure | IUPAC Name | CB1_KI_CP | CB2_KI_CP | MDCK_BA | Ca_Flux | Ca Flux % Emax |
|---|---|---|---|---|---|---|---|
| 43 | 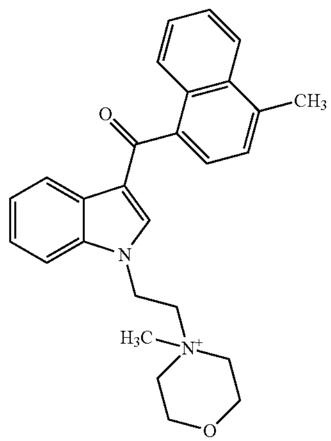 [SMILES: Cc1ccc(C(=O)c2cn(CC[N+]3(C)CCOCC3)c3ccccc23)c2ccccc12] | 4-methyl-4-{2-[3-(4-methyl-naphthalene-1-carbonyl)-1H-indol-1-yl]ethyl}morpholin-4-ium iodide | 4174.00 | | | | |
| 44 | 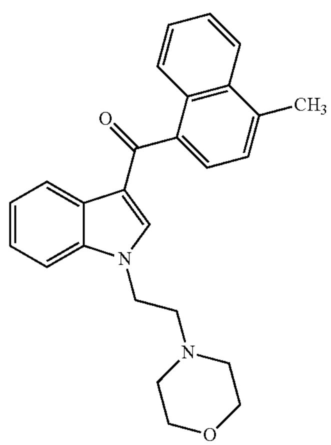 [SMILES: Cc1ccc(C(=O)c2cn(CCN3CCOCC3)c3ccccc23)c2ccccc12] | 3-(4-methyl-naphthalene-1-carbonyl)-1-[2-(morpholin-4-yl)ethyl]-1H-indole | 20.20 | | | 239.00 | |
| 50 | 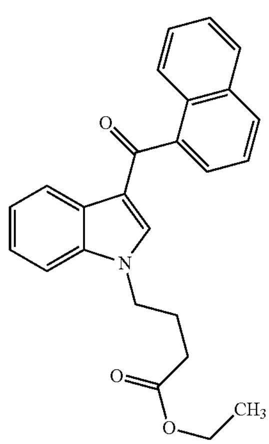 [SMILES: CCOC(=O)CCCn1cc(C(=O)c2cccc3ccccc23)c2ccccc21] | ethyl 4-[3-(naphthalene-1-carbonyl)-1H-indol-1-yl]butanoate | 747.00 | | | | |

TABLE 1-continued

| # | Structure | IUPAC Name | CB1_KI_CP | CB2_KI_CP | MDCK_BA | Ca_Flux | Ca Flux % Emax |
|---|---|---|---|---|---|---|---|
| 51 | 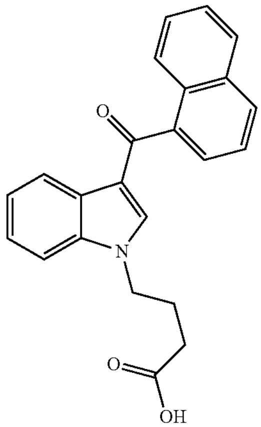 [SMILES: O=C(O)CCCn1cc(C(=O)c2cccc3ccccc23)c2ccccc21] | 4-[3-(naphthalene-1-carbonyl)-1H-indol-1-yl]butanoic acid | | | | | |
| 52 | 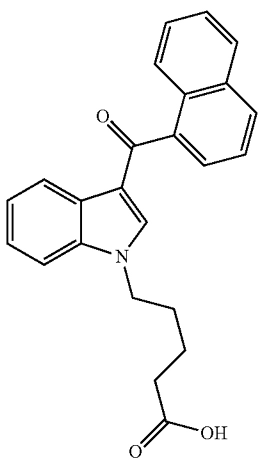 [SMILES: O=C(O)CCCCn1cc(C(=O)c2cccc3ccccc23)c2ccccc21] | 5-[3-(naphthalene-1-carbonyl)-1H-indol-1-yl]pentanoic acid | | | | | |
| 53 | 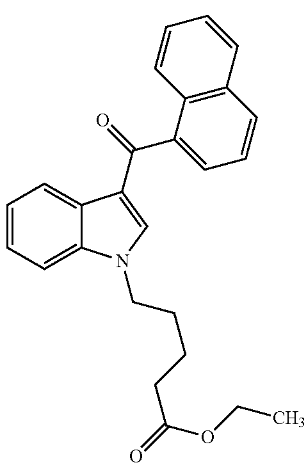 [SMILES: CCOC(=O)CCCCn1cc(C(=O)c2cccc3ccccc23)c2ccccc21] | ethyl 5-[3-(naphthalene-1-carbonyl)-1H-indol-1-yl]pentanoate | 1469.00 | | | | |

TABLE 1-continued

| # | Structure | IUPAC Name | CB1_KI_CP | CB2_KI_CP | MDCK_BA | Ca_Flux | Ca Flux % Emax |
|---|---|---|---|---|---|---|---|
| 54 | 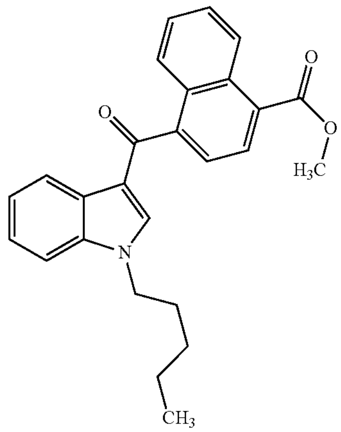 [SMILES: CCCCCn1cc(C(=O)c2ccc(C(=O)OC)c3ccccc23)c2ccccc21] | methyl 4-(1-pentyl-1H-indole-3-carbonyl) naphthalene-1-carboxylate | 20.20 | 73.40 | 0.00 | 366.00 | |
| 55 | 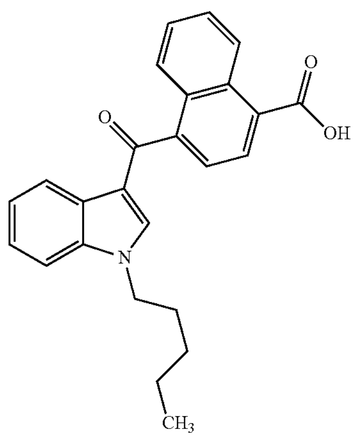 [SMILES: CCCCCn1cc(C(=O)c2ccc(C(=O)O)c3ccccc23)c2ccccc21] | 4-(1-pentyl-1H-indole-3-carbonyl) naphthalene-1-carboxylic acid | | | | | |
| 56 | 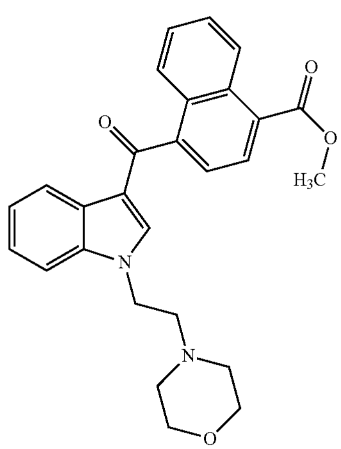 [SMILES: COC(=O)c1ccc(C(=O)c2cn(CCN3CCOCC3)c3ccccc23)c2ccccc12] | methyl 4-{1-[2-(morpholin-4-yl)ethyl]-1H-indole-3-carbonyl} naphthalene-1-carboxylate | 52.40 | 61.40 | 1.02 | 810.80 | |

TABLE 1-continued
| # | Structure | IUPAC Name | CB1_KI_CP | CB2_KI_CP | MDCK_BA | Ca_Flux | Ca Flux % Emax |
|---|---|---|---|---|---|---|---|
| 57 | 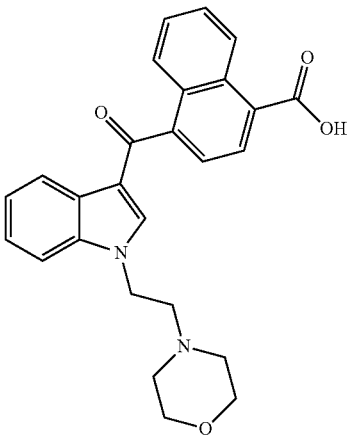 [SMILES: O=C(O)c1ccc(C(=O)c2cn(CCN3CCOCC3)c3ccccc23)c2ccccc12] | 4-{1-[2-(morpholin-4-yl)ethyl]-1H-indole-3-carbonyl}naphthalene-1-carboxylic acid | | | | | |
| 58 | 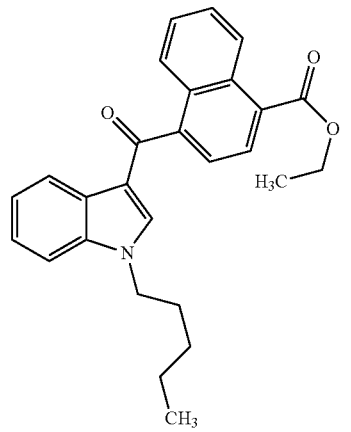 [SMILES: CCCCCn1cc(C(=O)c2ccc(C(=O)OCC)c3ccccc23)c2ccccc21] | ethyl 4-(1-pentyl-1H-indole-3-carbonyl)naphthalene-1-carboxylate | 115.00 | 53.90 | | | |
| 59 | 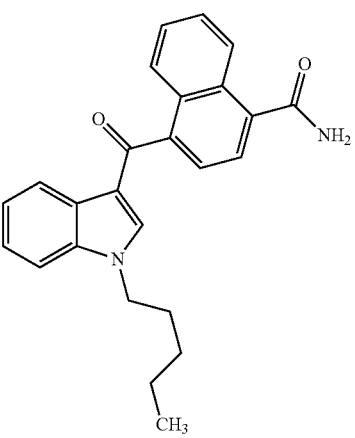 [SMILES: CCCCCn1cc(C(=O)c2ccc(C(N)=O)c3ccccc23)c2ccccc21] | 4-(1-pentyl-1H-indole-3-carbonyl)naphthalene-1-carboxamide | 96.60 | 135.00 | | | |

TABLE 1-continued

| # | Structure | IUPAC Name | CB1_KI_CP | CB2_KI_CP | MDCK_BA | Ca_Flux | Ca Flux % Emax |
|---|---|---|---|---|---|---|---|
| 60 | 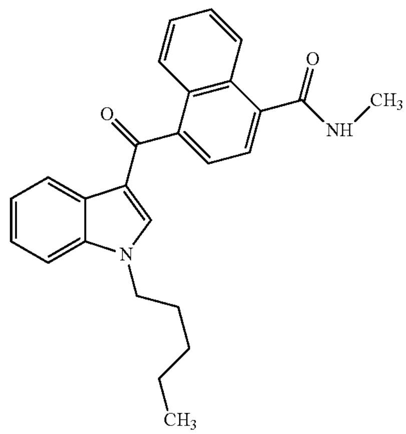 [SMILES: CCCCCn1cc(C(=O)c2ccc(C(=O)NC)c3ccccc23)c2ccccc21] | N-methyl-4-(1-pentyl-1H-indole-3-carbonyl)naphthalene-1-carboxamide | 127.00 | 303.00 | | | |
| 61 | 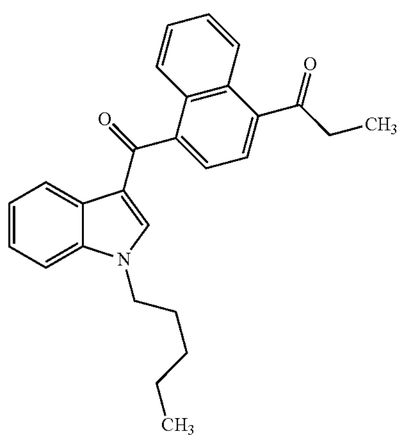 [SMILES: CCCCCn1cc(C(=O)c2ccc(C(=O)CC)c3ccccc23)c2ccccc21] | 1-[4-(1-pentyl-1H-indole-3-carbonyl)naphthalen-1-yl]propan-1-one | 5.71 | 32.70 | 0.00 | | |
| 62 | 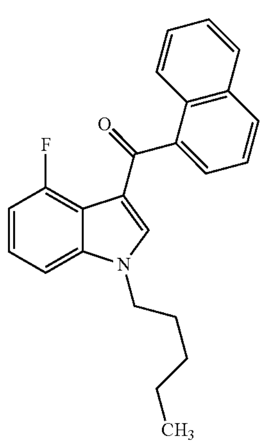 [SMILES: CCCCCn1cc(C(=O)c2cccc3ccccc23)c2c(F)cccc21] | 4-fluoro-3-(naphthalene-1-carbonyl)-1-pentyl-1H-indole | 6.50 | 35.60 | 0.00 | | |

TABLE 1-continued

| # | Structure | IUPAC Name | CB1_KI_CP | CB2_KI_CP | MDCK_BA | Ca_Flux | Ca Flux % Emax |
|---|---|---|---|---|---|---|---|
| 63 | 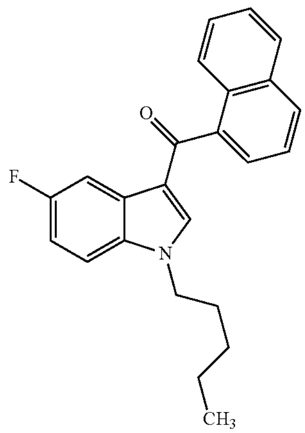 [SMILES: CCCCCn1cc(C(=O)c2cccc3ccccc23)c2cc(F)ccc21] | 5-fluoro-3-(naphthalene-1-carbonyl)-1-pentyl-1H-indole | 9.85 | 65.00 | 0.00 | | |
| 64 | 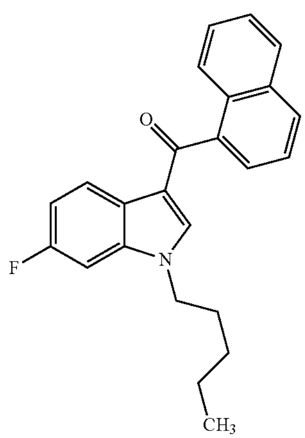 [SMILES: CCCCCn1cc(C(=O)c2cccc3ccccc23)c2ccc(F)cc21] | 6-fluoro-3-(naphthalene-1-carbonyl)-1-pentyl-1H-indole | 2.35 | 16.40 | 0.00 | | |
| 65 | 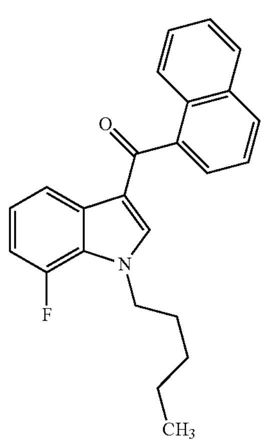 [SMILES: CCCCCn1cc(C(=O)c2cccc3ccccc23)c2cccc(F)c21] | 7-fluoro-3-(naphthalene-1-carbonyl)-1-pentyl-1H-indole | 3.62 | 2.70 | 0.00 | 104.00 | 79 |

TABLE 1-continued

| # | Structure | IUPAC Name | CB1_KI_CP | CB2_KI_CP | MDCK_BA | Ca_Flux | Ca Flux % Emax |
|---|---|---|---|---|---|---|---|
| 66 | 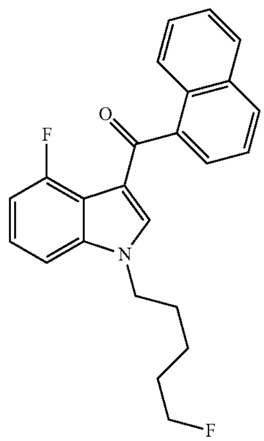 [SMILES: O=C(c1cccc2ccccc12)c1cn(CCCCCF)c2cccc(F)c12] | 4-fluoro-1-(5-fluoropentyl)-3-(naphthalene-1-carbonyl)-1H-indole | 4.38 | 2.94 | | | |
| 67 | 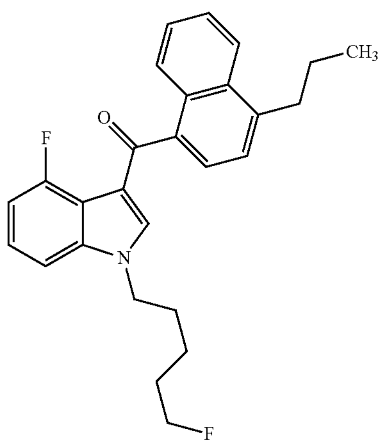 [SMILES: CCCc1ccc(C(=O)c2cn(CCCCCF)c3cccc(F)c23)c2ccccc12] | 4-fluoro-1-(5-fluoropentyl)-3-(4-propyl-naphthalene-1-carbonyl)-1H-indole | 2.55 | 3.61 | | | |
| 68 | 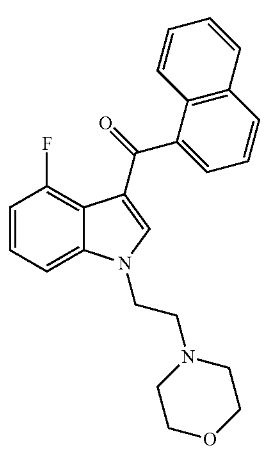 [SMILES: O=C(c1cccc2ccccc12)c1cn(CCN2CCOCC2)c2cccc(F)c12] | 4-fluoro-1-[2-(morpholin-4-yl)ethyl]-3-(naphthalene-1-carbonyl)-1H-indole | 237.00 | 95.20 | | | |

TABLE 1-continued

| # | Structure | IUPAC Name | CB1_KI_CP | CB2_KI_CP | MDCK_BA | Ca_Flux | Ca Flux % Emax |
|---|---|---|---|---|---|---|---|
| 69 | 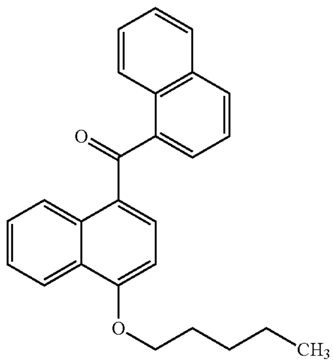 [SMILES: CCCCCOc1ccc(C(=O)c2cccc3ccccc23)c2ccccc12] | (naphthalen-1-yl)[4-(pentyloxy)naphthalen-1-yl]methanone | 17.00 | | | 198.10 | |
| 70 | 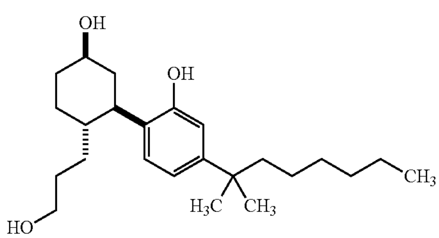 | 2-[5-hydroxy-2-(3-hydroxypropyl)cyclohexyl]-5-(2-methyloctan-2-yl)phenol | 1.17 | | | | |

TABLE 2

| # | Structure | IUPAC Name | S9% remaining @ xy min | Plasma % remaining @ xy min |
|---|---|---|---|---|
| 11 | 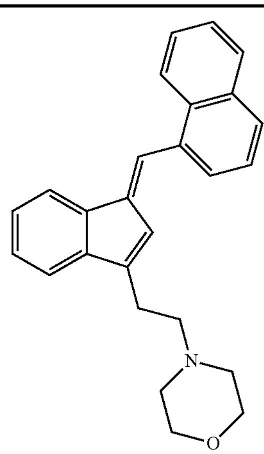 | 4-{2-[(1E)-1-(naphthalen-1-ylmethylidene)-1H-inden-3-yl]ethyl}morpholine | 35 @ 30 | 95 @ 30 |

TABLE 2-continued

| # | Structure | IUPAC Name | S9% remaining @ xy min | Plasma % remaining @ xy min |
|---|---|---|---|---|
| 54 | 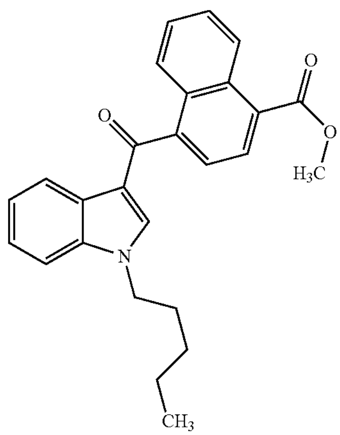 [SMILES: CCCCCn1cc(C(=O)c2ccc(C(=O)OC)c3ccccc23)c2ccccc21] | methyl 4-(1-pentyl-1H-indole-3-carbonyl)naphthalene-1-carboxylate | 2.62 @ 30 | 9.6 @ 30 |
| 56 | 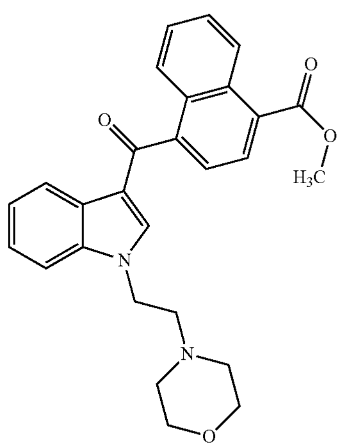 [SMILES: COC(=O)c1ccc(C(=O)c2cn(CCN3CCOCC3)c3ccccc23)c2ccccc12] | methyl 4-{1-[2-(morpholin-4-yl)ethyl]-1H-indole-3-carbonyl}naphthalene-1-carboxylate | 0 @ 60 | 0 @ 60 |
| 61 | 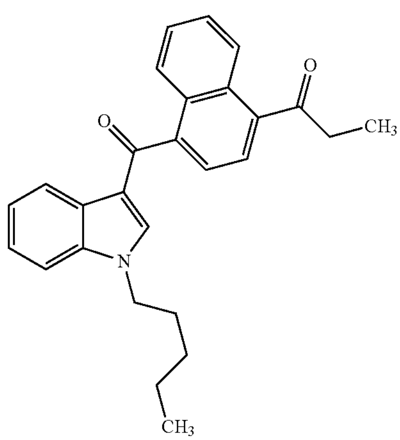 [SMILES: CCCCCn1cc(C(=O)c2ccc(C(=O)CC)c3ccccc23)c2ccccc21] | 1-[4-(1-pentyl-1H-indole-3-carbonyl)naphthalen-1-yl]propan-1-one | 3 @ 60 | 75 @ 60 |

TABLE 2-continued

| # | Structure | IUPAC Name | S9% remaining @ xy min | Plasma % remaining @ xy min |
|---|---|---|---|---|
| 62 | 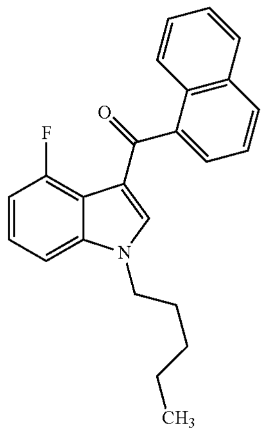 [SMILES: CCCCCn1cc(C(=O)c2cccc3ccccc23)c2c(F)cccc21] | 4-fluoro-3-(naphthalene-1-carbonyl)-1-penyl-1H-indole | 5 @ 60 | 69 @ 60 |
| 63 | 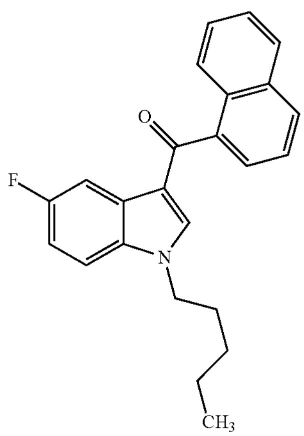 [SMILES: CCCCCn1cc(C(=O)c2cccc3ccccc23)c2cc(F)ccc21] | 5-fluoro-3-(naphthalene-1-carbonyl)-1-pentyl-1H-indole | 13 @ 60 | 99 @ 60 |
| 65 | 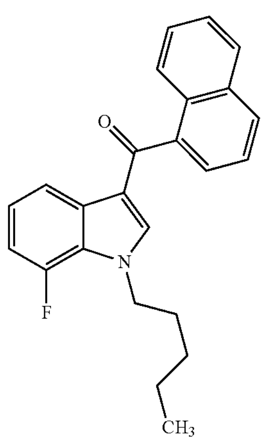 [SMILES: CCCCCn1cc(C(=O)c2cccc3ccccc23)c2cccc(F)c21] | 7-fluoro-3-(naphthalene-1-carbonyl)-1-pentyl-1H-indole | ~58 @ 30; 50 @ 60; 36 @ 120 | 97 @ 60 |

TABLE 2-continued

| # | Structure | IUPAC Name | S9% remaining @ xy min | Plasma % remaining @ xy min |
|---|---|---|---|---|
| 67 | 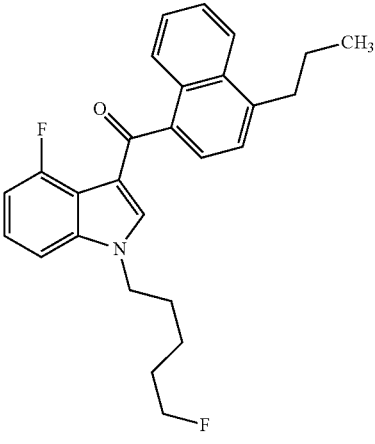 [SMILES: CCCc1ccc(C(=O)c2cn(CCCCCF)c3cccc(F)c23)c2ccccc12] | 4-fluoro-1-(5-fluoropentyl)-3-(4-propylnaphthalene-1-carbonyl)-1H-indole | 6 @ 60 | 95 @ 60 |

TABLE 3

| # | Structure | IUPAC Name | SNE Neuropath Assay-% return to pre-drug (0.3 mg/kg) contralateal threshold at 2-3 h | Catalepsy % change from pre-drug (0.3 mg/kg) at 1-3 hrs | Hypo-thermia % change from predrug (0.3 mg/kg) at 2-3 hr | Rotarod % change from pre-drug (0.3 mg/kg) at 2-3 hr |
|---|---|---|---|---|---|---|
| 9 | 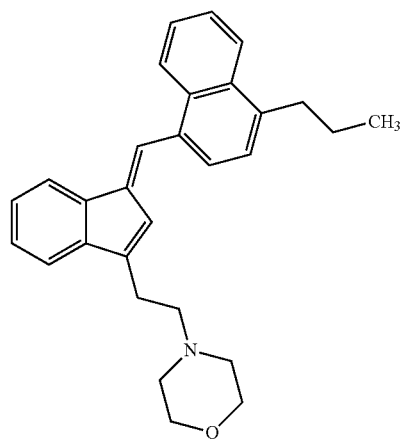 [SMILES: CCCc1ccc(/C=C2\C=C(CCN3CCOCC3)c3ccccc32)c2ccccc12] | 4-{2-[(1E)-1-[(4-propylnaphthalen-1-yl)methylidene]-1H-inden-3-yl]ethyl}morpholine | 110 | 0 | 0 | 0 |

TABLE 3-continued

| # | Structure | IUPAC Name | SNE Neuropath Assay-% return to pre-drug (0.3 mg/kg) contralateal threshold at 2-3 h | Catalepsy % change from pre-drug (0.3 mg/kg) at 1-3 hrs | Hypo-thermia % change from predrug (0.3 mg/kg) at 2-3 hr | Rotarod % change from pre-drug (0.3 mg/kg) at 2-3 hr |
|---|---|---|---|---|---|---|
| 10 | 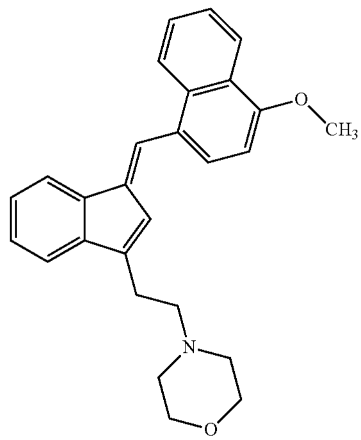 | 4-{2-[(1E)-1-[(4-methoxynaphthalen-1-yl)methylidene]-1H-inden-3-yl]ethyl}morpholine | 103.2 | 0 | 0 | 0 |
| 11 | 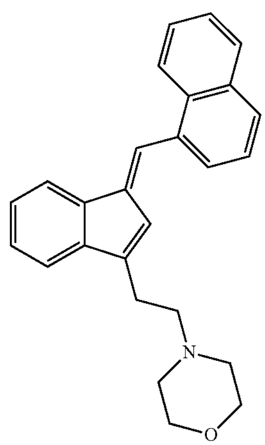 [SMILES: C1=C(CCN2CCOCC2)c2ccccc2/C1=C/c1cccc2ccccc12] | 4-{2-[(1E)-1-(naphthalen-1-ylmethylidene)-1H-inden-3-yl]ethyl}morpholine | 37.8 | 0 | 0 | 0 |
| 54 | 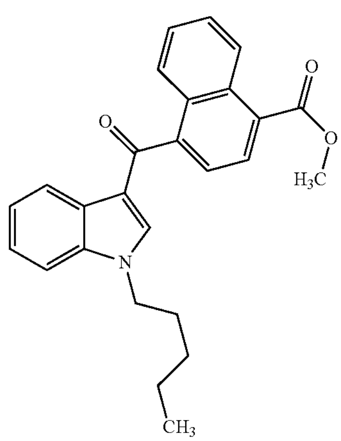 [SMILES: CCCCCn1cc(C(=O)c2ccc(C(=O)OC)c3ccccc23)c2ccccc21] | methyl 4-(1-pentyl-1H-indole-3-carbonyl)naphthalene-1-carboxylate | 0 | | | |

TABLE 3-continued

| # | Structure | IUPAC Name | SNE Neuropath Assay-% return to pre-drug (0.3 mg/kg) contralateal threshold at 2-3 h | Catalepsy % change from pre-drug (0.3 mg/kg) at 1-3 hrs | Hypo-thermia % change from predrug (0.3 mg/kg) at 2-3 hr | Rotarod % change from pre-drug (0.3 mg/kg) at 2-3 hr |
|---|---|---|---|---|---|---|
| 64 | 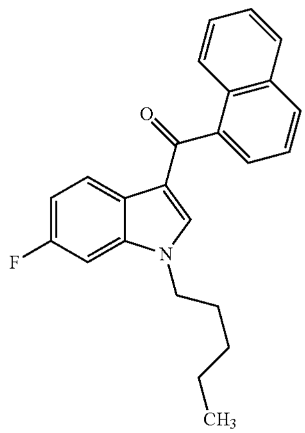 [SMILES: CCCCCn1cc(C(=O)c2cccc3ccccc23)c2ccc(F)cc21] | 6-fluoro-3-(naphthalene-1-carbonyl)-1-pentyl-1H-indole | 54.4 | | | |
| 65 | 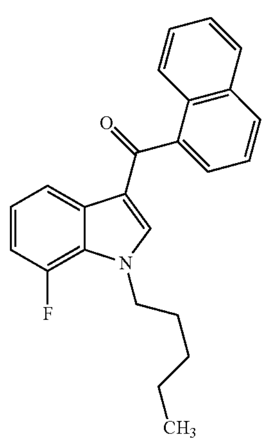 [SMILES: CCCCCn1cc(C(=O)c2cccc3ccccc23)c2cccc(F)c21] | 7-fluoro-3-(naphthalene-1-carbonyl)-1-pentyl-1H-indole | 18.6 | 0 | 0 | 0 |

While the invention has been described and illustrated herein by references to various specific materials, procedures and examples, it is understood that the invention is not restricted to the particular combinations of material and procedures selected for that purpose. Numerous variations of such details can be implied as will be appreciated by those skilled in the art. It is intended that the specification and examples be considered as exemplary, only, with the true scope and spirit of the invention being indicated by the following claims. All references, patents, and patent applications referred to in this application are herein incorporated by reference in their entirety.

The invention claimed is:

1. A compound having the structure

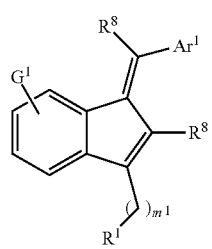

wherein

Ar$^1$ is alkyl substituted 1-naphthyl;

m$^1$ is 1, 2, 3, 4, 5, or 6;

R$^1$ is morpholin-4-yl; and

G$^1$ is one, two, three, or four substituents, each independently selected from hydrogen, halogen, fluorine, hydroxyl, alkoxy, and methylenedioxy; and each R$^8$ independently is H or alkyl.

2. The compound of claim 1, wherein m$^1$ is 1 or 2.

3. The compound of claim 1, wherein G$^1$ is one fluorine substituent.

4. The compound of claim 1, wherein Ar$^1$ is selected from the group consisting of

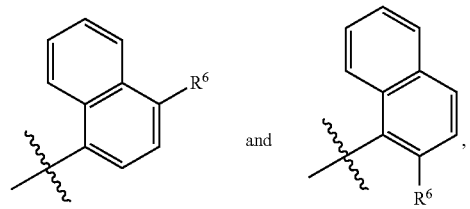

and R$^6$ is alkyl.

5. The compound of claim 1, wherein R$^8$ is hydrogen.

6. The compound of claim 1, selected from:

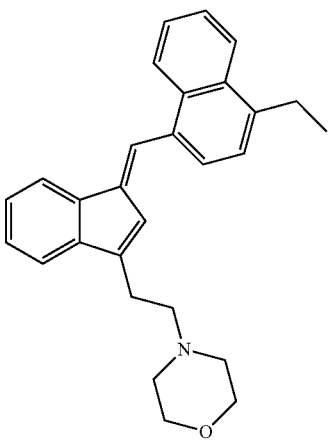

and

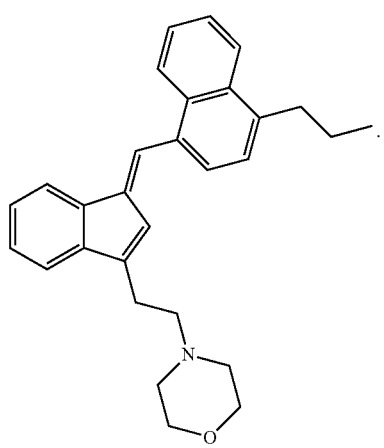

7. A pharmaceutical composition comprising a compound according to claim 1 and a pharmaceutically acceptable excipient.

8. A method for treating a disease or disorder in a subject comprising administering to a subject a compound according to claim 1, wherein the disease or disorder may be treated by activating or blocking a peripheral cannabinoid receptor.

9. The method of claim 8, wherein the compound has less than 10% permeability across the blood brain barrier, as measured using the Madin-Darby canine kidney cell line assay.

10. The method of claim 8, wherein the disorder is pain.

11. The method of claim 10, wherein the pain is chronic, inflammatory, or neuropathic.

12. The method of claim 8, wherein said disease or disorder is hyperalgesia or allodynia.

13. The method of claim 8, wherein said disease or disorder is rheumatoid arthritis, inflammatory bowel disorders, soft tissue pain, bone cancer pain, chemotherapy-induced neuropathy, pain caused by thermal injury, pain caused by nerve injury, and pain caused by cancer.

14. The method of claim 8, wherein said disease or disorder is intraocular pressure.

15. The method of claim 8, wherein said treatment is anti-emetic, or anti-nausea treatment.

16. The method of claim 8, wherein said disease or disorder is a tumor.

17. The method of claim 8, wherein said disease or disorder is a bone disease associated with accelerated bone resorption.

18. The method of claim 17, wherein the bone disorder is osteoporosis, rheumatoid arthritis, or bone metastasis.

* * * * *